(12) United States Patent
Nalagatla et al.

(10) Patent No.: US 8,573,464 B2
(45) Date of Patent: Nov. 5, 2013

(54) CIRCULAR STAPLING INSTRUMENT HAVING A BREAKAWAY WASHER ATTACHMENT MEMBER

(75) Inventors: Anil K. Nalagatla, Mason, OH (US); Michael L. Kruszynski, Loveland, OH (US); Thomas E. Adams, Loveland, OH (US)

(73) Assignee: Ethicon Endo-Surgery, Inc., Cincinatti, OH (US)

( * ) Notice: Subject to any disclaimer, the term of this patent is extended or adjusted under 35 U.S.C. 154(b) by 78 days.

(21) Appl. No.: 13/111,702

(22) Filed: May 19, 2011

(65) Prior Publication Data

US 2012/0292371 A1 Nov. 22, 2012

(51) Int. Cl.
*A61B 17/068* (2006.01)

(52) U.S. Cl.
USPC .................. 227/179.1; 227/175.1; 227/180.1; 227/181.1; 227/19; 606/219

(58) Field of Classification Search
USPC ............... 227/175.1, 180.1, 181.1, 19, 179.1; 606/219
See application file for complete search history.

(56) References Cited

U.S. PATENT DOCUMENTS

| 3,555,262 | A | | 1/1971 | Shimada |
|---|---|---|---|---|
| 4,207,898 | A | | 6/1980 | Becht |
| 4,351,466 | A | | 9/1982 | Noiles |
| 4,505,272 | A | | 3/1985 | Utyamyshev et al. |
| 5,292,053 | A | | 3/1994 | Bilotti et al. |
| 5,344,059 | A | | 9/1994 | Green et al. |
| 5,588,579 | A | * | 12/1996 | Schnut et al. ............. 227/175.1 |
| 5,860,581 | A | | 1/1999 | Robertson et al. |
| 6,083,241 | A | | 7/2000 | Longo et al. |
| 6,102,271 | A | | 8/2000 | Longo et al. |
| 6,193,129 | B1 | | 2/2001 | Bittner et al. |
| 2010/0237132 | A1 | | 9/2010 | Measamer et al. |

* cited by examiner

*Primary Examiner* — Michelle Lopez
(74) *Attorney, Agent, or Firm* — Klintworth & Rozenblat IP LLC

(57) ABSTRACT

A stapling cartridge assembly for a circular stapling instrument includes a casing, a staple driver, and a blade. The staple driver is receivable within the casing and configured to move within the casing from a pre-fired position to a fired position. The blade is attachable to the staple driver. The blade includes a cutting edge and a breakaway washer attachment member for fixedly attaching to a breakaway washer when the staple driver is moved from the pre-fired position to the fired position.

6 Claims, 51 Drawing Sheets

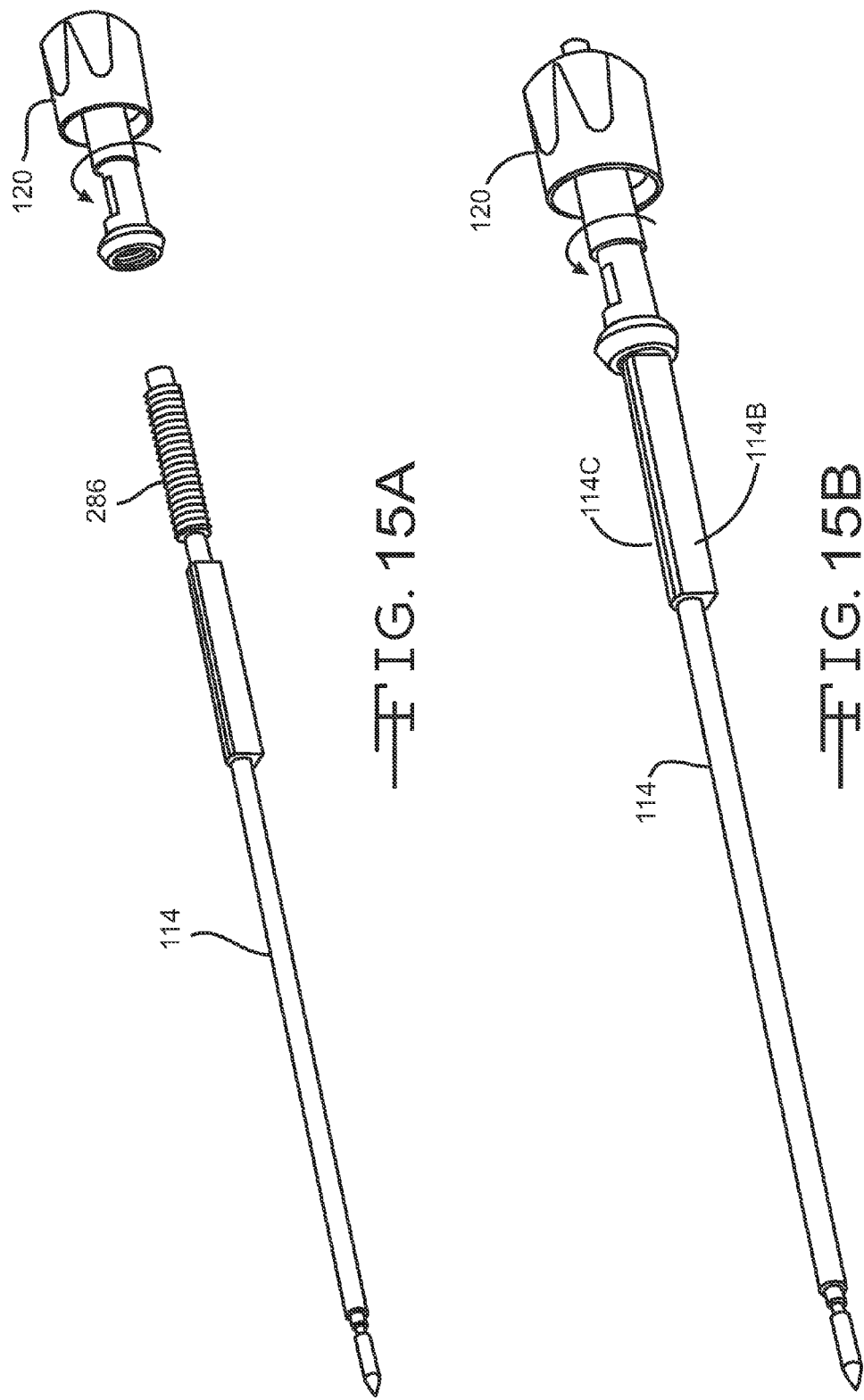

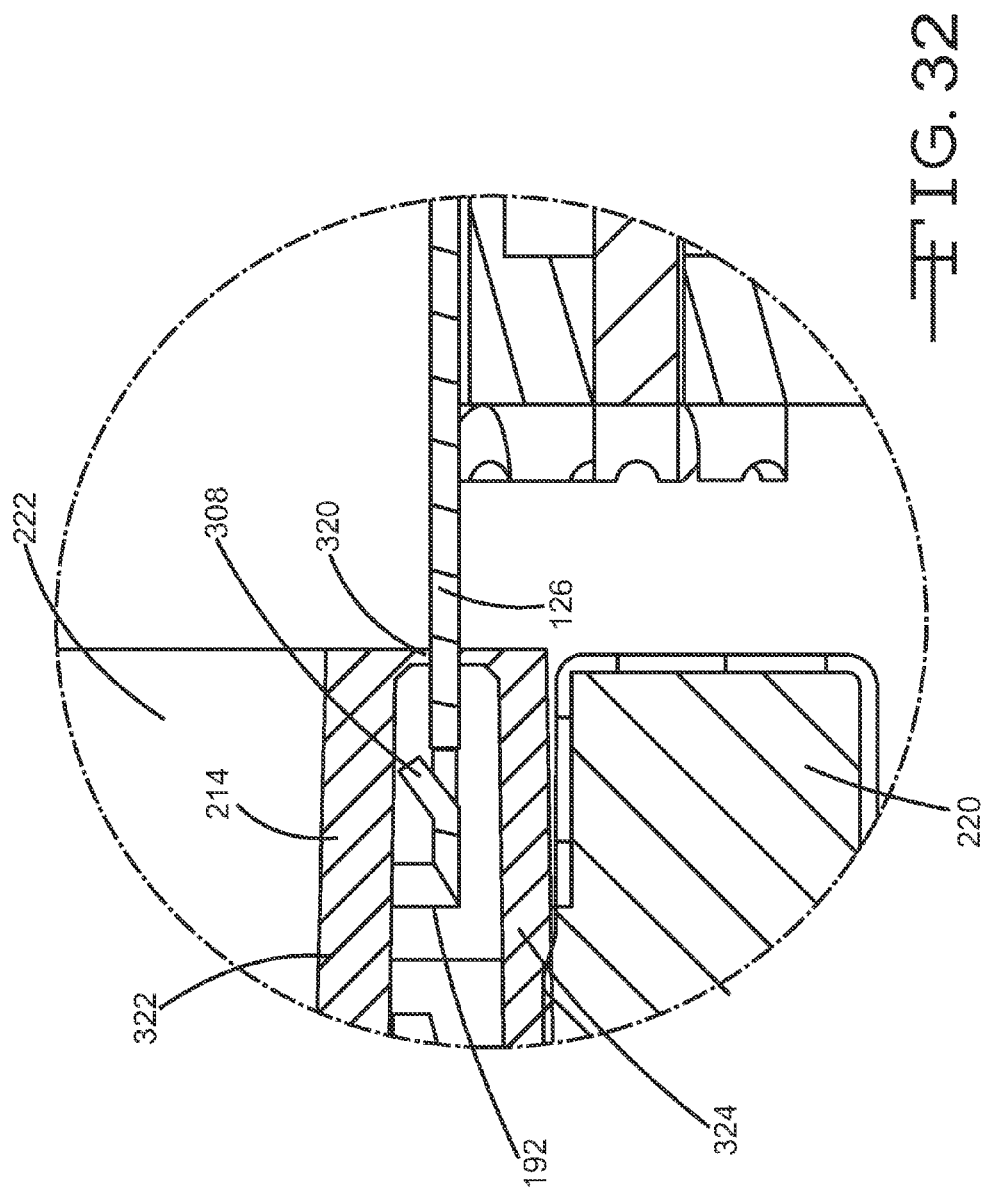

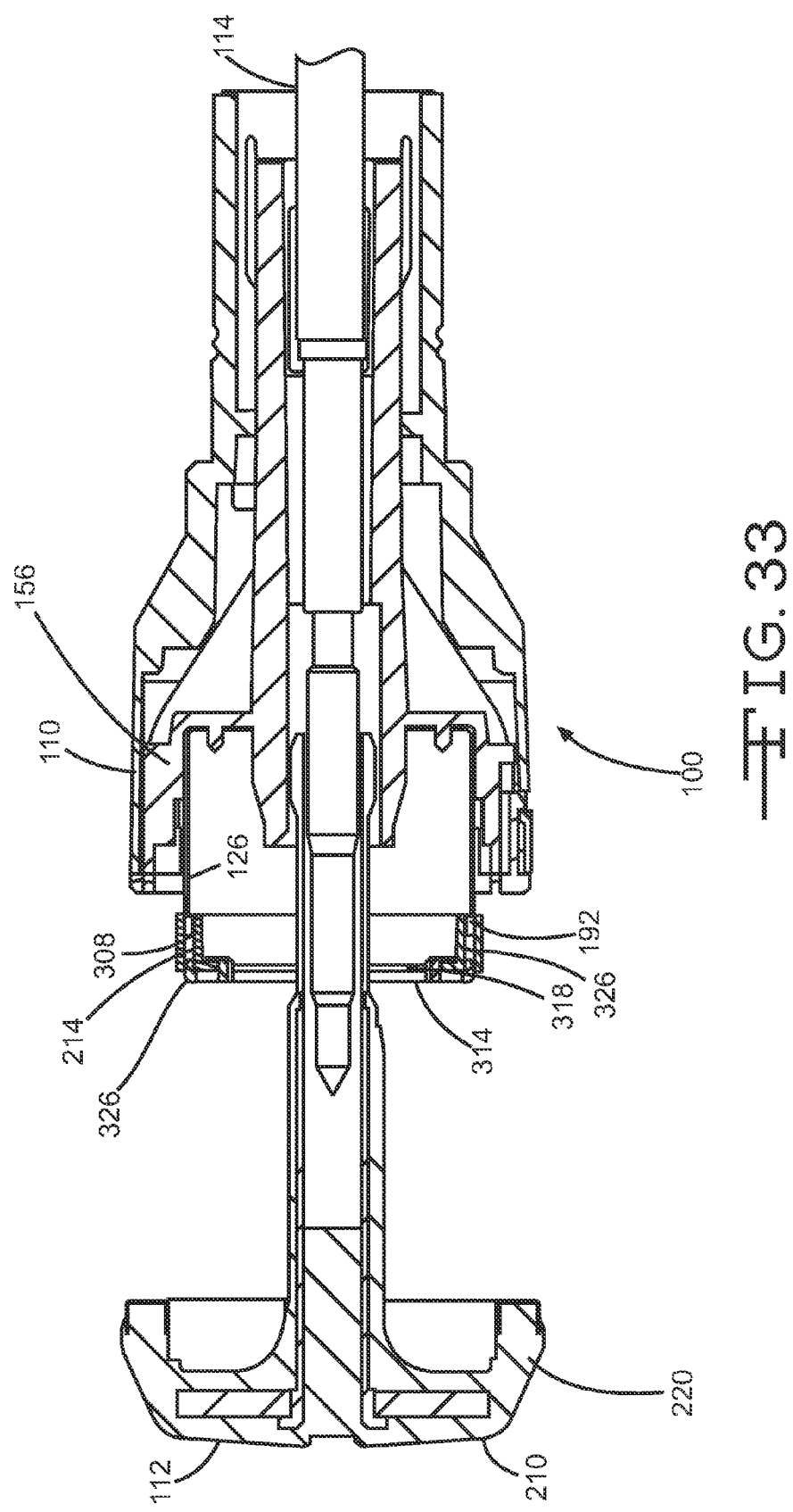

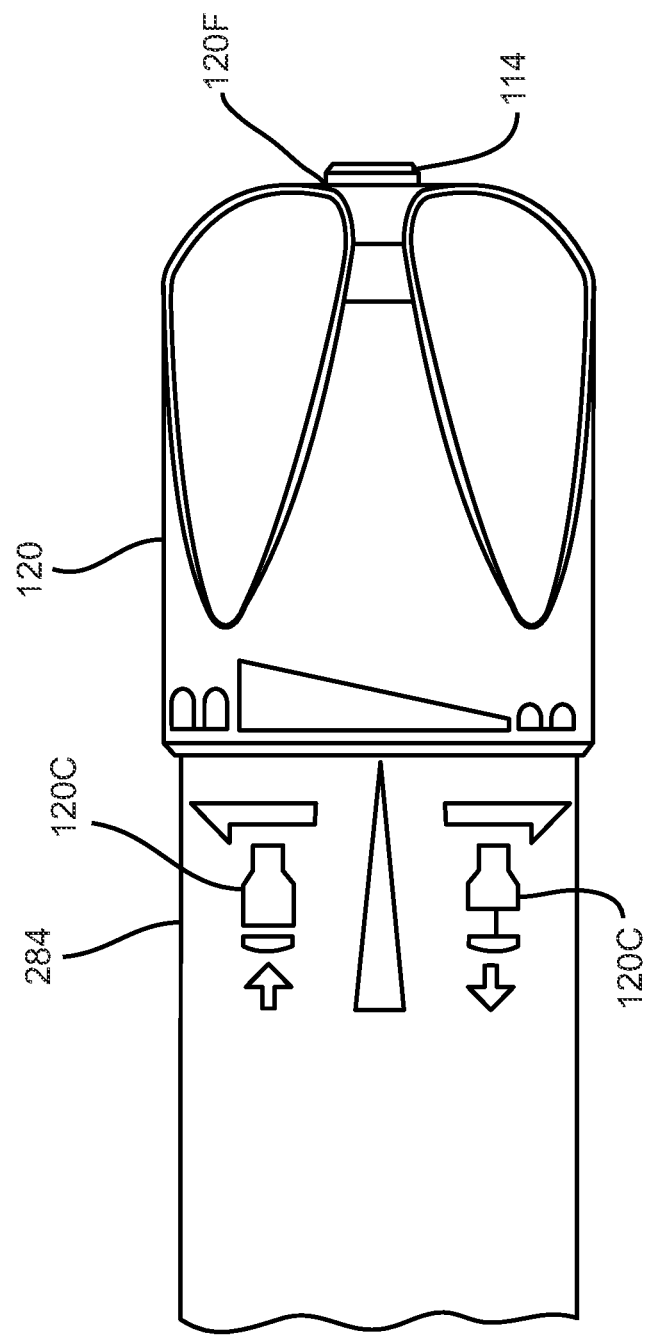

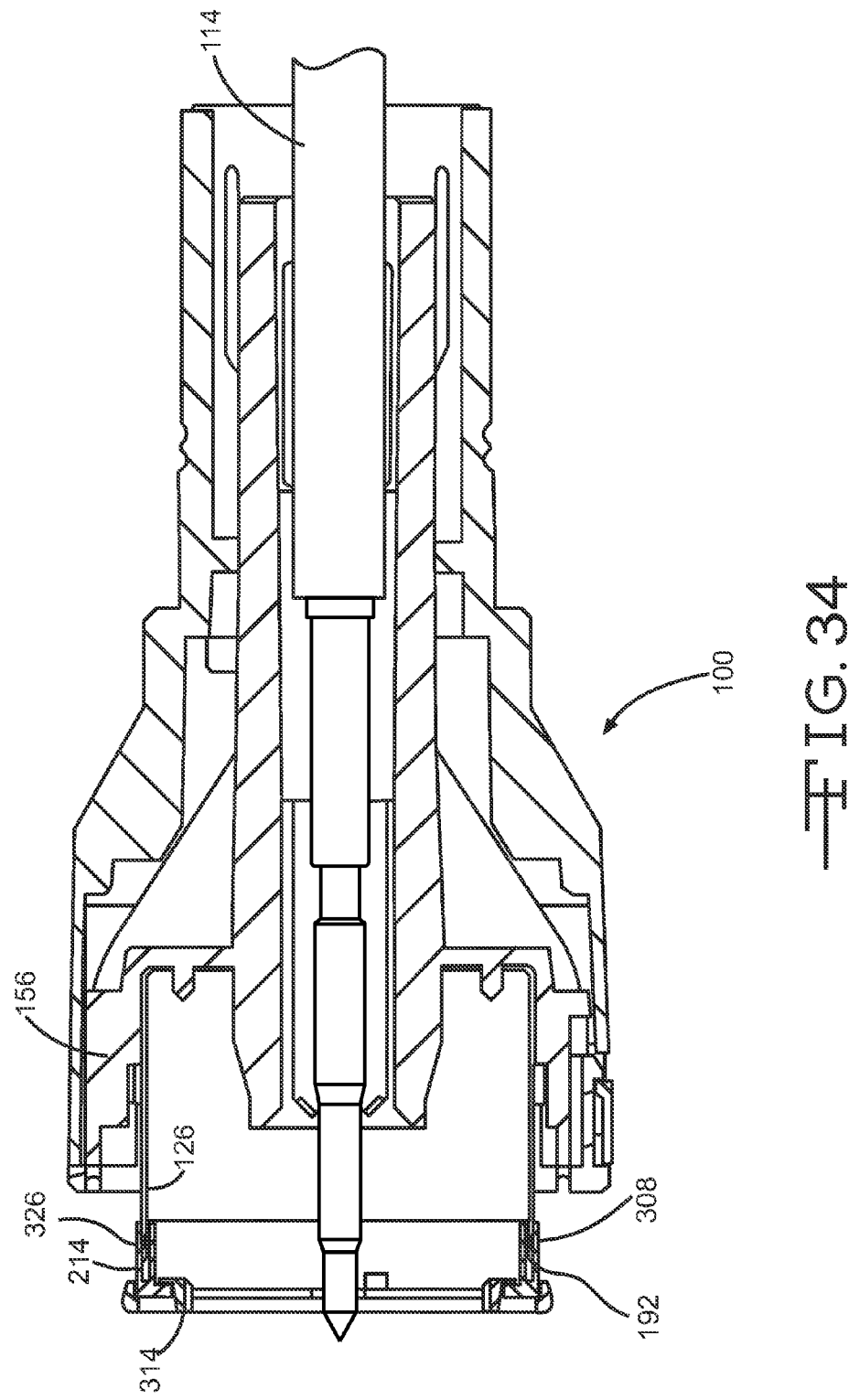

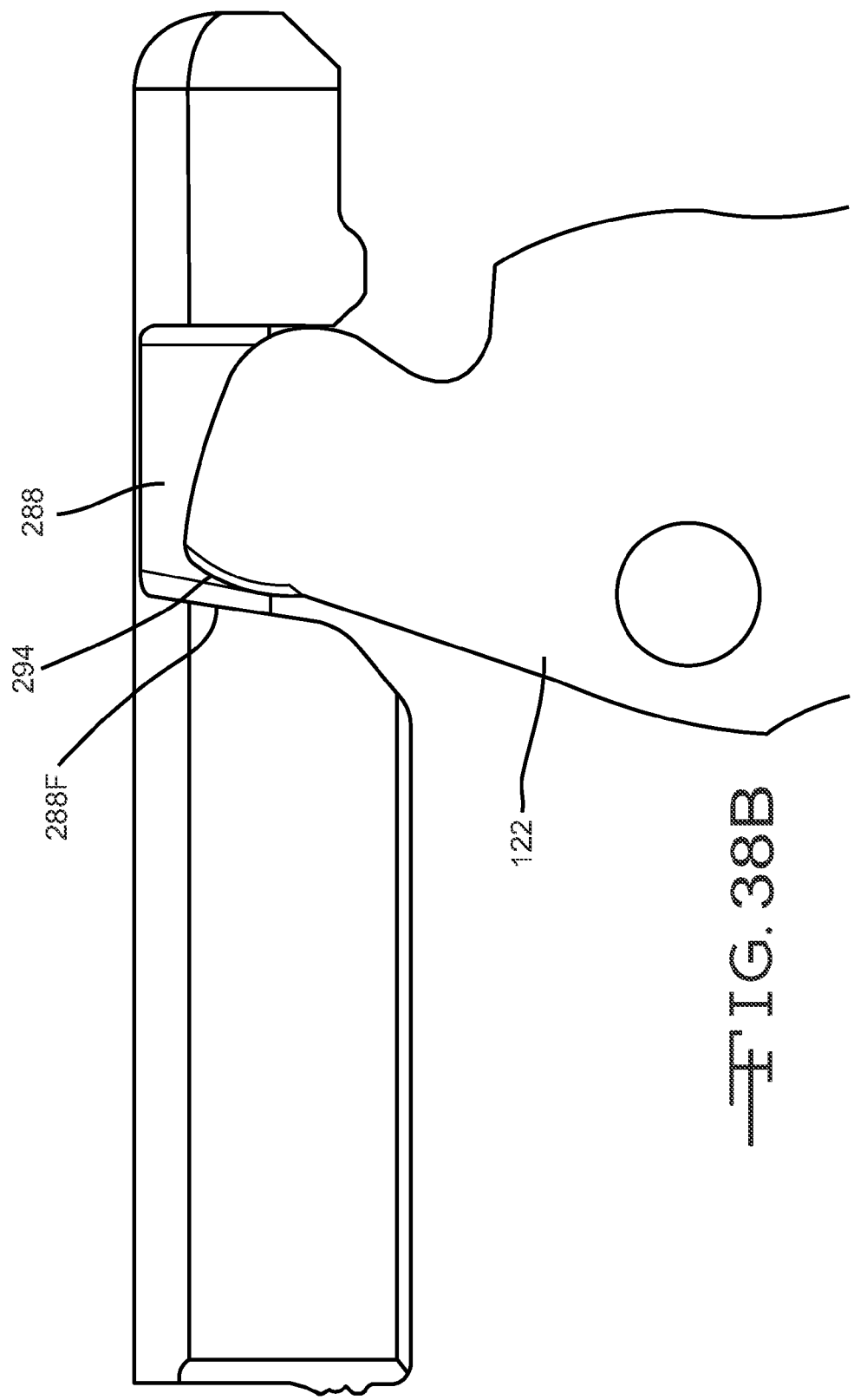

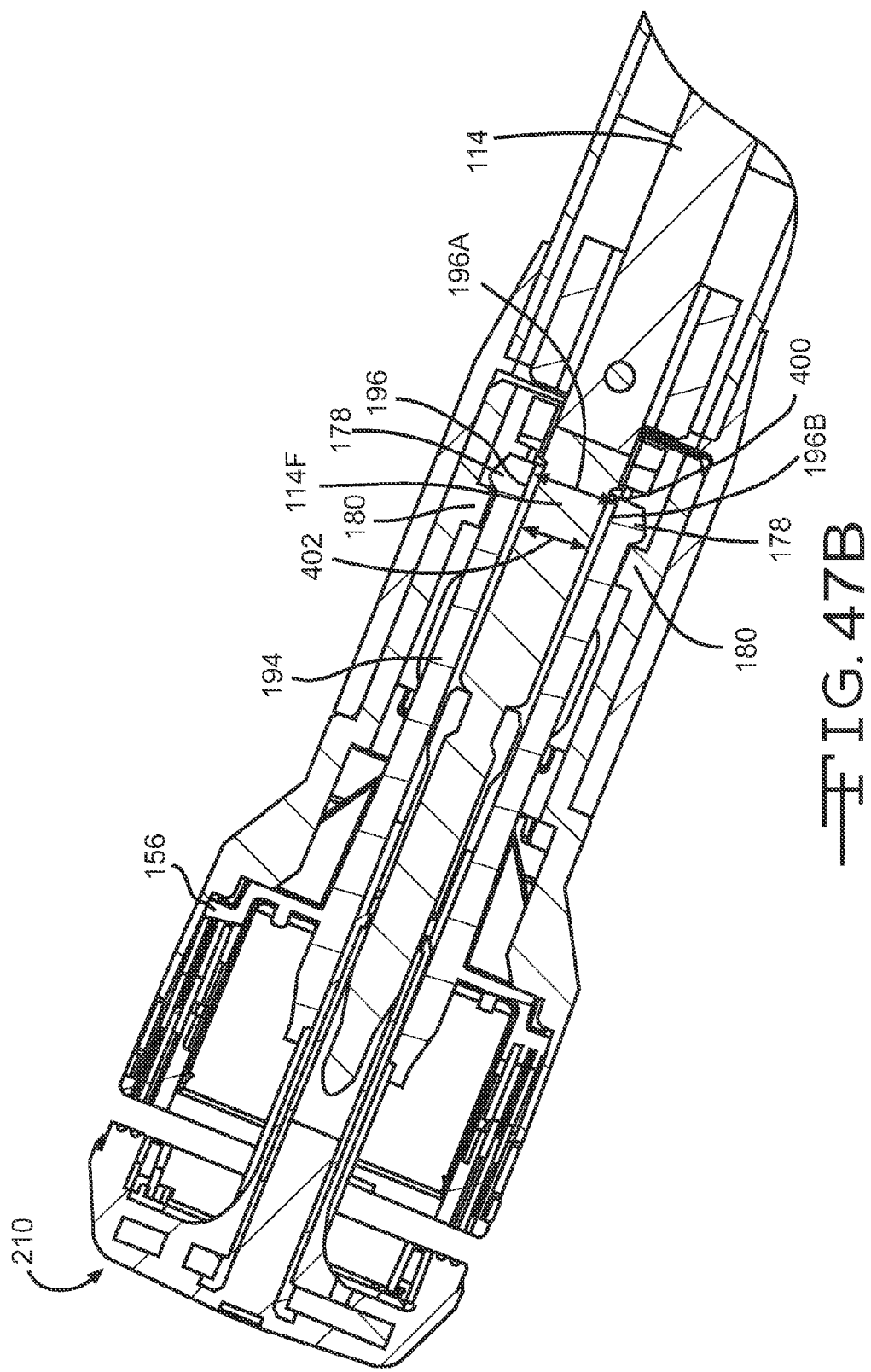

CIRCULAR STAPLING INSTRUMENT HAVING A BREAKAWAY WASHER ATTACHMENT MEMBER

FIELD OF THE DISCLOSURE

The present disclosure relates generally to a breakaway washer attachment member of a blade of a circular stapler.

BACKGROUND OF THE DISCLOSURE

Circular stapling instruments are well known in the surgical art for bowel surgery. An example of such a device is the Endopath ILS ECS 25 Endoscopic Curved Intraluminal Stapler made by Ethicon Endo Surgery Inc. Many circular stapler patents exist, for example U.S. Pat. No. 4,207,898 to Becht, U.S. Pat. No. 4,351,466 to Noiles, U.S. Pat. No. 5,292,053 to Bilotti et al., and U.S. Pat. No. 5,344,059 to Green et. al.

Typically circular stapling instruments are designed to be used once, during which cutting and stapling is completed, and then disposed of. The annular blade used for cutting tissue is advanced during the cutting and then retracted back into the device after use, thereby protecting the annular blade knife edge. However the circular stapling instrument may be inadvertently reused a second time if the circular stapling instrument is not immediately disposed of after the first use. On occasion reusable circular stapling instruments may leave the annular blade in an advanced position after use. This may pose a hazard to the user related to an exposed sharp edge. Some reusable circular stapling instruments rely solely on friction to retain a solid cutting board over and covering the annular blade knife edge. This is not a reliable means for covering the exposed annular blade knife edge as in some cases the cover may separate from the annular blade knife edge exposing the annular blade knife edge.

An apparatus for a circular stapling instrument, and a method for its use, is needed to reduce one or more problems of the prior circular stapling instruments.

SUMMARY

The present disclosure is defined by the claims, and nothing in this section should be taken as a limitation on those claims.

In one aspect, a stapling cartridge assembly for a circular stapling instrument is provided. The stapling cartridge assembly comprises a casing, a staple driver, and a blade. The staple driver is receivable within the casing and configured to move within the casing from a pre-fired position to a fired position. The blade is attachable to the staple driver. The blade comprises a cutting edge and a breakaway washer attachment member for fixedly attaching to a breakaway washer when the staple driver is moved from the pre-fired position to the fired position.

In another aspect, a circular stapling instrument is provided. The circular stapling instrument comprises a casing, a staple driver, an anvil assembly, and a blade. The staple driver is disposed within the casing and moveable within the casing from a pre-fired position to a fired position. The anvil assembly comprises a breakaway washer assembly attached to an anvil base surface. The anvil assembly is moveable from an open position away from the casing to a closed position adjacent the casing. The blade is attached to the staple driver. The blade comprises a breakaway washer attachment member. When the staple driver is in the pre-fired position, the breakaway washer is not cut by the blade and the breakaway washer attachment member is not attached to the breakaway washer. When the staple driver is in the fired position and the anvil assembly is in the closed position, the blade cuts the breakaway washer and the breakaway washer attachment member fixedly attaches to the cut breakaway washer.

In an additional aspect, a method of locking a blade to a breakaway washer of a circular stapling instrument is provided. In one step, a circular stapling instrument is provided. The provided circular stapling instrument comprises a casing, a staple driver, an anvil assembly, and a blade. The staple driver is moveably disposed within the casing. The anvil assembly comprises a breakaway washer attached to an anvil base surface. The blade is attached to the staple driver. In another step, the anvil assembly is moved from an open position away from the casing to a closed position adjacent the casing. In an additional step, the staple driver is moved from a pre-fired position, in which the blade has not cut the breakaway washer and a breakaway washer attachment member of the blade has not attached to the breakaway washer, to a fired position in which the blade cuts the breakaway washer and the breakaway washer attachment member of the blade fixedly attaches to the cut breakaway washer.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

FIG. 3A illustrates a cross-sectional view through line 3A-3A of a portion of a reciprocating anvil adjusting rod of the reusable circular stapling instrument of FIG. 3;

FIG. 3B illustrates a cross-sectional view through line 3B-3B of another portion of the reciprocating anvil adjusting rod of the reusable circular stapling instrument of FIG. 3;

FIGS. 15A and 15B illustrate perspective assembly views, during different stages of assembly, of an anvil closure knob and a reciprocating anvil adjusting rod of the reusable circular stapling instrument of FIG. 1;

FIG. 32 illustrates a close-up view, within the dotted circle of the annular blade of FIG. 31, showing the annular blade cutting the annular breakaway washer;

FIG. 33 illustrates the view of FIG. 31 with the anvil assembly having been moved back into the open position after the annular blade was fired;

FIG. 33A illustrates a close-up side view of one embodiment of an anvil control member connected to a handle of a reusable circular stapling instrument;

FIG. 34 illustrates the view of FIG. 33 with an anvil of the anvil assembly removed from the circular stapling instrument and the annular breakaway washer and a protective member attached to the annular blade;

FIG. 38B illustrates a close-up view showing the relationship between a firing trigger and the firing bar in the assembled condition of FIG. 17C;

FIGS. 47A and 47B illustrate cross-sectional views of a stapling reload assembly in an attached state to a handle, with an anvil in open and closed conditions respectively.

DETAILED DESCRIPTION

Figure 1:
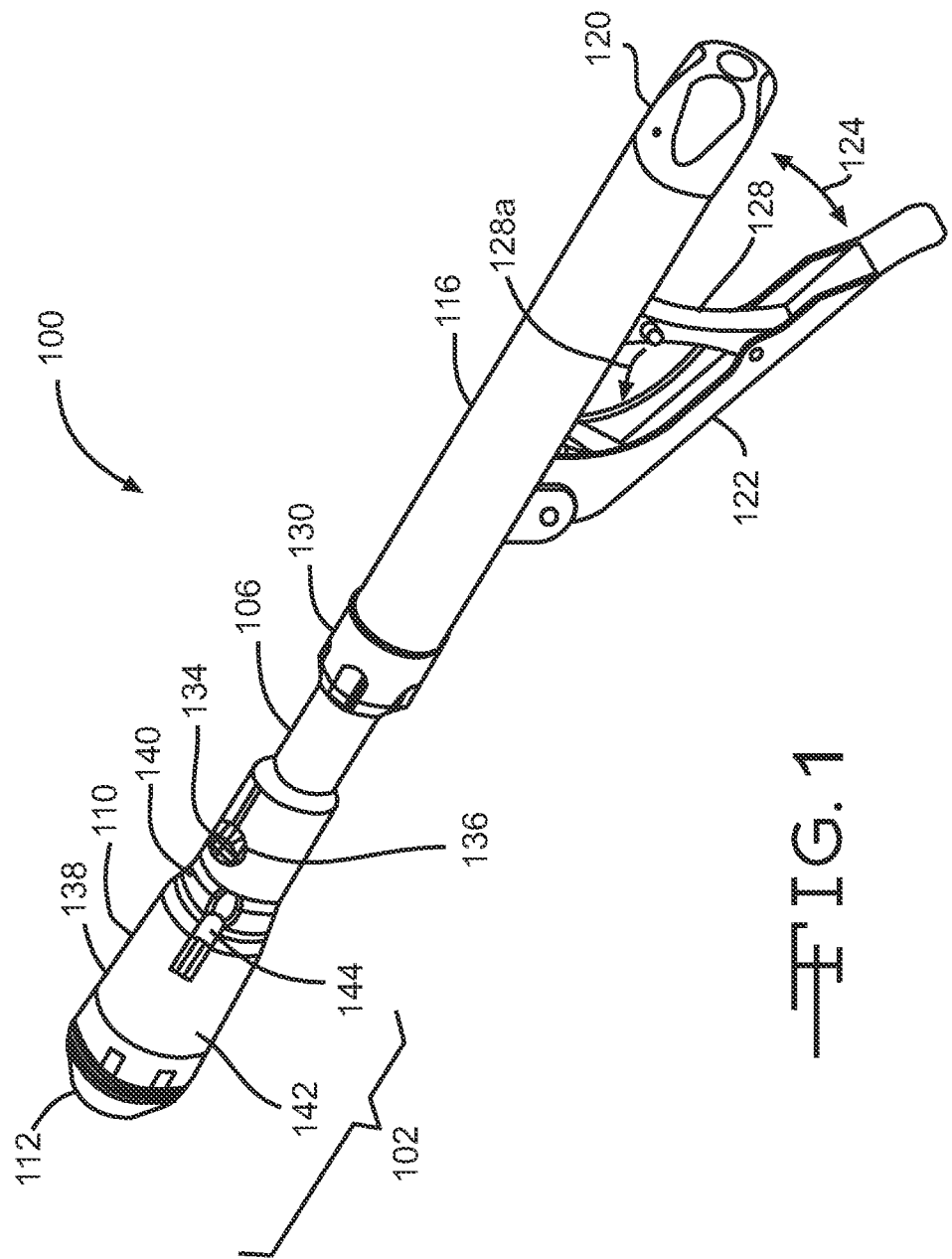
FIG. 1 illustrates a perspective view of a reusable circular stapling instrument having an open assembly architecture, in accordance with one preferred embodiment.

With reference to FIG. 1, there is shown a novel surgical circular stapling instrument 100 for the removal of tissue from a human patient consistent with the present disclosure. The surgical circular stapling instrument 100 may be used to remove tissue comprising internal hemorrhoids, or other types of human tissue. The circular stapling instrument 100 has been adapted from a conventional circular stapling instrument, as shown in U.S. Pat. No. 6,102,271, the contents of which are incorporated by reference herein in their entirety. The circular stapling instrument 100 has a stapling reload assembly 102 adapted to place an annular array of staples 104 (see FIGS. 7 and 31) into a mucosal layer at the base of internal hemorrhoids and to cut the mucosal tissue along with the internal hemorrhoids from the inside wall of a rectum or anus. In general, circular stapling instrument 100 may be used to anastomose two sections of bowel together with an annular ring of the staples 104 (see FIGS. 7 and 31) while cutting a plug from a center of an annular formed staple ring for the passage of fecal material.

Figure 2:
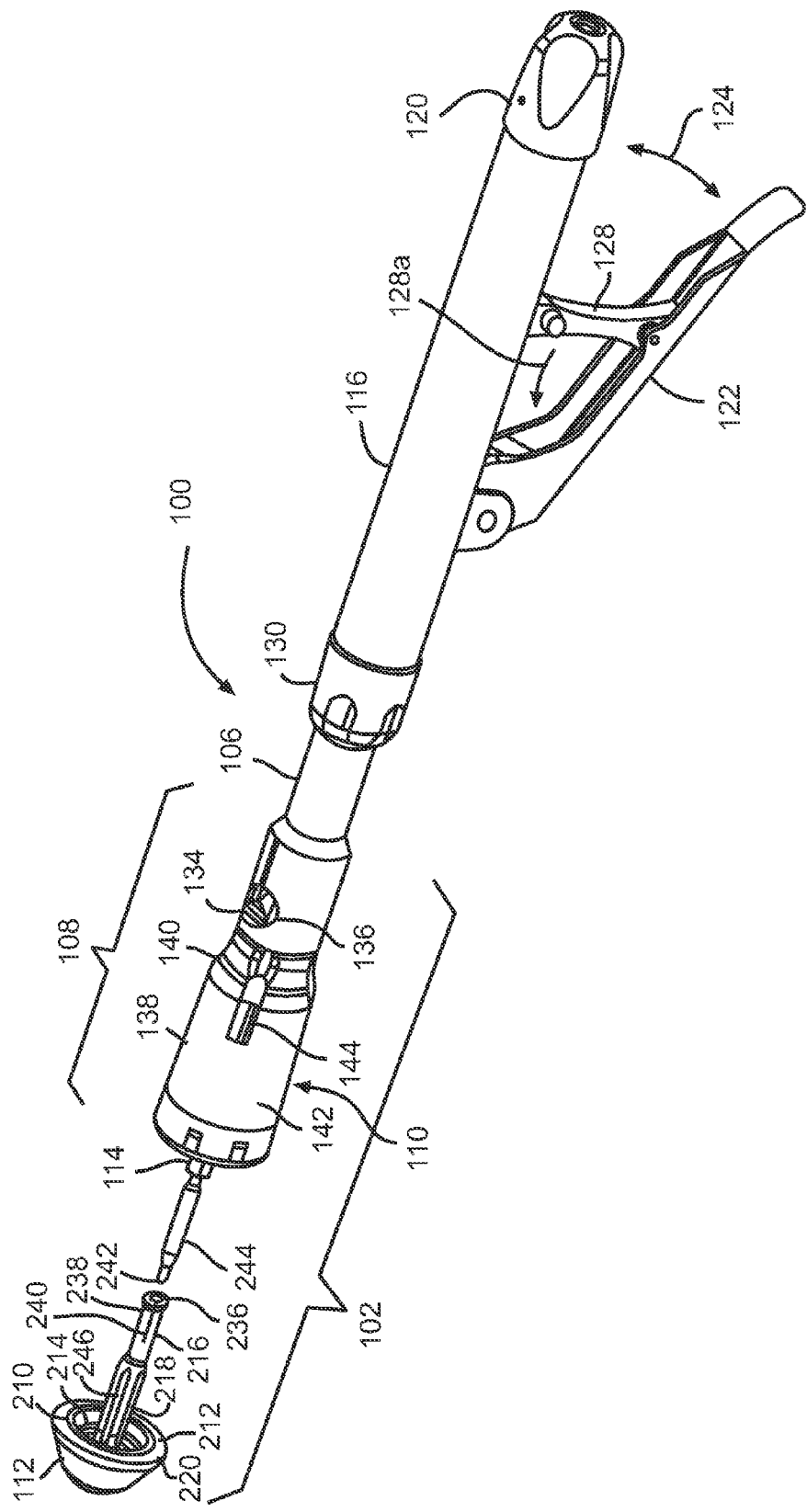
FIG. 2 illustrates a perspective view of the reusable circular stapling instrument of FIG. 1 with the instrument in the open position with an anvil assembly separated from the remainder of the reusable circular stapling instrument.
Figure 3:
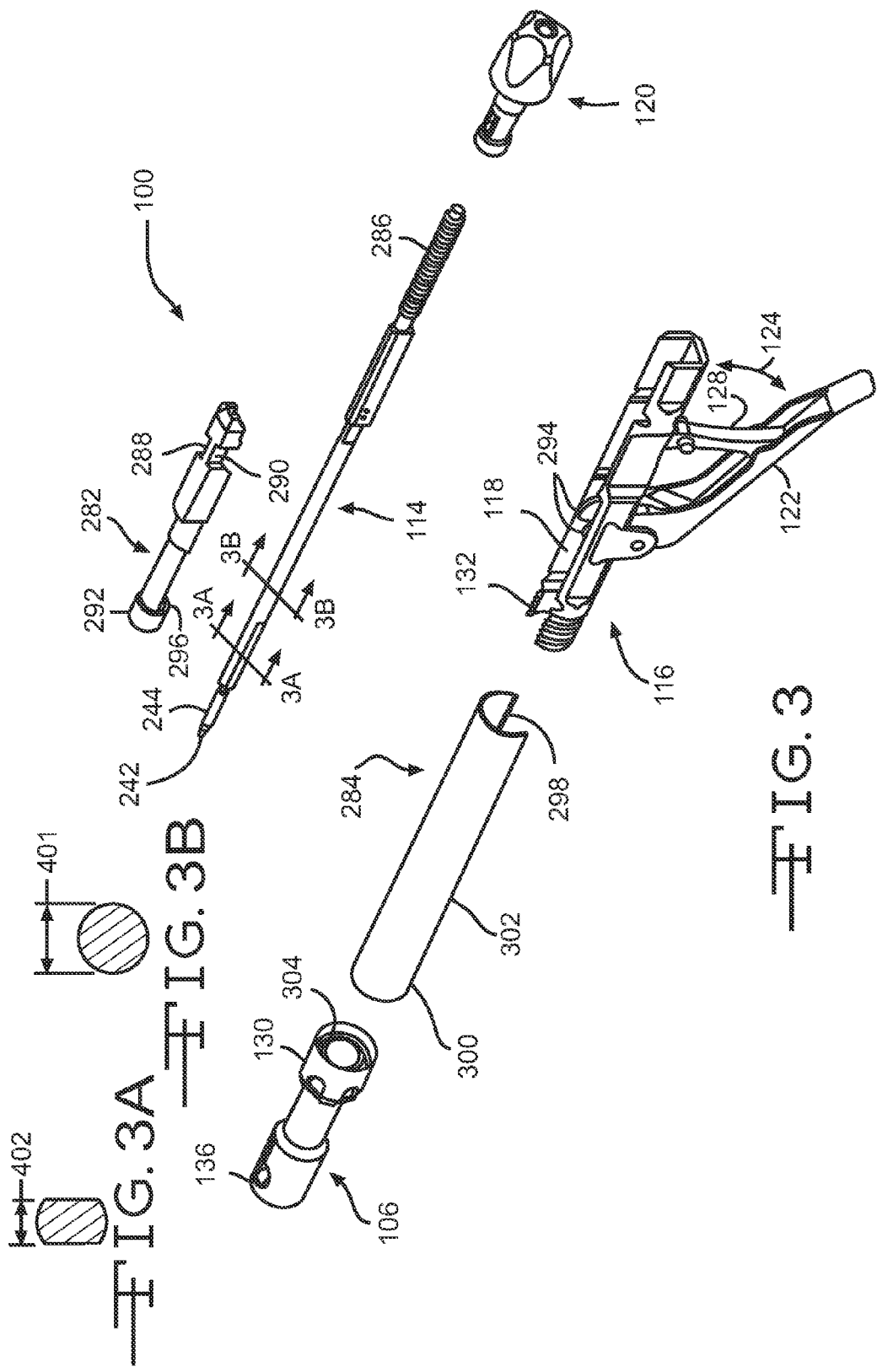
FIG. 3 illustrates an exploded perspective view of a handle and shaft assembly of the reusable circular stapling instrument of FIG. 1.

With reference to FIGS. 1-2, circular stapling instrument 100 includes an ergonomic shaft assembly 106, a stapling cartridge assembly 108 having a casing 110, and an anvil assembly 112 detachably connected to a reciprocating anvil adjusting rod 114. The stapling reload assembly 102 of the circular stapling instrument includes the stapling cartridge assembly 108 and the anvil assembly 112. As shown in FIGS. 1-3, the circular stapling instrument 100 further includes a handle 116 forming a cavity 118. An anvil control member 120 is located on the proximal end of the handle 116 and is operatively coupled with the anvil assembly 112 such that rotation of the anvil control member 120 moves the anvil assembly 112 proximally or distally, depending on the direction of rotation of the anvil control member 120. The anvil control member 120 may comprise an anvil closure knob or other type of anvil control member. The circular stapling instrument 100 includes a firing trigger 122 which is rotateable in direction 124 from the open position shown to a closed position in which the staples 104 (see FIGS. 7 and 31) are injected into tissue (see FIG. 31) and excess tissue is cut with an annular blade 126 (see FIG. 31) of the stapling reload assembly 102. A safety latch 128 is located on the firing trigger 122 and is shown in an up and engaged position which prevents operation of the firing trigger 122. When the safety latch 128 is disengaged and moved inwards and downwards in direction 128a, the firing trigger 122 is free to rotate in direction 124 from the open position to the closed position. The shaft assembly 106 extends distally from the handle 116 and detachably couples with the handle 116 at a proximal end using a connecting nut 130 that attaches to a threaded portion 132 (see FIG. 3) of handle 116. Opposed attachment members 134 (see FIG. 4) of the casing 110 detachably couple to receiving members 136 (see FIG. 3) at a distal end of the shaft assembly 106. The attachment members 134 comprise deflectable snap members and the receiving members 136 comprise apertures. In other embodiments, the attachment members 134 and the receiving members 136 may comprise any type of mating members.

As shown in FIG. 2, the casing 110 has an exterior surface 138 having a flared driver portion 140 and an outer tubular driver portion 142. Passageways 144 comprise a casing surface aperture extending from the flared driver portion 140 to the outer tubular driver portion 142. An annular staple holder 148 (see FIGS. 4-5, 7, and 31) is attached within a distal end of the casing 110 with attachment members 150 (see FIGS. 4, 7, and 31) of the staple holder 148 detachably connected to receiving members 152 (see FIGS. 4, 7, and 31) of the casing 110. The attachment members 150 comprise snap projections and the receiving members 152 comprise deflectable snaps. In other embodiments, the attachment members 150 and the receiving members 152 may each comprise any type of connectable members. The annular staple holder 148 includes an annular array of staple slots 154 (see FIGS. 4, 7, and 31) for holding and emitting the staples 104 (see FIG. 31).

As shown in FIGS. 4-7, a staple driver 156 slidably connects to the annular staple holder 148 with keys 158 (see FIG. 4) of the staple driver 156 providing an arrangement that is a detachable connection to keyways 160 (see FIG. 4) of the annular staple holder 148. The staple driver 156 movably mounts within the casing 110 with alignment slots 162 of an annular exterior driver surface 164 of the staple driver 156 moveably connected to alignment splines 166 of an annular interior casing surface 168 of the casing 110 allowing longitudinal movement of the staple driver 156 within the casing 110 while preventing rotation of the staple driver 156 within the casing 110. The exterior driver surface 164 of the staple driver 156 has a flared driver portion 170 and an outer tubular driver portion 171. The alignment slots 162 and alignment splines 166 are disposed parallel to longitudinal axis 172 and 174 of the staple driver 156 and the casing 110. In other embodiments, the casing 110 and staple driver 156 may be aligned relative to one another using any number, type, or configuration of alignment members which allow longitudinal movement.

Figure 4:
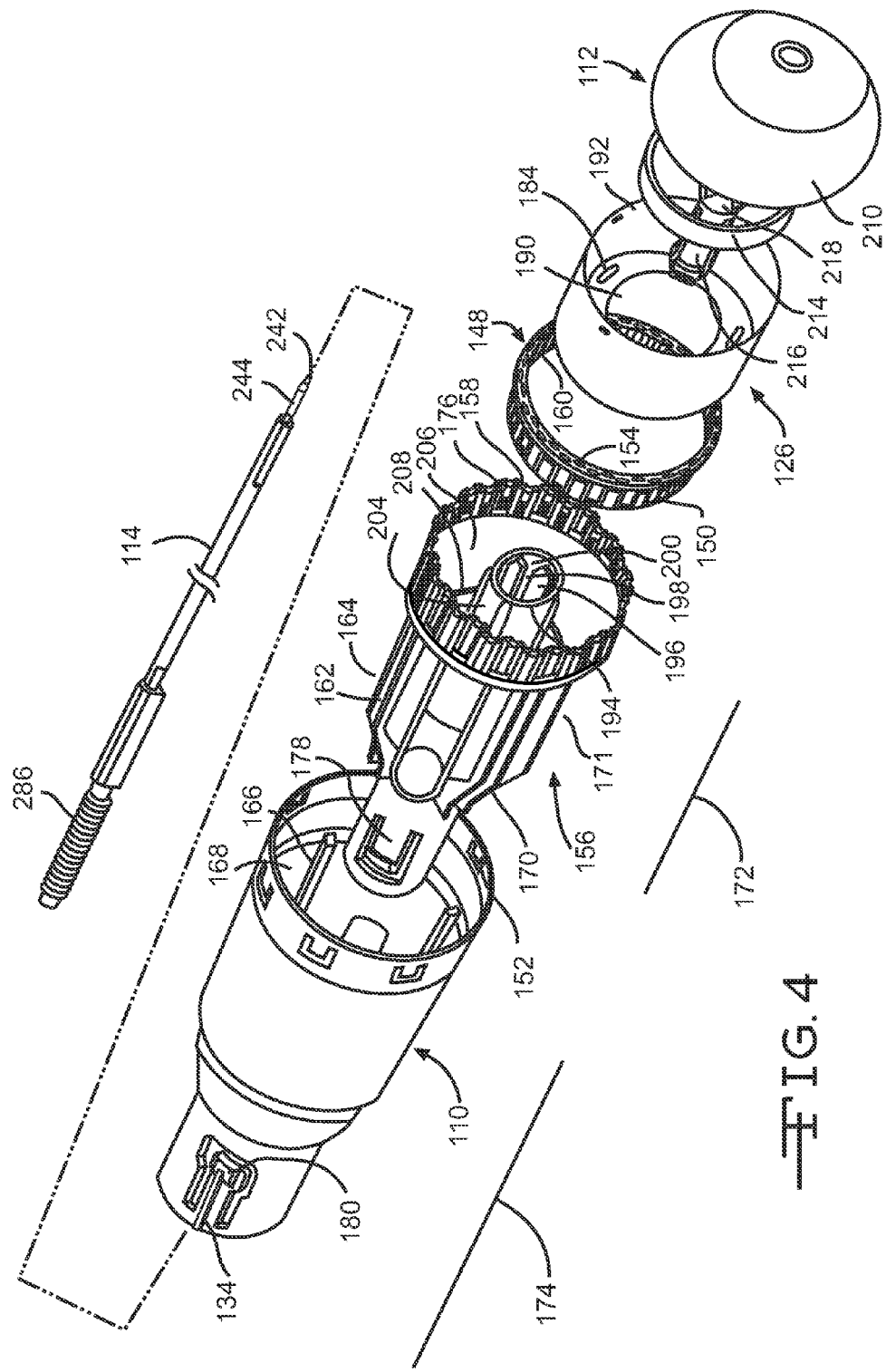
FIG. 4 illustrates an exploded perspective view of a stapling reload assembly of the reusable circular stapling instrument of FIG. 1.
Figure 5:
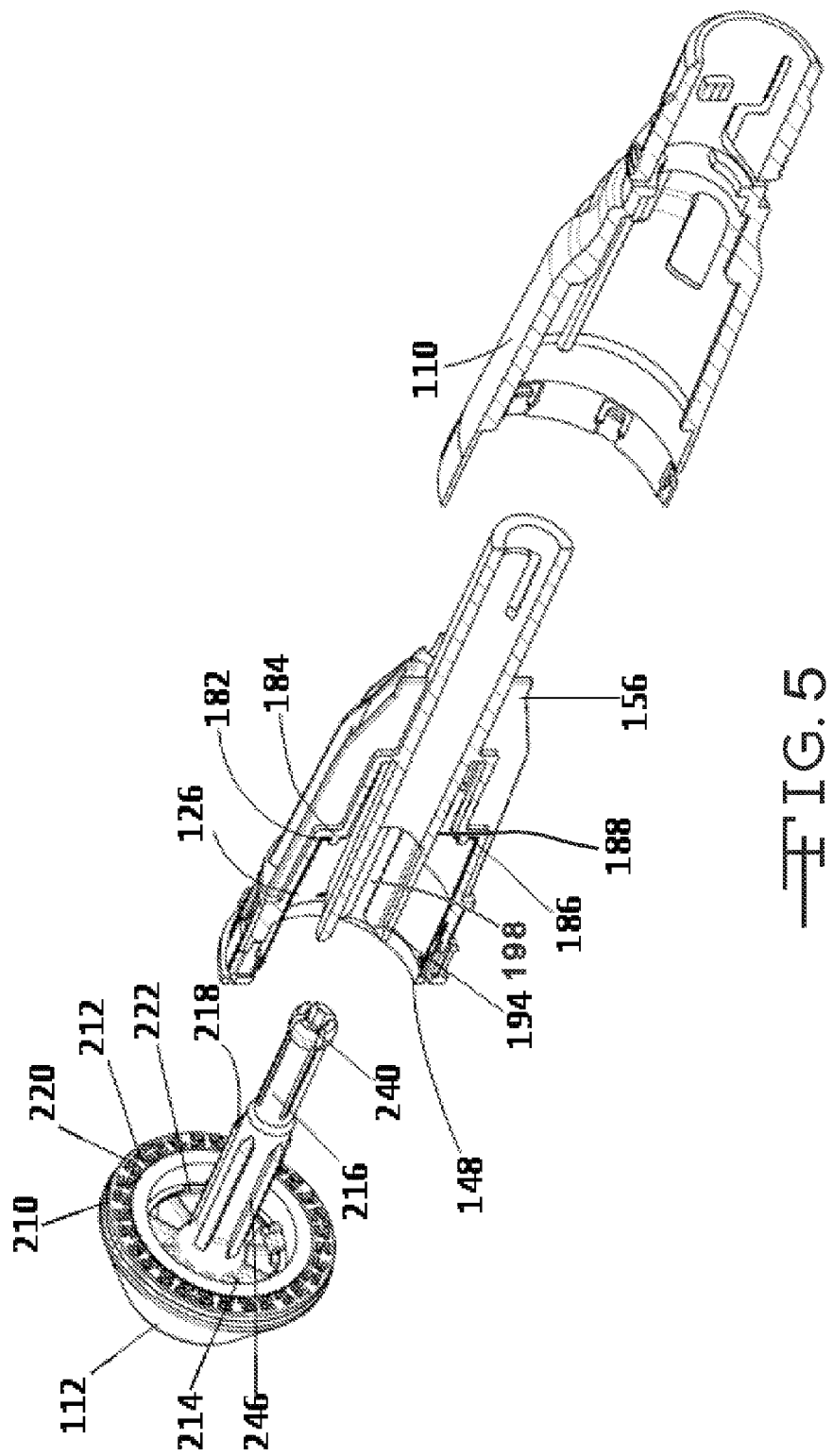
FIG. 5 illustrates a partial cross-sectional view through a stapling reload assembly of the reusable circular stapling instrument of FIG. 1 in an unassembled configuration.
Figure 7:
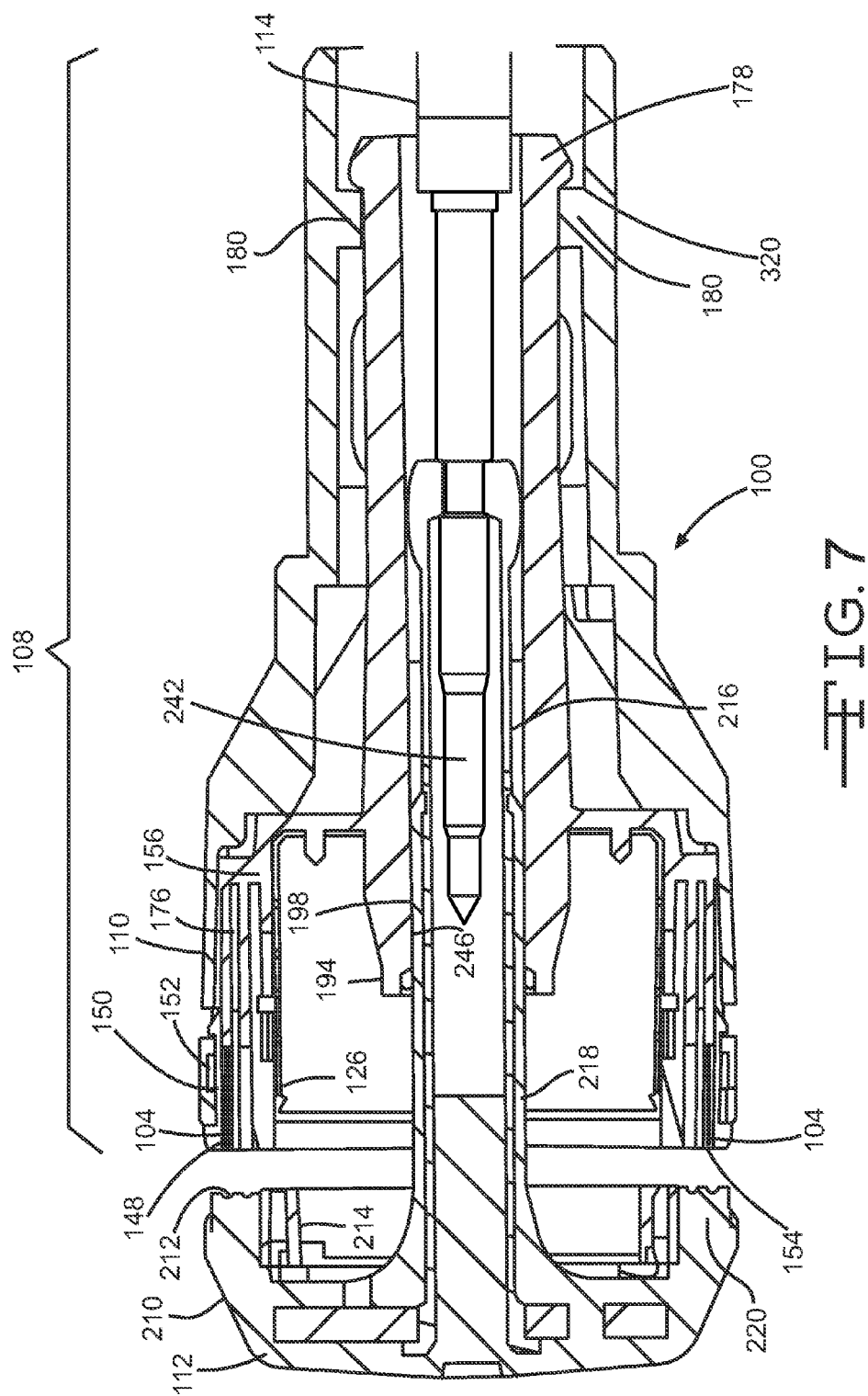
FIG. 7 illustrates the view of FIG. 6 with the anvil assembly moved to a closed position and with the annular blade still being in the pre-fired position.

The staple driver 156 has a plurality of fingers 176 that are received within the staple slots 154 within the staple holder 148. The fingers 176 are for engaging and driving a plurality of the staples 104 (see FIG. 31) from the staple slots 154 of the staple holder 148 as the staple driver 156 is moved from a pre-fired position (see FIG. 7) to a fired position (see FIG. 31) by actuation of the firing trigger 122 (see FIG. 3). As shown in FIGS. 4 and 7, flexible detent members 178 of the staple driver 156 are detachably connected to detent bumps 180 of the casing 110. This arrangement allows longitudinal movement of the staple driver 156 only when a predetermined amount of force is exerted by a firing bar 282 (see FIGS. 44-46) on the staple driver 156. When the required force is exerted the deflectable detent members 178 on the staple driver 156 bend inwards thereby disengaging from the detent bumps 180 on the casing 110 allowing the staple driver 156 to move longitudinally and distally. In other embodiments, the flexible detent member 178 and the detent bumps 180 may comprise other types of mating members.

The annular blade 126 is mounted within the distal end of the staple driver 156 and is attached by a plurality of blade mounting pins 182 (see FIGS. 5 and 31) that project through a like number of mounting holes 184 within a base 186 of the annular blade 126. The annular blade 126 has a blade opening 188 (see FIGS. 5 and 31) within the base 186. The open distal end 190 (see FIGS. 4, 29, and 31) of the annular blade 126 has a cutting edge 192. The annular blade 126 moves with the staple driver 156 when the staple driver 156 is moved distally from the pre-fired position of FIG. 7 to the fired position of FIG. 31 using the firing trigger 122 (see FIG. 3). When the firing trigger 122 is fired, the firing trigger 122 rotates in direction 124 from its position of FIGS. 38-43 to its position of FIGS. 44-46 forcing a mated firing bar 282 within the casing 110 to move in direction 392 abutting against and forcing the staple striver 156 to also move within the casing 110 in direction 392. This movement fires the staple driver 156, and its attached annular blade 126, from its pre-fired position of FIGS. 7 and 38-43 to its fired position of FIGS. 31 and 44-46. During the firing of the staple driver 156, the fingers 176 of the staple driver 156 fire the staples 104 from their pre-fired position in the staple holder 148 shown in FIG. 7 to their fired position out of the staple holder 148 shown in FIG. 31.

The reciprocating anvil adjusting rod 114 (see FIGS. 4 and 6) is located within the stapling cartridge assembly 108 and is positioned to extend through and move within an annular interior shaft 194 (see FIGS. 4 and 6) of the staple driver 156. As shown in FIGS. 3A and 3B, the cross-section of the reciprocating anvil adjusting rod 114 varies in shape and size with one portion along cross-sectional line 3A-3A being of circular shape and having a diameter 401 as shown in FIG. 3A, and another portion along cross-sectional line 3B-3B having parallel side-walls spaced apart by a distance 402, smaller than diameter 401, as shown in FIG. 3B. As shown in FIG. 4, the annular interior shaft 194 extends longitudinally within the staple driver 156 parallel to the longitudinal axis 172 of the staple driver 156. A hole 196 extends within the annular interior shaft 194. An anvil alignment surface 198 extends longitudinally along an annular interior surface 200 of the annular interior shaft 194. The anvil alignment surface 198 comprises at least one longitudinal slot. In other embodiments, the anvil alignment surface 198 may comprise any number or type of alignment surfaces in varying configurations. An exterior surface 204 of the annular interior shaft 194 is spaced apart from another annular interior surface 206 of the staple driver 156 with an annular hole 208 extending between the exterior surface 204 of the annular interior shaft 194 and the annular interior surface 206.

Figure 8:
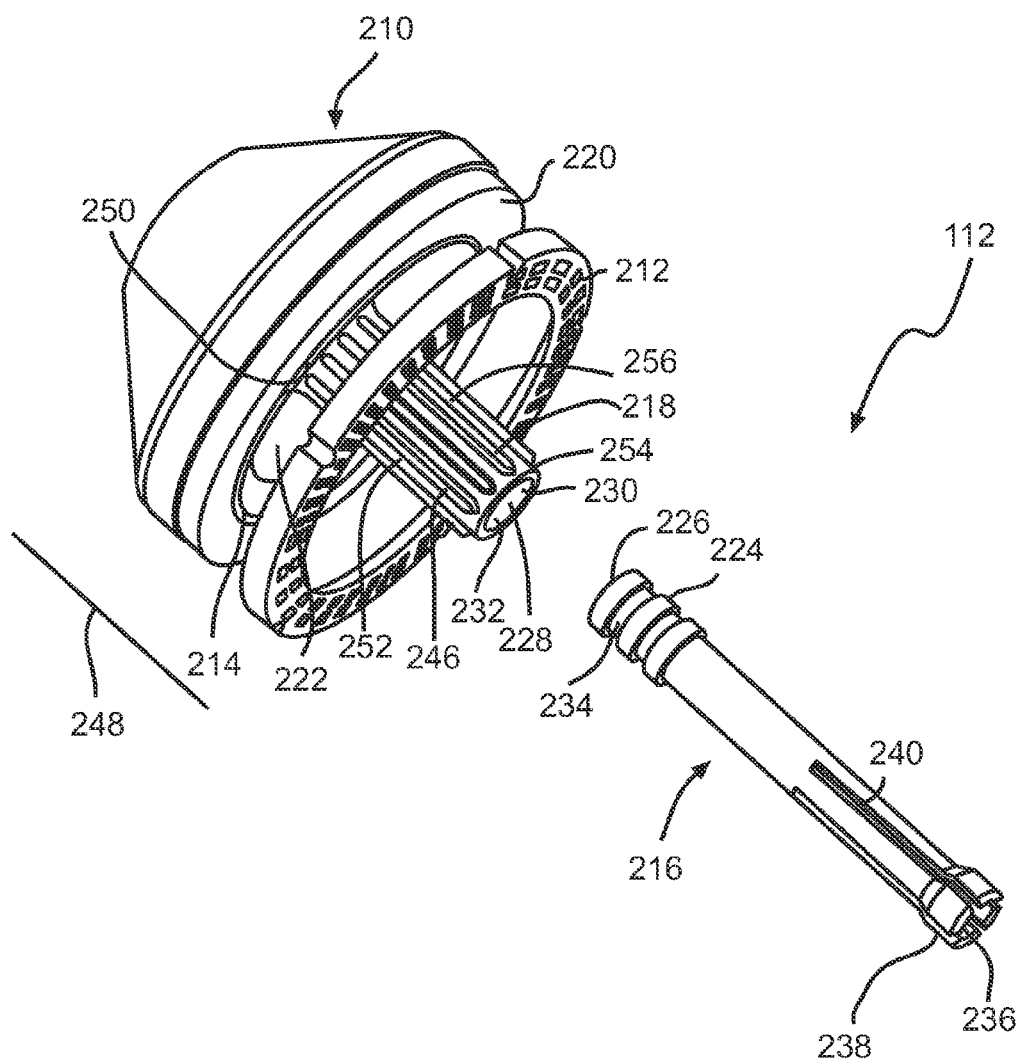
FIG. 8 illustrates an exploded perspective view of the anvil assembly of the reusable circular stapling instrument of FIG. 1.

With reference to FIGS. 1, 2, 4-7, and in particular FIG. 8 the anvil assembly 112 comprises an anvil 210, a staple forming surface 212, an annular breakaway washer 214, and a metal shaft 216. The anvil 210 is a one-piece polymeric molded part comprising an anvil shaft 218 integrally molded to an anvil base surface 220. The anvil 210 is made of a polymer comprising glass filled or carbon filled Nylon. In other embodiments, the anvil 210 may be made of similar composite materials having a tensile strength greater than 15,000 psi in order to prevent excessive bending under tissue forces.

The anvil base surface 220 is molded to the staple forming surface 212 and metal shaft 216. In other embodiments, the anvil base surface 220 may be attached to the staple forming surface 212 using varying attachment mechanisms. The staple forming surface 212 is made of sheet metal or a plate comprising stainless steel, is annular in shape, and includes staple forming pockets. In other embodiments, the staple forming surface 212 may be made of Aluminum or other materials that can withstand staple forming forces.

The annular breakaway washer 214 is press-fit within a cavity 222 of the anvil base surface 220 adjacent to the anvil base surface 220. In other embodiments, the annular breakaway washer 214 may be attached within the cavity 222 of the anvil base surface 220 using varying attachment mechanisms. The annular breakaway washer 214 is made of a plastic comprising ABS (Acrylonotrile-Butadiene-Styrene). In other embodiments, the annular breakaway washer 214 may be made of Nylon, Polyethylene or Polypropylene.

The anvil shaft 218 is molded around an exterior surface 224 of an end 226 of the metal shaft 216, with the metal shaft 216 extending into a molded hole 228 of the anvil shaft 218. The molded hole 228 of the anvil shaft 218 ends within the anvil shaft 218 and does not extend through the distal end of the anvil base surface 220. An interior surface 230 of the anvil shaft 218 comprises receiving members 232 which are molded to attachment members 234 of the exterior surface 224 of the end 226 of the metal shaft 216. The receiving members 232 comprise molded annular ribs (FIG. 38), and the attachment members 234 comprise annular grooves (FIG. 8). In other embodiments, the receiving members 232 and attachment members 234 may comprise grooves and threads, female and male members, or other types of attachment mechanisms. In still other embodiments, the anvil shaft 218 may be attached to the metal shaft 216 using varying attachment mechanisms. A proximal end channel 236 extends through the metal shaft 216. End 238 of the metal shaft 216 includes expansion slots 240 (see FIG. 2). The metal shaft 216 is made of a stainless steel. In other embodiments, the metal shaft 216 may be made of varying materials.

At the time of manufacture of the anvil assembly 112, the metal shaft 216 and the staple forming surface 212 are pre-manufactured. The pre-manufactured metal shaft 216 and the pre-manufactured staple forming surface 212 are then inserted into an injection mold. The mold is then used to form the anvil 210 within the mold causing the anvil 210 to be molded to both the pre-manufactured metal shaft 216 and to the pre-manufactured staple forming surface 212. During the molding process the anvil base surface 220 forms and is molded to the pre-manufactured staple forming surface 212, while the anvil shaft 218 forms and is molded around the end 226 of the pre-machined metal shaft 216. The annular breakaway washer 214 is then press-fit within the cavity 222 of the molded anvil base surface 220. In other embodiments, the manufacturing process may vary.

The engagement member 244 (see FIGS. 2 and 6) of the reciprocating anvil adjusting rod 114 detachably couples within the proximal end channel 236 of the metal shaft 216 using a snap-fit coupling. This arrangement operatively couples the metal shaft 216 and the attached anvil 210 to the anvil control member 120 of the reciprocating anvil adjusting rod 114. In other embodiments, the engagement member 244 of the reciprocating anvil adjusting rod 114 may be attached to the metal shaft 216 using other attachment mechanisms. The expansion slots 240 allow end 238 of the metal shaft 216 to expand during the coupling to the engagement member 244 of the reciprocating anvil adjusting rod 114. After using the circular stapling instrument 100 on a patient, the entire anvil assembly 112 is disposed of. During a subsequent procedure, a new stapling reload assembly 102, which includes a new anvil assembly 112, is used.

Figure 12:
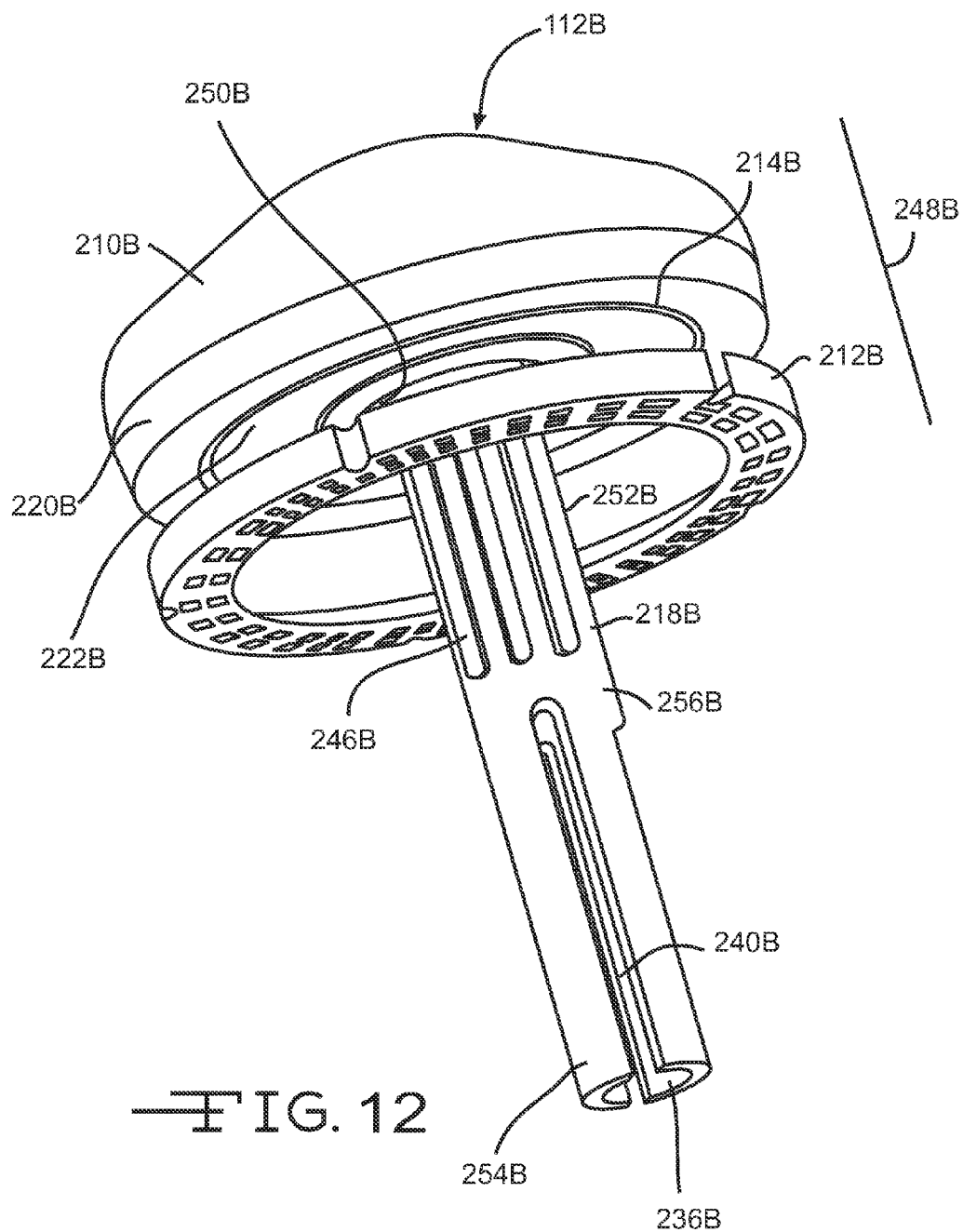
FIG. 12 illustrates an exploded perspective view of an additional embodiment of an anvil assembly.

As shown in FIG. 8, the anvil shaft 218 includes an alignment surface 246 formed at the time of molding the anvil 210. The alignment surface 246 comprises at least one spline disposed parallel to a longitudinal axis 248 of the anvil shaft 218. The alignment surface 246 extends from a top portion 250 of the anvil shaft 218, along an exterior annular surface 252 of the anvil shaft 218, to a bottom portion 254 of the anvil shaft 218. The metal shaft 216 of the anvil assembly 112 does not contain an alignment surface. In other embodiments, the alignment surface 246 may comprise any number or type of alignment surfaces in varying configurations. For instance, as shown in FIG. 12, in an embodiment in which the anvil assembly 112 only includes the anvil shaft 218 without the metal shaft 216 being attached to the anvil assembly 112, the alignment surface 246 may extend from a top portion 250 of the anvil shaft 218, along the exterior annular surface 252 of the anvil shaft 218, and stop at a middle portion 256 of the anvil shaft 218 without extending to the bottom portion 254 of the anvil shaft 218.

The anvil assembly 112 is movable from an open position (see FIG. 6) in which the staple forming surface 212 is disposed away from the casing 110 for the reception of tissue, to a closed position (see FIG. 7) in which the staple forming surface 212 is disposed adjacent to the casing 110 of the stapling cartridge assembly 108 clamping tissue between the staple holder 148 and the staple forming surface 212 prior to firing the staple driver 156 to staple and cut the clamped tissue. This is due to the tip 242 (see FIGS. 2 and 6) of the engagement member 244 of the reciprocating anvil adjusting rod 114 extending within the annular interior shaft 194 of the staple driver 156 and being connected within the channel 236 of proximal end 238 of the metal shaft 216 of the anvil assembly 112. As a result, due to movement of the connected reciprocating anvil adjusting rod 114, the anvil shaft 218, which is connected to the metal shaft 216, is moveably disposed within the annular interior shaft 194 of the staple driver 156 allowing movement of the staple forming surface 212 of the anvil assembly 112 relative to the staple driver 156 and casing 110.

Figure 6:
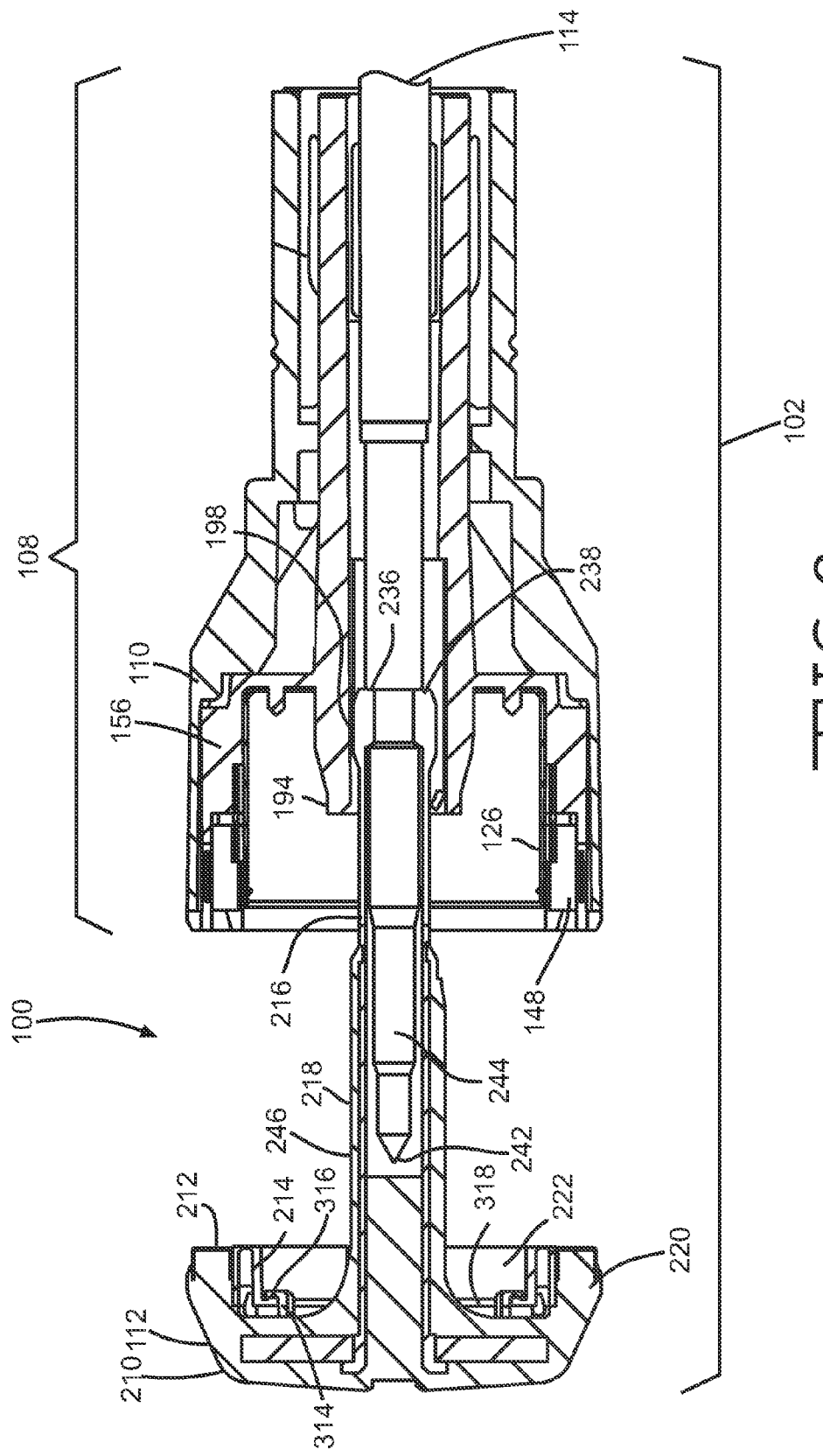
FIG. 6 illustrates a cross-section view through a stapling reload assembly of the reusable circular stapling instrument of FIG. 1 in an assembled configuration with an anvil assembly in an open position and an annular blade in a pre-fired position.

The alignment surface 246 (see FIG. 8) of the anvil shaft 218 is configured to mate with the anvil alignment surface 198 (see FIG. 4) of the staple driver 156 to rotationally align the staple forming surface 212 with the staple holder 148 when the anvil base surface 220 is in the closed position (see FIG. 7) adjacent to the stapling cartridge assembly 108. Initially, as shown in FIG. 6, as the reciprocating anvil adjusting rod 114 moves the metal shaft 216 and the attached anvil shaft 218, thereby moving the anvil base surface 220 from the open position shown in FIG. 6 towards the closed position shown in FIG. 7, the alignment surface 246 (see FIG. 8) of the anvil shaft 218 is not mated with the anvil alignment surface 198 (see FIG. 4) of the annular interior shaft 194 of the staple driver 156 because the anvil alignment surface 198 will only be disposed adjacent to the metal shaft 216 which lacks an alignment surface. During this time, the staple forming surface 212 will not be rotationally aligned with the staple holder 148. However, as shown in FIG. 7, when the alignment surface 246 of the anvil shaft 218 reaches the annular interior shaft 194 of the staple driver 156, the alignment surface 246 will mate with the anvil alignment surface 198 of the annular interior shaft 194 rotationally aligning the staple forming surface 212 with the staple holder 148 as the anvil base surface 220 moves into the closed position adjacent to the stapling cartridge assembly 108. Referring to FIG. 33A, the markings 120A adjacent the anvil control member 120 visually indicate the gap distance between the staple forming surface 212 of the anvil 112 (see FIG. 7) and the staple guide 148 (see FIG. 7) providing feedback to the user on the compressed tissue thickness. When the device is near full closure the proximal end of the reciprocating anvil adjusting rod 114 pops through the hole 120F in the anvil control member 120.

Figure 31:
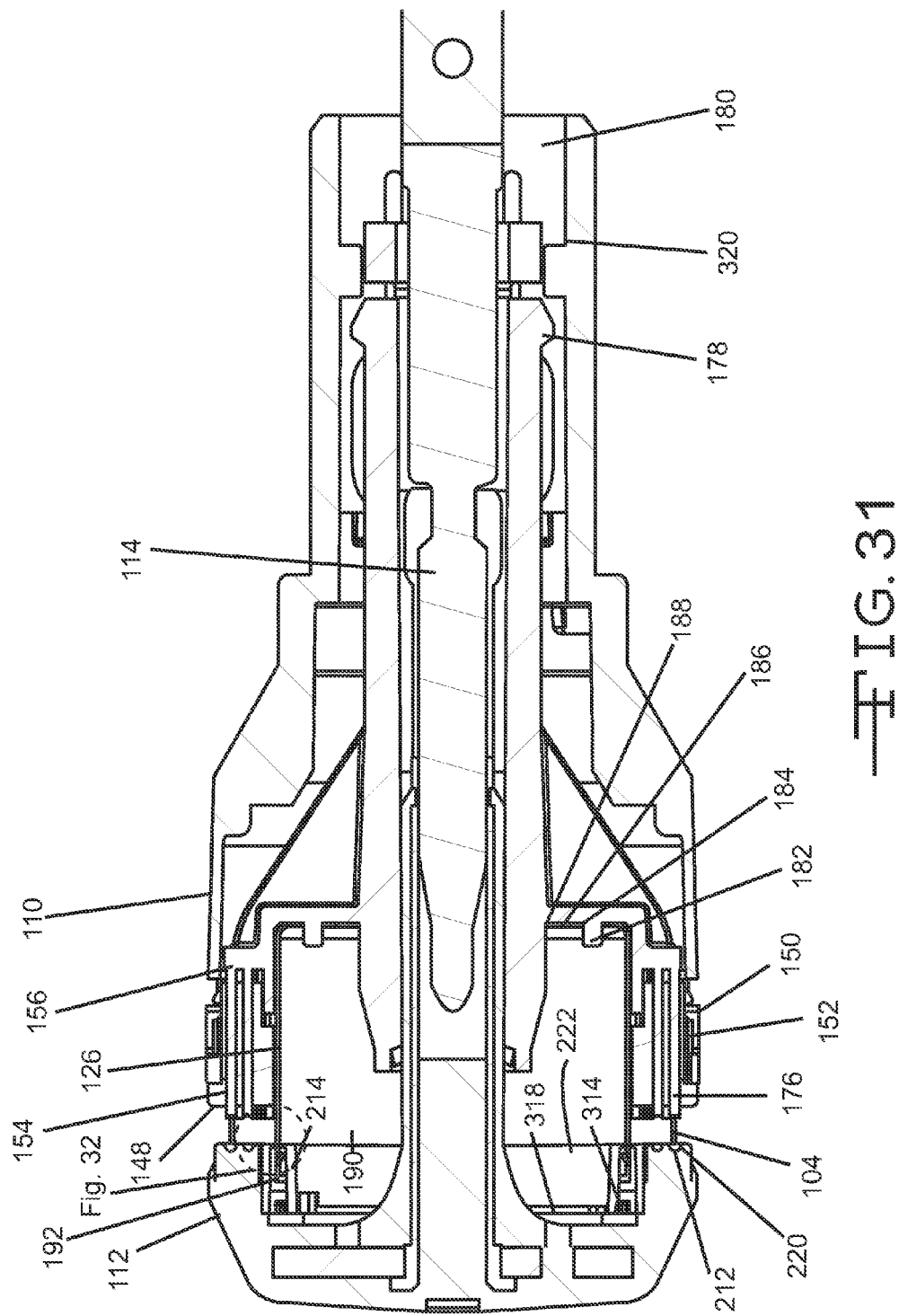
FIG. 31 illustrates the view of FIG. 7 with the annular blade moved to the fired position cutting an annular breakaway washer while the anvil assembly is in the closed position.

When the anvil assembly 112 is in the closed position of FIG. 7 and the circular stapling instrument is fired 100, moving the staple driver 156 from its pre-fired position within the casing 110 shown in FIG. 7 to its fired position shown in FIG. 31, the fingers 176 of the staple driver 156 drive the staples 104 from the staple slots 154 of the staple holder 148 against the staple forming surface 212 of the anvil assembly 112. The staple forming surface 212 form the ejected staples 104 into a closed staple shape thereby stapling portions of tissue together. Simultaneously, the staple driver 156 drives the annular blade 126 into the compressed tissue captured between the staple forming surface 212 on the anvil 210 and the surface of the staple guide 148, thereby cutting the tissue against the breakaway washer 214 of the anvil assembly 112.

Figure 9:
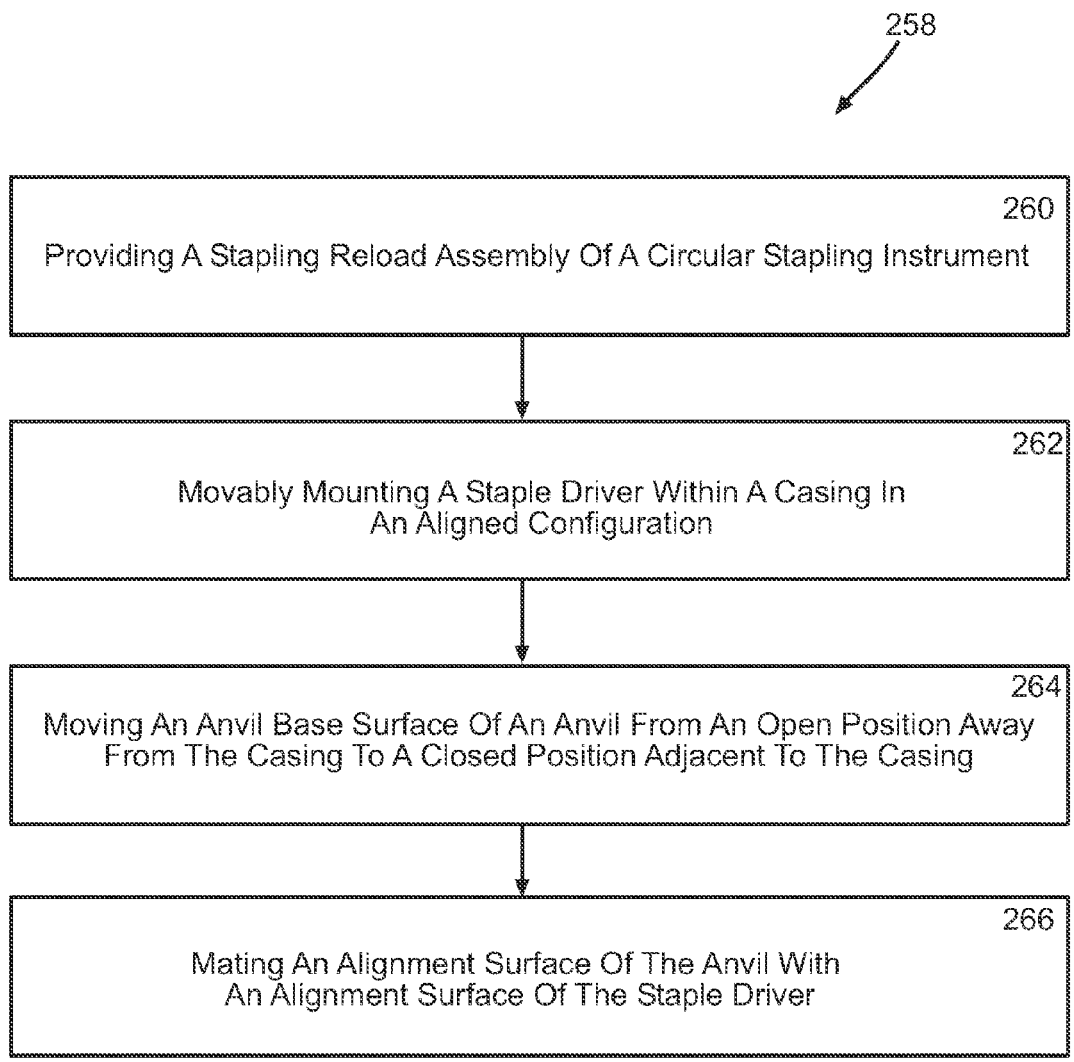
FIG. 9 illustrates a flowchart of one embodiment of a method of aligning a stapling reload assembly of a circular stapling instrument.

FIG. 9 illustrates a flowchart 258 showing one embodiment of a method of aligning a stapling reload assembly of a circular stapling instrument. In step 260, a stapling reload assembly of a circular stapling instrument is provided. The provided circular stapling instrument includes a casing, a staple holder attached to the casing, a staple driver, an annular blade, and an anvil. In step 262, the staple driver is movably mounted within the casing in an aligned configuration, and attachment members of the staple driver are connected to receiving members of the casing preventing the staple driver from moving past a certain point within the casing until a predetermined amount of force is applied on the staple driver by a firing bar. In step 264, an anvil base surface of the anvil is moved from an open position away from the casing, in which a staple forming surface of the anvil is not rotationally aligned with the staple holder attached to the casing, towards a closed position adjacent to the casing. In step 266, an alignment surface of the anvil is mated with an anvil alignment surface of the staple driver to rotationally align the staple forming surface of the anvil with the staple holder when the anvil base surface is in the closed position adjacent to the casing. The alignment surface of the anvil comprises at least one spline, and the anvil alignment surface of the staple driver comprises at least one slot. In other embodiments, the number, type, and configuration of the alignment surface of the anvil and the anvil alignment surface of the driver may vary.

One or more embodiments of the disclosure may reduce one or more problems associated with alignment in previous surgical circular stapling instruments. For instance, use of one or more embodiments of the disclosure may provide proper alignment directly between the anvil and the staple driver instead of requiring a first alignment between the anvil and the casing, and a second alignment between the staple driver and the casing as is done in current devices. This method of directly aligning the driver and the anvil reduces the potential of alignment variation and results in improved staple form.

Figure 10:
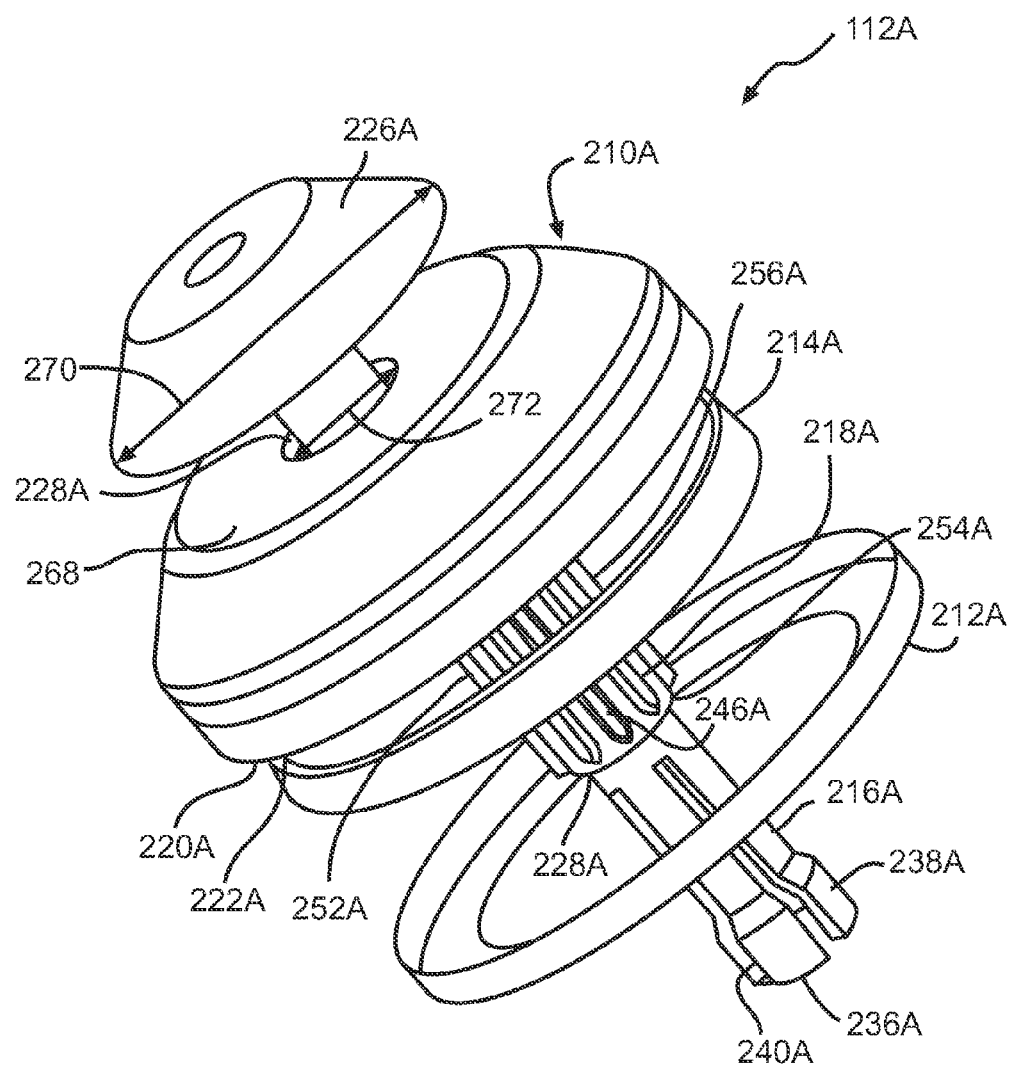
FIG. 10 illustrates an exploded perspective view of another embodiment of an anvil assembly.

FIG. 10 illustrates an exploded view of another embodiment of an anvil assembly 112A comprising an anvil 210A, a staple forming surface 212A, an annular breakaway washer 214A, and a metal shaft 216A. The anvil 210A is a one-piece, polymer, molded part comprising an anvil shaft 218A molded to an anvil base surface 220A. The anvil 210A is made of a polymer comprising glass filled or carbon filled Nylon. In other embodiments, the anvil 210A may be made of similar composite materials having a tensile strength greater than 15,000 psi in order to prevent excessive bending under tissue forces.

The metal shaft 216A extends through a molded hole 228A which extends through both the anvil shaft 218A and the anvil base surface 220A. One end 226A of the metal shaft 216A extends out of the molded hole 228A and abuts against a top portion 268 of the anvil base surface 220A. End 226A of the metal shaft 216A has a larger diameter 270 than the diameter 272 of the molded hole 228A. The other end 238A of the metal shaft 216A extends out of the molded hole 228A of the anvil shaft 218A. The metal shaft 216A comprises attachment members (hidden from sight) which attach to receiving members (hidden from sight) of the anvil shaft 218A. The attachment members comprise threads and the receiving members comprise grooves. In other embodiments, the attachment members and receiving members may comprise male and female members, or other types of attachment mechanisms. In still other embodiments, the metal shaft 216A may be attached to the anvil shaft 218A using varying attachment mechanisms. A channel 236A extends within proximal end 238A of the metal shaft 216A. End 238A of the metal shaft 216A also includes expansion slots 240A. The metal shaft 216A is made of a metal comprising heat-treated stainless steel. In other embodiments, the metal shaft 216A may be made of other steels.

The anvil base surface 220A is molded to the staple forming surface 212A. In other embodiments, the anvil base surface 220A may be attached to the staple forming surface 212A using varying attachment mechanisms. The staple forming surface 212A is made of a sheet metal comprising austenitic stainless steel, is annular in shape, and includes staple forming pockets. In other embodiments, the staple forming surface 212A may be made of other metals, stainless steels, Aluminum, sheet, or plate.

The annular breakaway washer 214A is press-fit within a cavity 222A of the anvil base surface 220A adjacent to the anvil base surface 220A. In other embodiments, the annular breakaway washer 214A may be attached within the cavity 222A of the anvil base surface 220A using varying attachment mechanisms. The annular breakaway washer 214A is made of a plastic comprising ABS (Acrylonotrile-Butadiene-Styrene). In other embodiments, the annular breakaway washer 214A may be made of Nylon, Polyethylene, or Polypropylene.

At the time of manufacture of the anvil assembly 112A, the staple forming surface 212A is pre-manufactured. The pre-manufactured staple forming surface 212A is then inserted into an injection mold. The mold is then used to form the anvil 210A within the mold causing the anvil 210A to be molded to the staple forming surface 212A. During the molding process the anvil base surface 220A forms and is molded to the staple forming surface 212A. The annular breakaway washer 214A is then press-fit within the cavity 222A of the molded anvil base surface 220A. After molding the anvil base surface 220A, end 238A of a pre-manufactured metal shaft 216A is extended into the molded hole 228A in the anvil base surface 220A and out of the molded hole 228A in the anvil shaft 218A so that end 226A of the metal shaft 216A abuts against the top portion 268 of the anvil base surface 220A. This step can be performed by the user prior to use. The metal shaft 216A is detachably connected to the anvil shaft 218A due to the attachment members (hidden from view) of the metal shaft 216A mating with the receiving members (hidden from view) of the anvil shaft 218A as end 238A of the pre-manufactured metal shaft 216A is extended into and out of the molded hole 228A in the anvil 210A. In other embodiments, the manufacturing process may vary.

Figure 11:
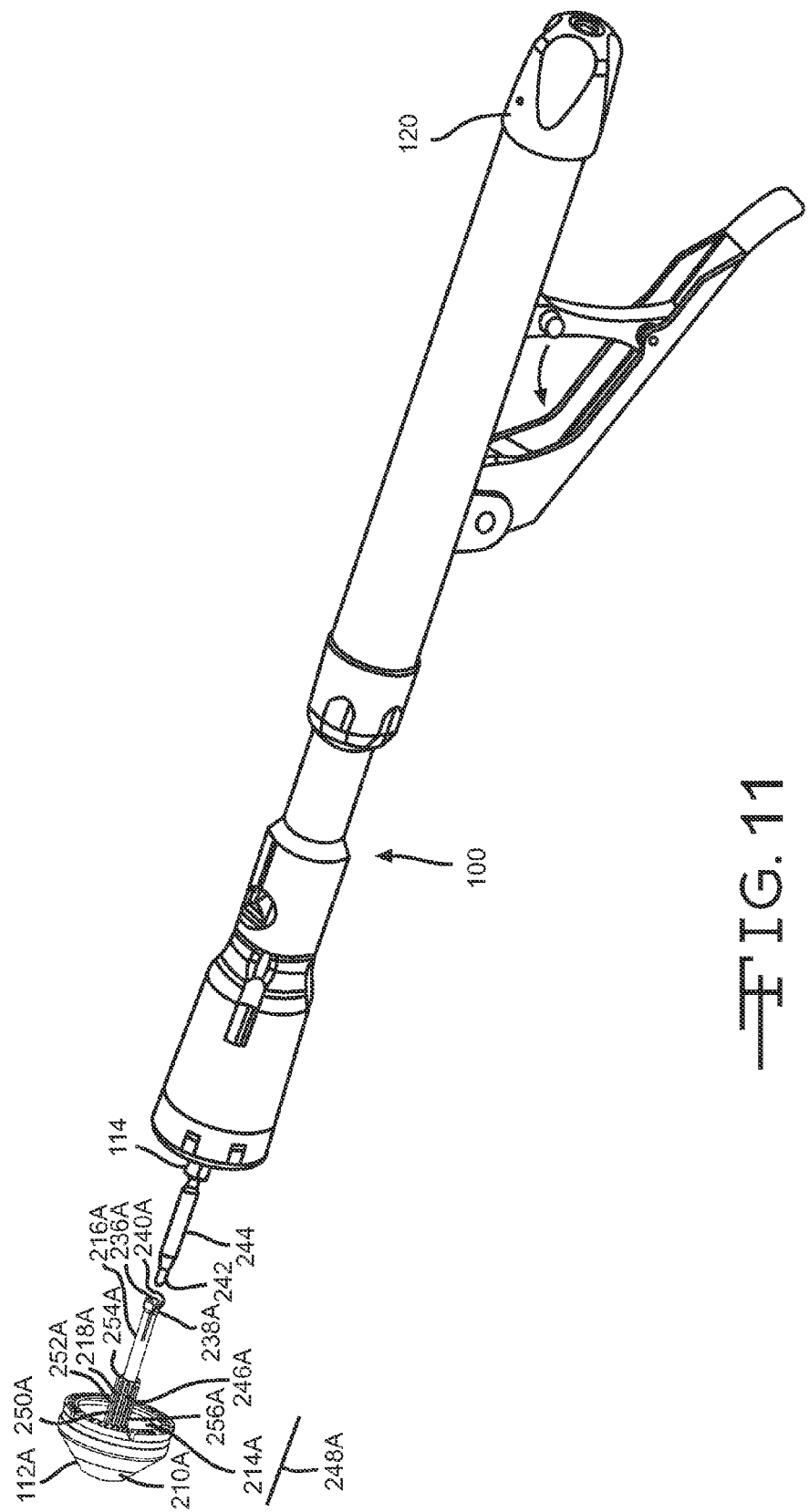
FIG. 11 illustrates a perspective view of the reusable circular stapling instrument of FIG. 1 replacing the anvil assembly with the anvil assembly of FIG. 10 separated from the remainder of the reusable circular stapling instrument.

As shown in FIG. 11, the engagement member 244 of the reciprocating anvil adjusting rod 114 detachably couples within the proximal end channel 236A of the metal shaft 216A using a snap-fit coupling operatively coupling the metal shaft 216A and the attached anvil 210A to the anvil control member 120 through the reciprocating anvil adjusting rod 114. In other embodiments, the engagement member 244 of the reciprocating anvil adjusting rod 114 may be attached to the metal shaft 216A using other attachment mechanisms. The expansion slots 240A allow end 238A of the metal shaft 216A to expand during the coupling to the engagement member 244 of the reciprocating anvil adjusting rod 114. After using the circular stapling instrument 100 on a patient, the metal shaft 216A may be removed from the anvil 210A by detaching the attachment members (hidden from sight) of the metal shaft 216A from the receiving members (hidden from sight) of the anvil shaft 218A, the anvil 210A may be disposed of, the metal shaft 216A may be sterilized, and the metal shaft 216A may be attached to a new anvil using the same above-described process to allow the metal shaft 216A to be reused on another patient in combination with the new anvil and new stapling cartridge assembly.

As shown in FIGS. 10-11, the anvil shaft 210A includes an alignment surface 246A formed at the time of molding the anvil 210A due to the mold. The alignment surface 246A comprises at least one spline disposed parallel to a longitudinal axis 248A of the anvil shaft 218A. The alignment surface 246A extends from a top portion 250A of the anvil shaft 218A, along an exterior annular surface 252A of the anvil shaft 218A, to a bottom portion 254A of the anvil shaft 218A. The metal shaft 216A of the anvil assembly 112A does not contain an alignment surface. In other embodiments, the alignment surface 246A may comprise any number or type of alignment surfaces in varying configurations.

FIG. 12 illustrates an exploded view of another embodiment of an anvil assembly 112B comprising an anvil 210B, a staple forming surface 212B, and an annular breakaway washer 214B. The anvil 210B is a one-piece, polymer, molded part comprising an anvil shaft 218B molded to an anvil base surface 220B. The anvil 210B is made of a polymer comprising glass filled or carbon filled Nylon. In other embodiments, the anvil 210B may be made of similar composite materials having a tensile strength greater than 15,000 psi in order to prevent excessive bending under tissue forces. A proximal end channel 236B extends within the anvil shaft 218B. Anvil shaft 218B includes expansion slots 240B.

The anvil base surface 220B is molded to the staple forming surface 212B. In other embodiments, the anvil base surface 220B may be attached to the staple forming surface 212B using varying attachment mechanisms. The staple forming surface 212B is made of a metal comprising austenitic stainless steel, is annular in shape, and includes staple forming pockets. In other embodiments, the staple forming surface 212B may be made of other metals, stainless steels, Aluminum, sheet, or plate.

The annular breakaway washer 214B is press-fit within a cavity 222B of the anvil base surface 220B adjacent to the anvil base surface 220B. In other embodiments, the annular breakaway washer 214B may be attached within the cavity 222B of the anvil base surface 220B using varying attachment mechanisms. The annular breakaway washer 214B is made of a plastic comprising ABS (Acrylonotrile-Butadiene-Styrene). In other embodiments, the annular breakaway washer 214B may be made of varying materials.

At the time of manufacture of the anvil assembly 112B, the staple forming surface 212B is pre-manufactured. The pre-manufactured staple forming surface 212B is then inserted into an injection mold. The mold is then used to form the anvil 210B within the mold causing the anvil 210B to be molded to the staple forming surface 212B. During the molding process the anvil base surface 220B forms and is molded to the staple forming surface 212B. At the same time the anvil shaft 218B, including the anvil rod attachment portion, is integrally molded to the anvil base surface 220B. The annular breakaway washer 214B is then press-fit within the cavity 222B of the molded anvil base surface 220B. In other embodiments, the manufacturing process may vary.

Figure 13:
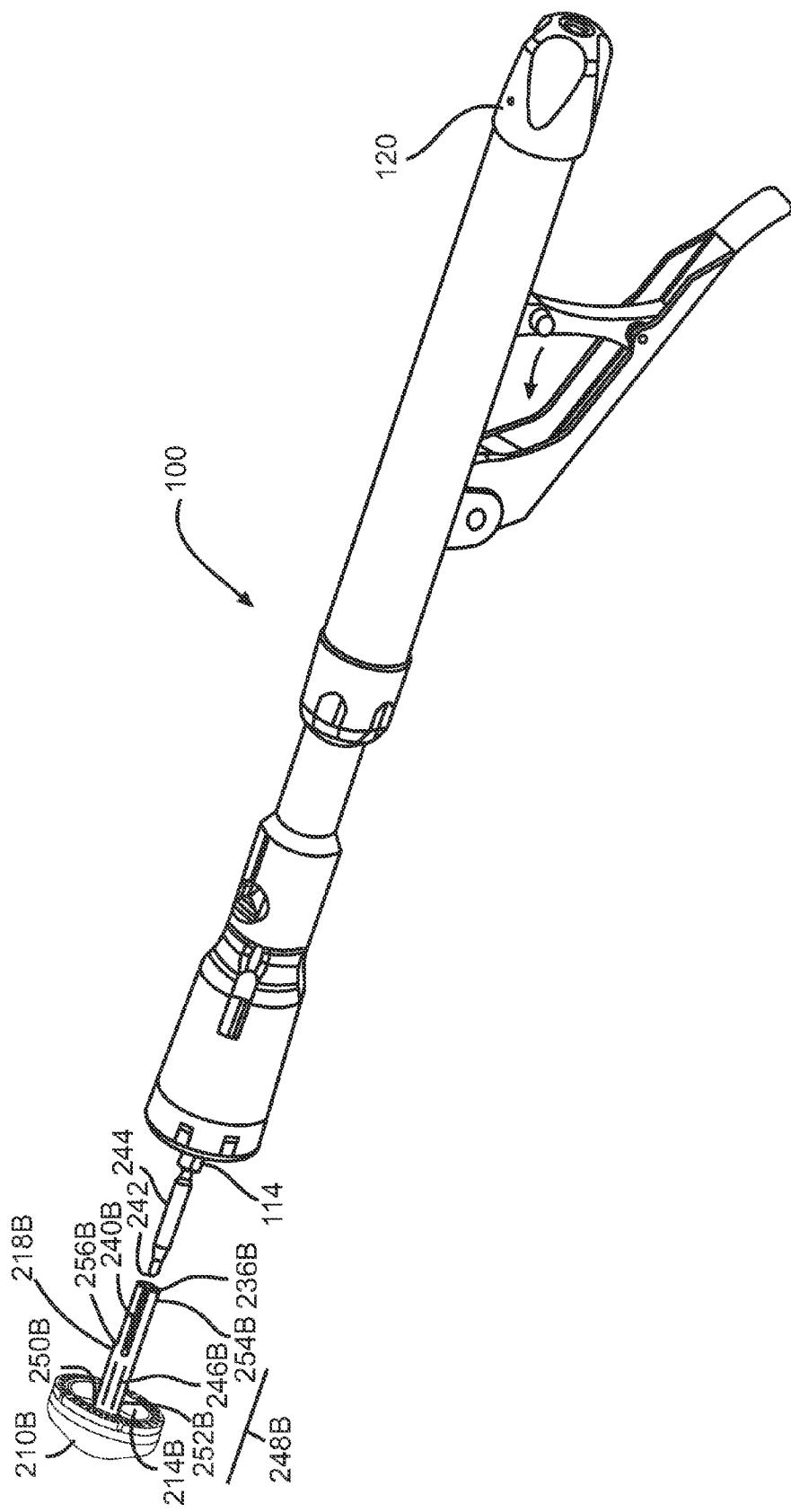
FIG. 13 illustrates a perspective view of the reusable circular stapling instrument of FIG. 1 replacing the anvil assembly with the anvil assembly of FIG. 12 separated from the remainder of the reusable circular stapling instrument.

As shown in FIG. 13, the engagement member 244 of the reciprocating anvil adjusting rod 114 detachably couples within the proximal end channel 236B of the anvil shaft 218B using a snap-fit coupling operatively coupling the anvil shaft 218B of the anvil 210B to the anvil control member 120 through the reciprocating anvil adjusting rod 114. In other embodiments, the engagement member 244 of the reciprocating anvil adjusting rod 114 may be attached to the anvil shaft 218B using other attachment mechanisms. The expansion slots 240B allow the anvil shaft 218B to expand during the coupling to the engagement member 244 of the reciprocating anvil adjusting rod 114. After using the circular stapling instrument 100 on a patient, the anvil 210B may be disposed of, and a new anvil may be used with the circular stapling instrument 100 to do another procedure on a different patient.

As shown in FIGS. 12-13, the anvil shaft 218B includes an alignment surface 246B formed at the time of molding the anvil 210B. The alignment surface 246B comprises at least one spline disposed parallel to a longitudinal axis 248B of the anvil shaft 218B. The alignment surface 246B extends from a top portion 250B of the anvil shaft 218B, along an exterior annular surface 252B of the anvil shaft 218B, and stops at a middle portion 256B of the anvil shaft 218A without extending to the bottom portion 254B of the anvil shaft 218A. In other embodiments, the alignment surface 246B may comprise any number or type of alignment surfaces in varying configurations.

Figure 14:
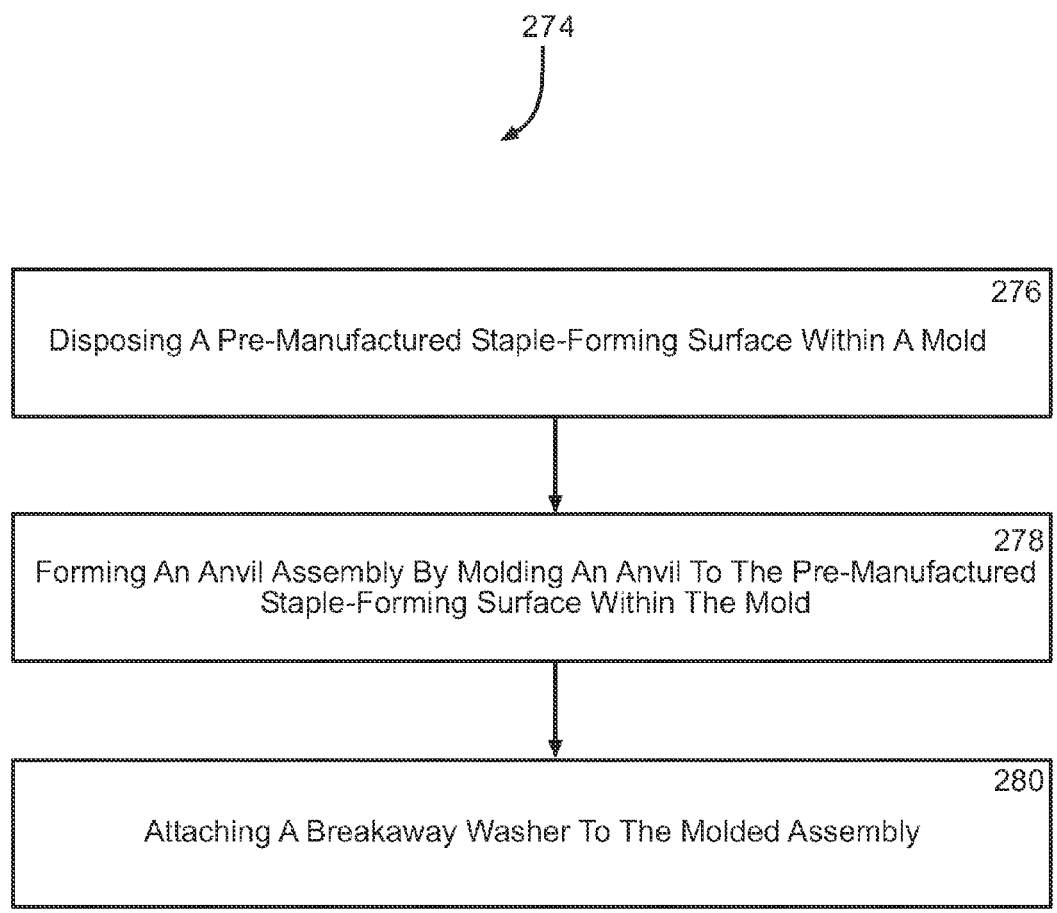
FIG. 14 illustrate a flowchart showing one embodiment of a method of manufacturing an anvil assembly.

FIG. 14 illustrates a flowchart 274 showing one embodiment of a method of manufacturing an anvil assembly. In step 276, a pre-manufactured staple-forming surface, which may be made of metal or other material, is disposed within a mold. In step 278, the anvil assembly is formed by molding an anvil to the pre-manufactured staple-forming surface within the mold, with the anvil molded to have an anvil shaft extending from an anvil base surface. The anvil may be molded to be one-piece from a polymer such as glass filled or carbon filled Nylon. In other embodiments, the anvil may be molded out of other materials. In one embodiment, step 278 may further include molding the anvil shaft to have at least one alignment surface comprising an alignment spline or another type of alignment surface. In another embodiment, step 278 may further include molding the anvil assembly so that the anvil shaft is molded to a pre-manufactured shaft, which may be made of metal or other materials, disposed within the mold during step 276. In an additional embodiment, in a subsequent step, a pre-manufactured shaft, which may be made of metal or other materials, may be attached to the anvil shaft of the molded anvil assembly after the anvil is molded. In step 280, a breakaway washer is attached, using press-fitting or other attachment mechanisms, to the anvil base surface of the molded anvil assembly. The breakaway washer may be annular or in another shape, may be made of a plastic comprising ABS (Acrylonotrile-Butadiene-Styrene), or may be made of other types of materials. In other embodiments, one or more steps of the method may vary.

One or more embodiments of the disclosure may reduce one or more problems associated with previous anvil assemblies. For instance, use of one or more embodiments of the disclosure may provide an anvil assembly which may be manufactured at one-third the cost of current anvil assemblies.

As shown in FIGS. 1-3, the circular stapling instrument 100 includes handle 116, reciprocating anvil adjusting rod 114, firing bar 282, carrier cover 284, shaft assembly 106 detachably coupled with the handle 116, stapling cartridge assembly 108, and anvil assembly 112 which is detachably coupled with the reciprocating anvil adjusting rod 114. The handle 116 forms a cavity 118 which receives the firing bar 282 and the reciprocating anvil adjusting rod 114. The reciprocating anvil adjusting rod 114 has an engagement member 244 at a tip 242 of the reciprocating anvil adjusting rod 114 and a threaded adjustment member 286 which is detachably coupled with the anvil control member 120 at a proximal end of the reciprocating anvil adjusting rod 114.

The firing bar 282 is used to stabilize and secure the reciprocating anvil adjusting rod 114 within the handle 116. Firing bar 282 forms a pair of engagement grooves 288 and 290 and has an engagement shaft 292 at a distal end of the firing bar 282. Engagement grooves 288 and 290 are preferably formed on opposing sides of firing bar 282. Firing trigger 122 includes an upper end 294 which engages the engagement grooves 288 and 290 and detachably secures the firing bar 282 and the reciprocating anvil adjusting rod 114 within the cavity 118 of the handle 116. Alternatively, engagement grooves 288 and 290 may be replaced with any detachable coupling, as described herein. Preferably, when the firing bar 282 and the reciprocating anvil adjusting rod 114 are placed within the cavity 118, portions of the upper end 294 of the firing trigger 122 each extend into one of the engagement grooves 288 and 290, detachably securing both the firing bar 282 and the reciprocating anvil adjusting rod 114 in the cavity 118. By detachably securing both the firing bar 282 and the reciprocating anvil adjusting rod 114 in the cavity 118, the engagement grooves 288 and 290 and the upper end 294 of the firing trigger 122 allow for both the firing bar 282 and the reciprocating anvil adjusting rod 114 to be easily placed into and removed from the cavity 118 allowing them to be easily serviced or replaced. The design of the cavity 118 and the features of components described above are such that they allow clear visualization by the user as they are placed in the correct location and orientation. This arrangement also prevents the user from incorrectly assembling the device.

The engagement shaft 292 forms an opening 296 through which the tip 242 and the engagement member 244 of the reciprocating anvil adjusting rod 114 are received. Receiving the reciprocating anvil adjusting rod 114 through the opening 296 of the engagement shaft 292 helps to center the reciprocating anvil adjusting rod 114 within the handle 116 and align the reciprocating anvil adjusting rod 114 within the stapling cartridge assembly 108. The stapling cartridge assembly 108 (see FIGS. 1 and 2) detachably couples with a distal end of the shaft assembly 106 (see FIG. 3). The tip 242 of the engagement member 244 of the reciprocating anvil adjusting rod 114 extends within and through the casing 110 (see FIG. 2) and detachably couples to the proximal end channel 236 (see FIG. 2) of the metal shaft 216 of the anvil assembly 112 using a snap-fit coupling.

Referring to FIG. 3, carrier cover 284 slides over the handle 116 and covers the firing bar 282 and a portion of the reciprocating anvil adjusting rod 114 within cavity 118. Preferably, carrier cover 284 forms an opening 298 through which a threaded portion 132 of the handle 116 is received. The opening 298 is preferably U-shaped and formed on an underside 300 of the carrier cover 284, so that when the carrier cover 284 is slid over the handle 116, an abutment portion 302 of the carrier cover 284 is pressed against a portion of the handle 116, indicating that the carrier cover 284 is properly positioned over the firing bar 282 and a portion of the reciprocating anvil adjusting rod 114 within the cavity 118. By allowing for carrier cover 284 to slide over the handle 116, carrier cover 284 protects both the firing bar 282 and the reciprocating anvil adjusting rod 114 within the cavity 118 and allows for them to be easily serviced or replaced.

Shaft assembly 106 is detachably coupled with the handle 116 at a proximal end and detachably coupled with the stapling cartridge assembly 108 (see FIG. 1) at a distal end. As used herein, the term detachable refers to a first component or member which is designed to be unfastened or disconnected without damage to another component or member. Additionally, as used herein, the term detachably coupled or detachably secured refers to coupling or securing a first member to a second member in a manner in which the two members are designed to be unfastened or disconnected from each other without damage to either member. This allows for a user to disconnect or unfasten the two members from each other without damage so that a user may service the two members. Detachable couplings may include a snap-fit coupling, a frictionally engaging coupling which includes members which frictionally engage each other, a threaded coupling, a magnetic coupling, or a mechanical coupling such as a hook and loop type fastener.

Referring to FIG. 3, preferably the shaft assembly 106 has the connecting nut 130 with internal threads 304 which are detachably coupled with the threaded portion 132 on the handle 116. Alternatively, connecting nut 130 may be replaced with any detachable coupling, as described herein. Once detachably coupled with the handle 116, shaft assembly 106 detachably secures the carrier cover 284 to the handle 116 allowing for the circular stapling instrument 100, and its components, such as shaft assembly 106, carrier cover 284, handle 116, firing bar 282, and the reciprocating anvil adjusting rod 114 to be easily disassembled and serviced.

By detachably coupling the shaft assembly 106 with the handle 116, by detachably securing both the firing bar 282 and the reciprocating anvil adjusting rod 114 in the cavity 118, by allowing for carrier cover 284 to slide over the handle 116, by detachably coupling the reciprocating anvil adjusting rod 114 with the anvil control member 120, by detachably coupling the shaft assembly 106 with the handle 116, or by detachably coupling the anvil assembly 112 (see FIG. 1) with the reciprocating anvil adjusting rod 114, assembly and disassembly of the circular stapling instrument 100 is made easier and allows for servicing and maintenance of the various components with the circular stapling instrument 100.

With reference to FIGS. 15A and 15B, in assembling the circular stapling instrument 100, the anvil control member 120 is detachably coupled with the reciprocating anvil adjusting rod 114. Preferably, the anvil control member 120 is detachably coupled with the threaded adjustment member 286 at a proximal end of the reciprocating anvil adjusting rod 114 by turning the anvil control member 120 on the threaded adjustment member 286. Typically, turning the anvil control member counter-clockwise 120 opens the device and turning clockwise closes the device.

Figure 16A:
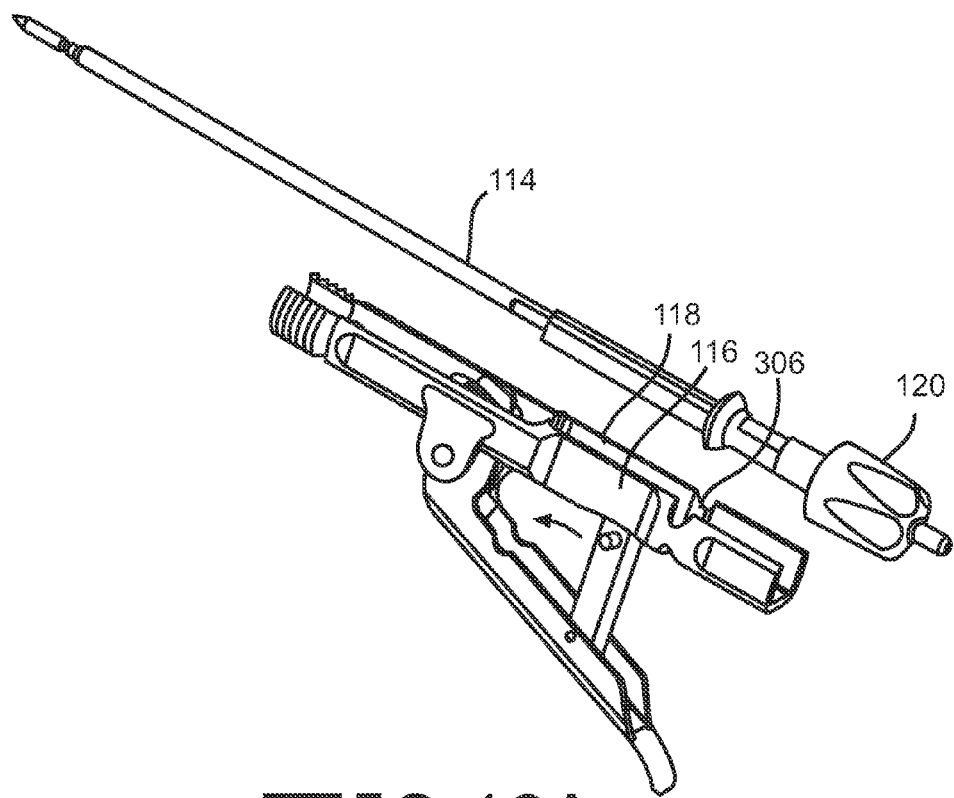
FIGS. 16A and 16B illustrate perspective assembly views, during different stages of assembly, of the anvil closure knob connected with the reciprocating anvil adjusting rod of FIGS. 15A and 15B along with a handle of the reusable circular stapling instrument of FIG. 1.
Figure 16B:
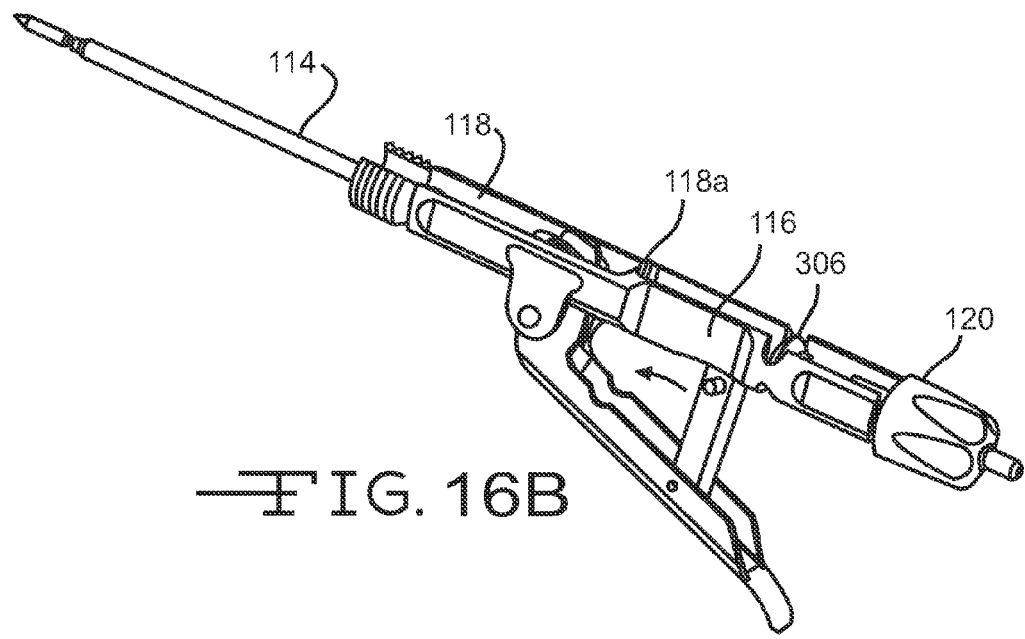

Then, with reference to FIGS. 16A and 16B, a portion of the anvil control member 120 and a portion of the reciprocating anvil adjusting rod 114 are detachably secured within the cavity 118 of the handle 116. Preferably, the cavity 118 forms an indentation 306 which mates with a portion of the anvil control member 120, in order to detachably secure the anvil control member 120 and the reciprocating anvil adjusting rod 114 within the cavity 118. Alternately, the indentation and protrusion relationship can be reversed. Once the reciprocating anvil adjusting rod 114 is placed in the cavity 118 at location 118A, the parallel and planar walls 114B and 114C (see FIG. 15B) adjoining the cavity 118 are connected in a fashion that prevents rotational movement of the reciprocating anvil adjusting rod 114 relative to the handle while allowing longitudinal movement.

Figure 17A:
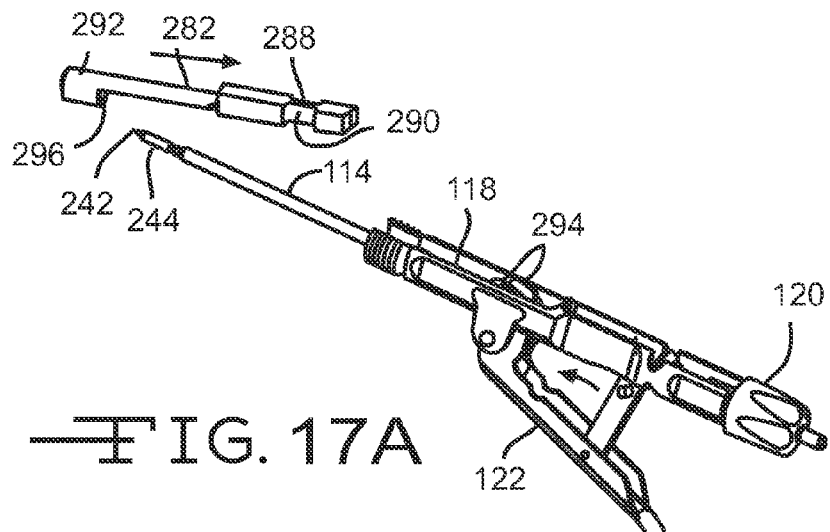
FIGS. 17A, 17B and 17C illustrate perspective assembly views, during different stages of assembly, of the anvil closure knob connected with the reciprocating anvil adjusting rod and the handle of FIGS. 16A and 16B along with a firing bar of the reusable circular stapling instrument of FIG. 1.
Figure 17B:
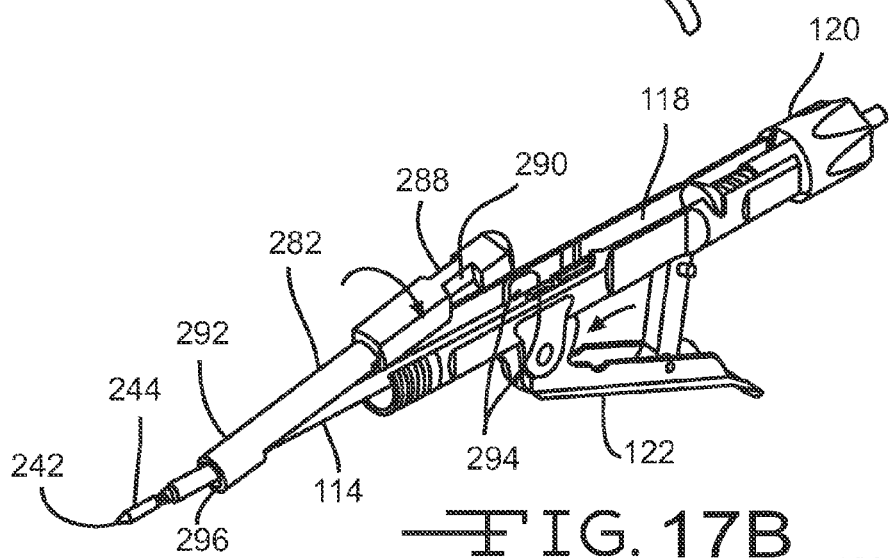
Figure 17C:
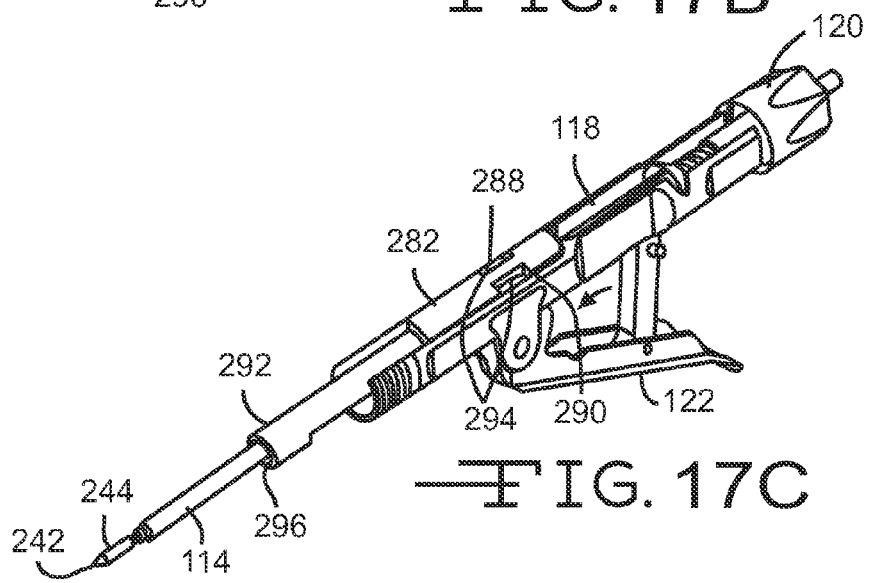

With reference to FIGS. 17A, 17B, and 17C, the tip 242 and the engagement member 244 of the reciprocating anvil adjusting rod 114 are received through the opening 296 of the engagement shaft 292 of the firing bar 282 and then the engagement grooves 288, 290 of the firing bar 282 are placed over and then around the upper end 294 of the firing trigger 122, detachably securing the firing bar 282, the reciprocating anvil adjusting rod 114, and the anvil control member 120 within the cavity 118.

Figure 18A:
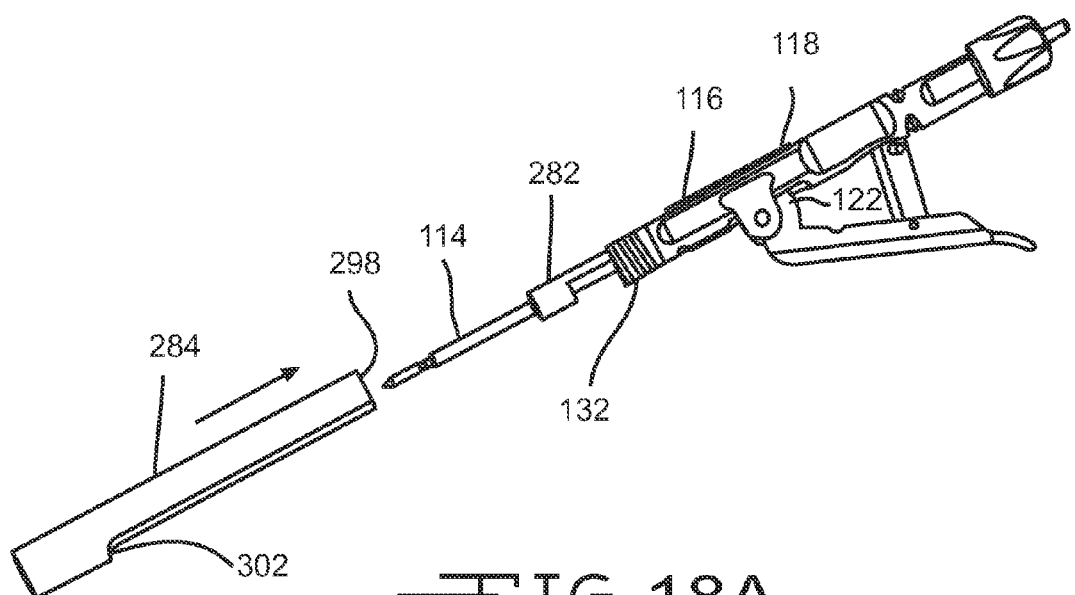
FIGS. 18A and 18B illustrate perspective assembly views, during different stages of assembly, of the anvil closure knob connected with the reciprocating anvil adjusting rod, the handle, and the firing bar of FIGS. 17A, 17B, and 17C along with a carrier cover of the reusable circular stapling instrument of FIG. 1.
Figure 18B:
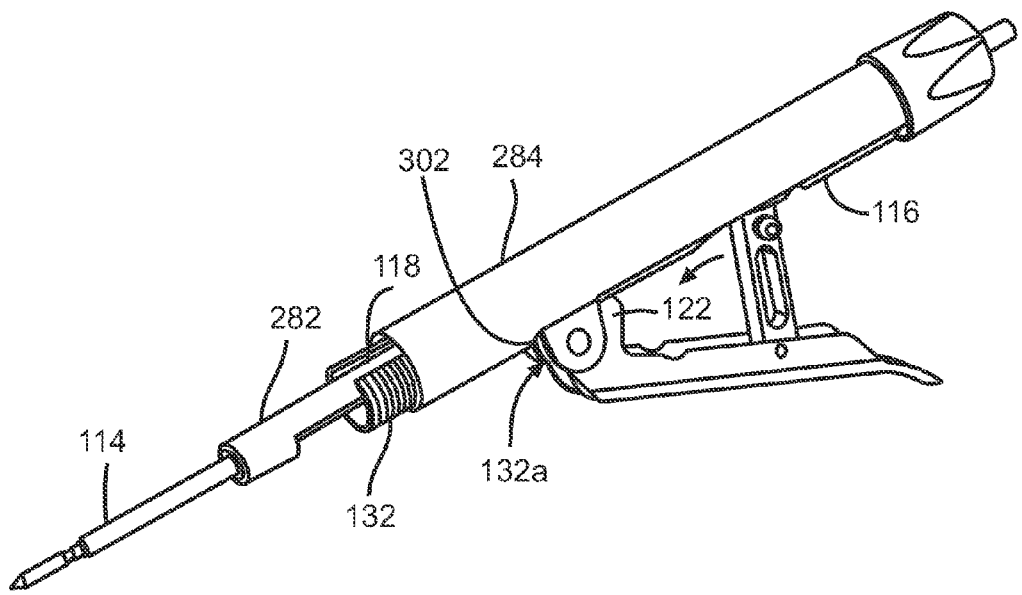

With reference to FIGS. 18A and 18B, the carrier cover 284 is then slid over the handle 116 and covers the firing bar 282 and a portion of the reciprocating anvil adjusting rod 114 within cavity 118. Preferably, the threaded portion 132 of the handle 116 is received through the opening 298 in the carrier cover 284, and the carrier cover 284 is slid until abutment portion 302 of the carrier cover 284 is pressed against a portion 132a of the handle 116, indicating that the carrier cover 284 is properly positioned.

Figure 19A:
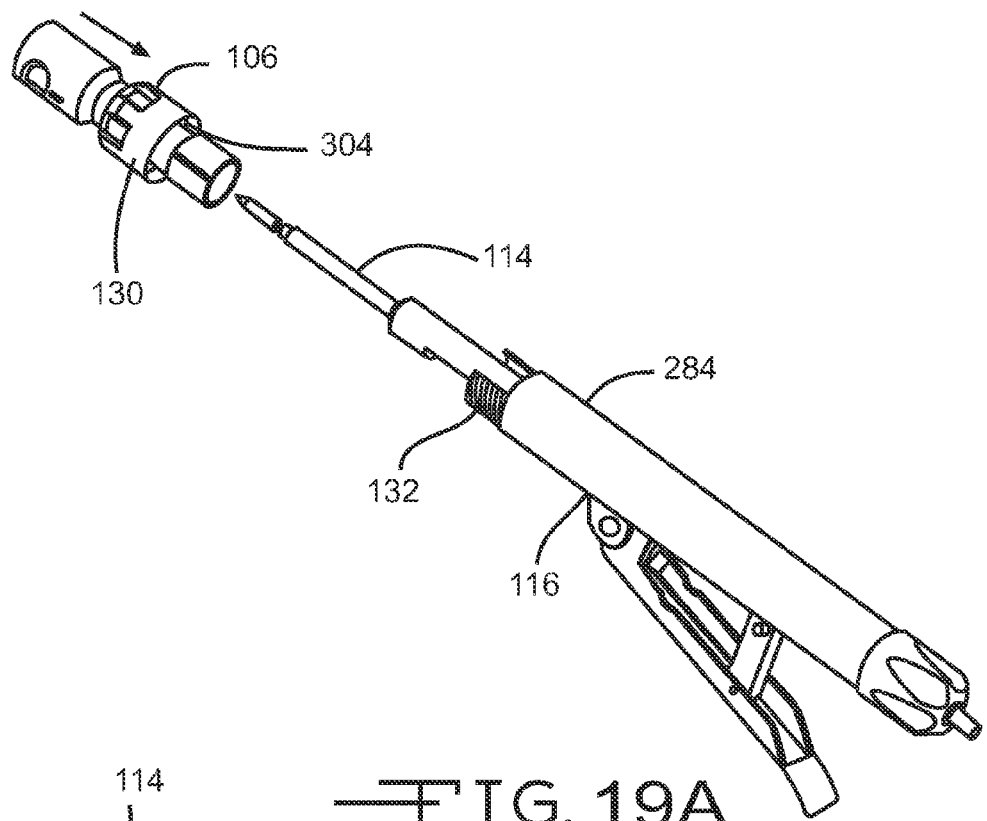
FIGS. 19A, 19B and 19C illustrate perspective assembly views, during different stages of assembly, of the anvil closure knob connected with the reciprocating anvil adjusting rod, the handle, the firing bar, and the carrier cover of FIGS. 18A, and 18B along with a shaft assembly of the reusable circular stapling instrument of FIG. 1.
Figure 19B:
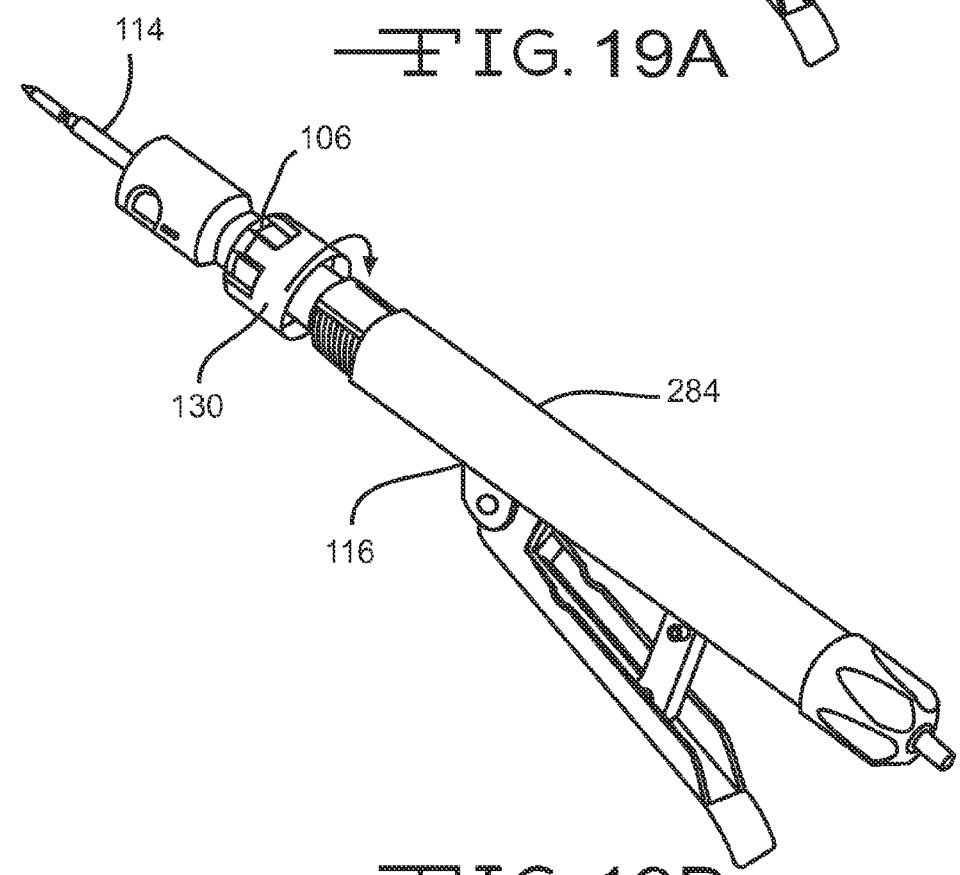
Figure 19C:
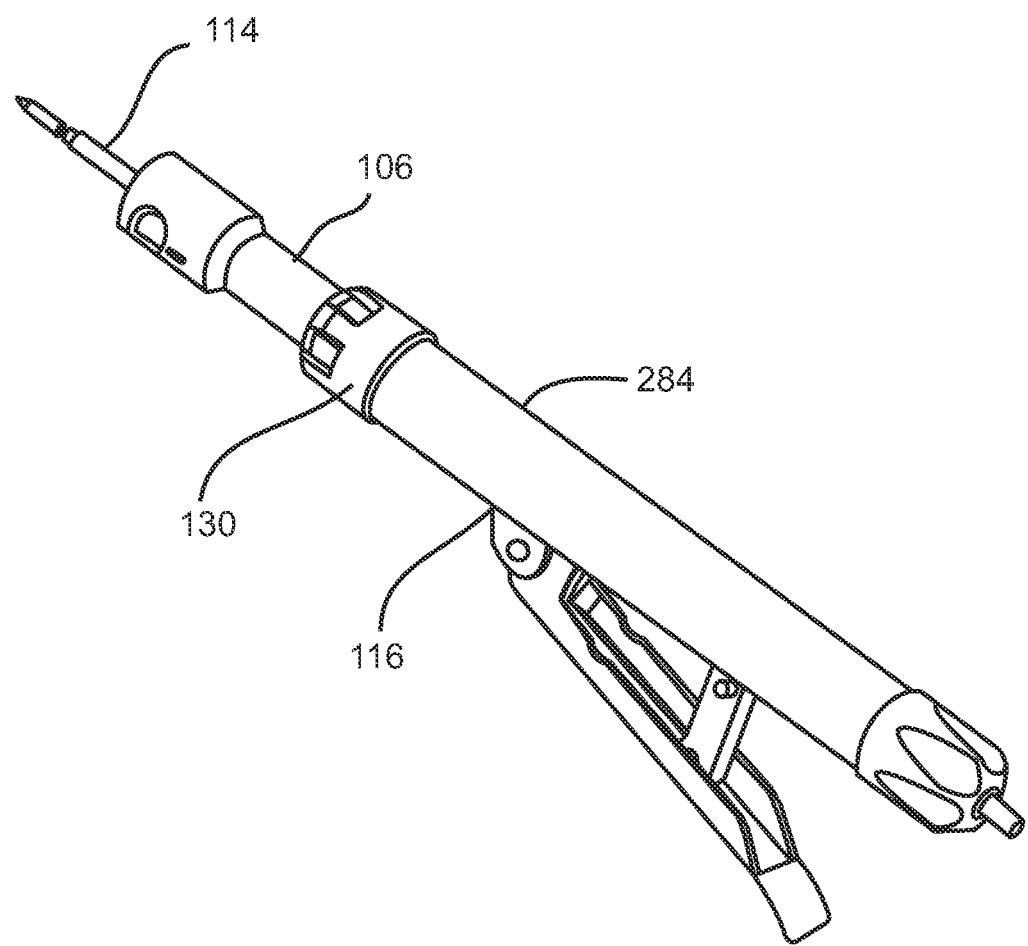

With reference to FIGS. 19A, 19B, and 19C, the reciprocating anvil adjusting rod 114 is placed through and within the shaft assembly 106 and the shaft assembly 106 is detachably coupled with the handle 116. Preferably, shaft assembly 106 has the connecting nut 130 with the internal threads 304 which are detachably coupled with the threaded portion 132 on the handle 116. The shaft assembly 106 detachably secures the carrier cover 284 to the handle 116.

Then, with reference to FIG. 2, stapling cartridge assembly 108 is detachably coupled to the shaft assembly 106, and the tip 242 of the reciprocating anvil adjusting rod 114 extends through a central shaft formed in the stapling cartridge assembly 108. Finally, anvil assembly 112 is detachably coupled with the reciprocating anvil adjusting rod 114 via the engagement member 244 of the reciprocating anvil adjusting rod 114 and the proximal end channel 236 of the metal shaft 216 of the anvil assembly 112.

Figure 20:
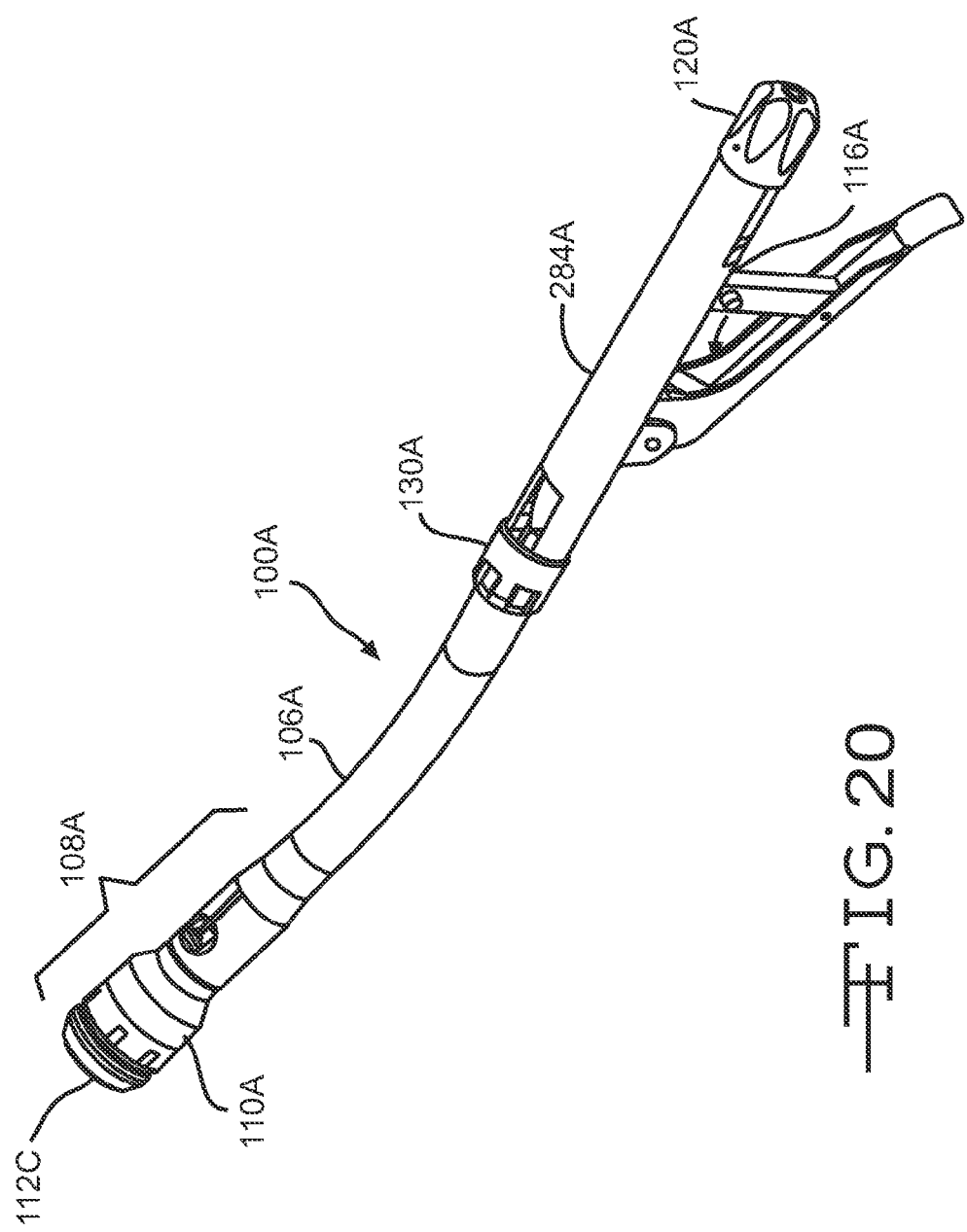
FIG. 20 illustrates a perspective view of a curved reusable circular stapling instrument having an open assembly architecture, in accordance with another preferred embodiment.
Figure 21:
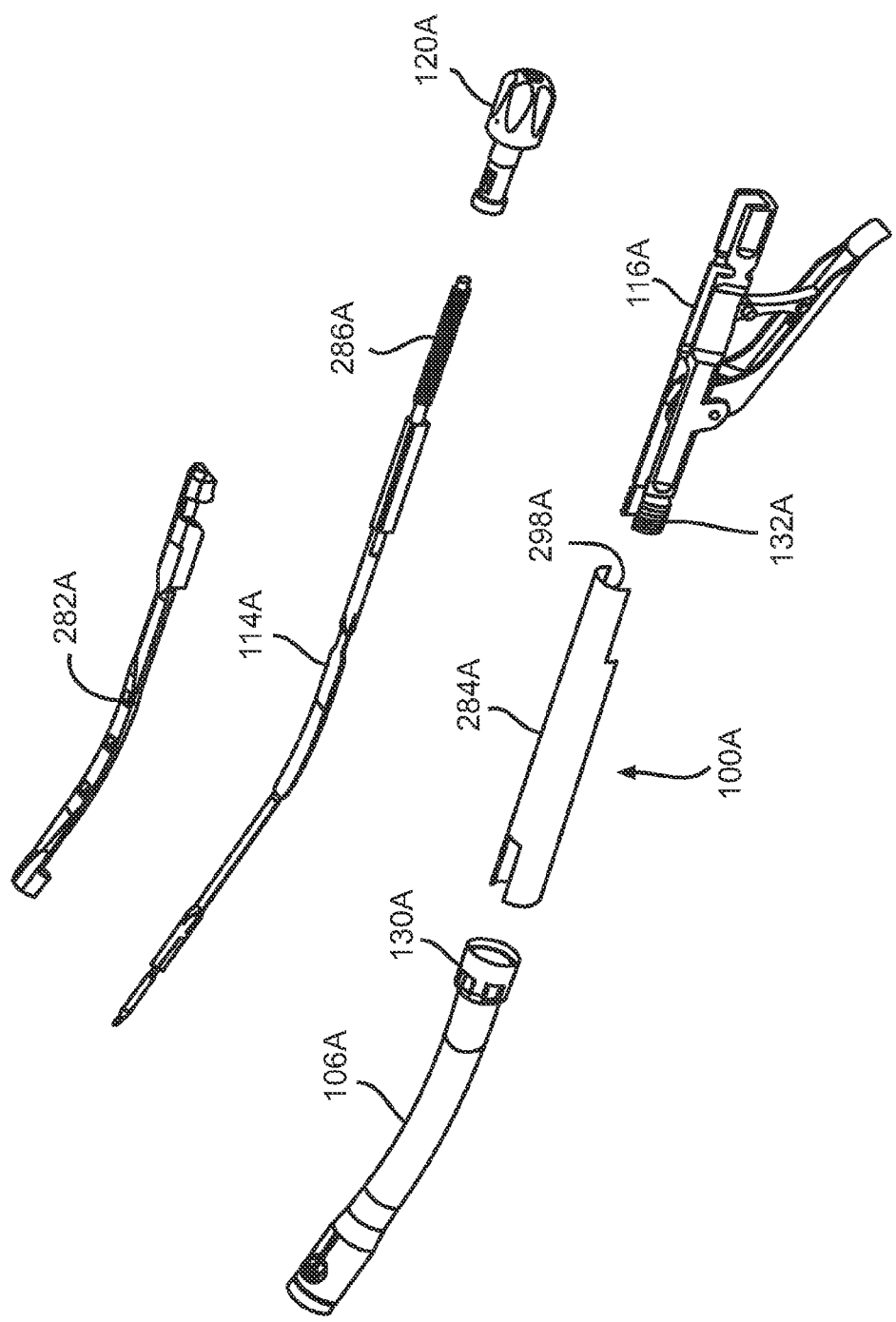
FIG. 21 illustrates an exploded perspective view of the curved reusable circular stapling instrument of FIG. 20.

With reference to FIGS. 20 and 21, in one embodiment, a curved circular stapling instrument 100A is provided which includes a stapling cartridge assembly 108A having a casing 110A, an anvil assembly 112C attached to a curved reciprocating anvil adjusting rod 114A of an anvil opening mechanism, as discussed above, to prevent accidental removal of the anvil assembly 112C, a curved firing bar 282A which is detachably coupled with the flexible reciprocating anvil adjusting rod 114A, a carrier cover 284A detachably coupled with a handle 116A, a control member 120A detachably coupled with the curved reciprocating anvil adjusting rod 114A via a threaded adjustment member 286A, and an ergonomic curved shaft assembly 106A having a connecting nut 130A detachably coupled with the handle 116A via threaded portion 132A. Curved circular stapling instrument 100A includes curved components, such as the flexible reciprocating anvil adjusting rod 114A, the curved firing bar 282A, and the curved shaft assembly 106A, to aid in insertion into a body cavity of a mammal.

By having components which are detachably coupled with each other circular stapling instrument 100 or curved circular stapling instrument 100A provide a reusable stapling instrument having an open architecture which uses a carrier cover 284, 284A having a u-shaped opening 298, 298A that allows for additional components, such as reciprocating anvil adjusting rod 114, 114A and shaft assembly 106, 106A, to be assembled in a primarily transverse direction. A transverse assembly allows for easy visualization for assembly and decreases assembly time, improves ease of assembly, and disassembly. As a result, the amount of time required to assemble the circular stapling instrument 100 or the curved circular stapling instrument 100A having the open assembly architecture is often less than one minute. Additionally, the open architecture allows for presence of features that communicate where the components need to be placed. Further, by providing components which are detachably coupled with each other, the circular stapling instrument 100 or 100A is easily assembled or disassembled, allowing for cleaning and sterilization of the circular stapling instrument 100 or 100A after use.

With reference to FIGS. 22-28, in one embodiment, a circular stapling instrument 100D is provided which includes a stapling cartridge assembly 108D having a casing 110D, an anvil assembly 112D attached to a reciprocating anvil adjusting rod 114D of an anvil opening mechanism, as discussed above, to prevent accidental removal of the anvil assembly 112D, a firing bar 282D which is detachably coupled with the reciprocating anvil adjusting rod 114D, a carrier cover 284D coupled with a handle 116D, a control member 120D coupled with the reciprocating anvil adjusting rod 114D, and a shaft assembly 106D having a connecting nut 130D coupled with the handle 116D via a threaded portion 132D. Preferably, the circular stapling instrument 100D is a curved circular stapling instrument, as seen with instrument 100D, and includes curved components, such as a curved reciprocating anvil adjusting rod 114D, a curved firing bar 282D, and an ergonomic curved shaft assembly 106D, to aid in insertion into a body cavity of a mammal. However, circular stapling instrument 100D need not be a curved circular stapling instrument, as seen with circular stapling instrument 100D, and may be any type of circular stapling instrument, such as a relatively straight circular stapling instrument, as seen with circular stapling instrument 100, and have relatively straight components, such as a relatively straight reciprocating anvil adjusting rod 114D, a relatively straight firing bar 282D, and a relatively straight shaft assembly 106D.

Figure 22:
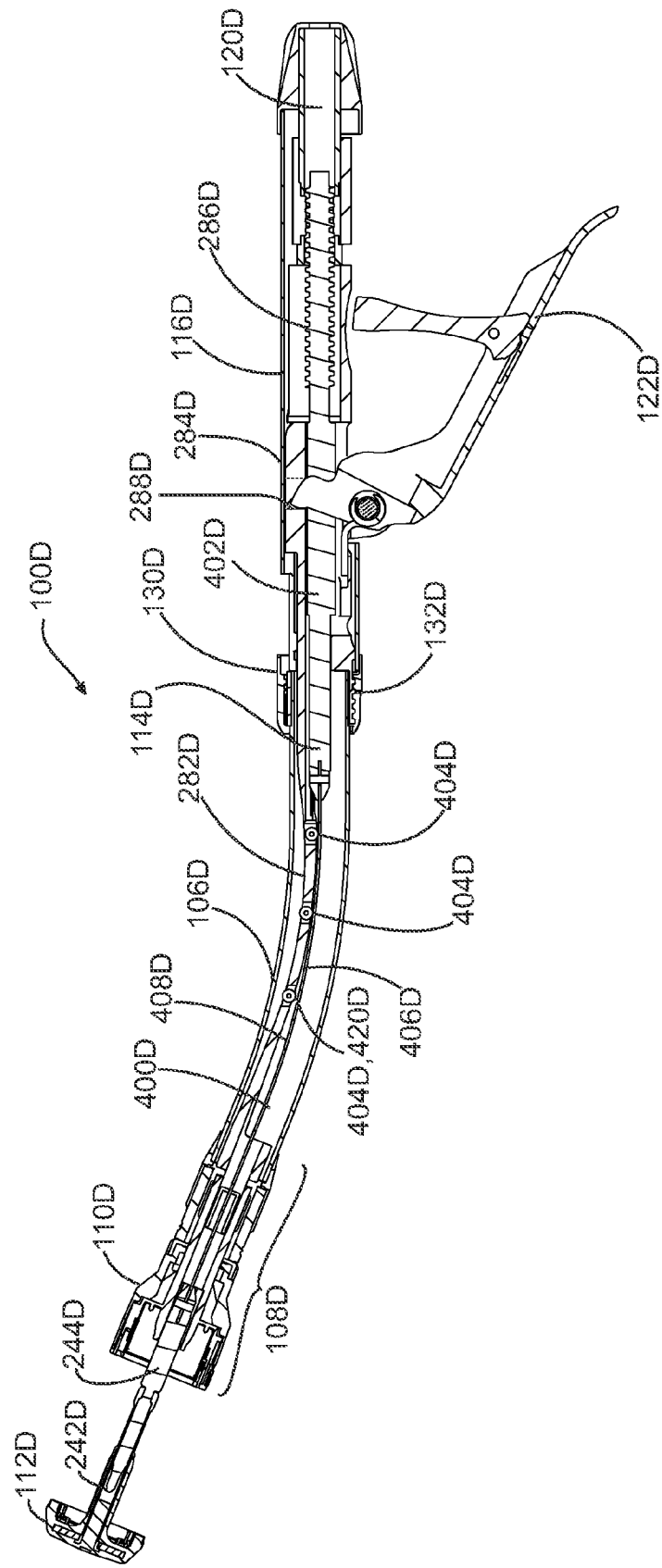
FIG. 22 illustrates a cross-section view of a curved circular stapling instrument having a frictional reducing member, with the instrument in an open condition.
Figure 23:
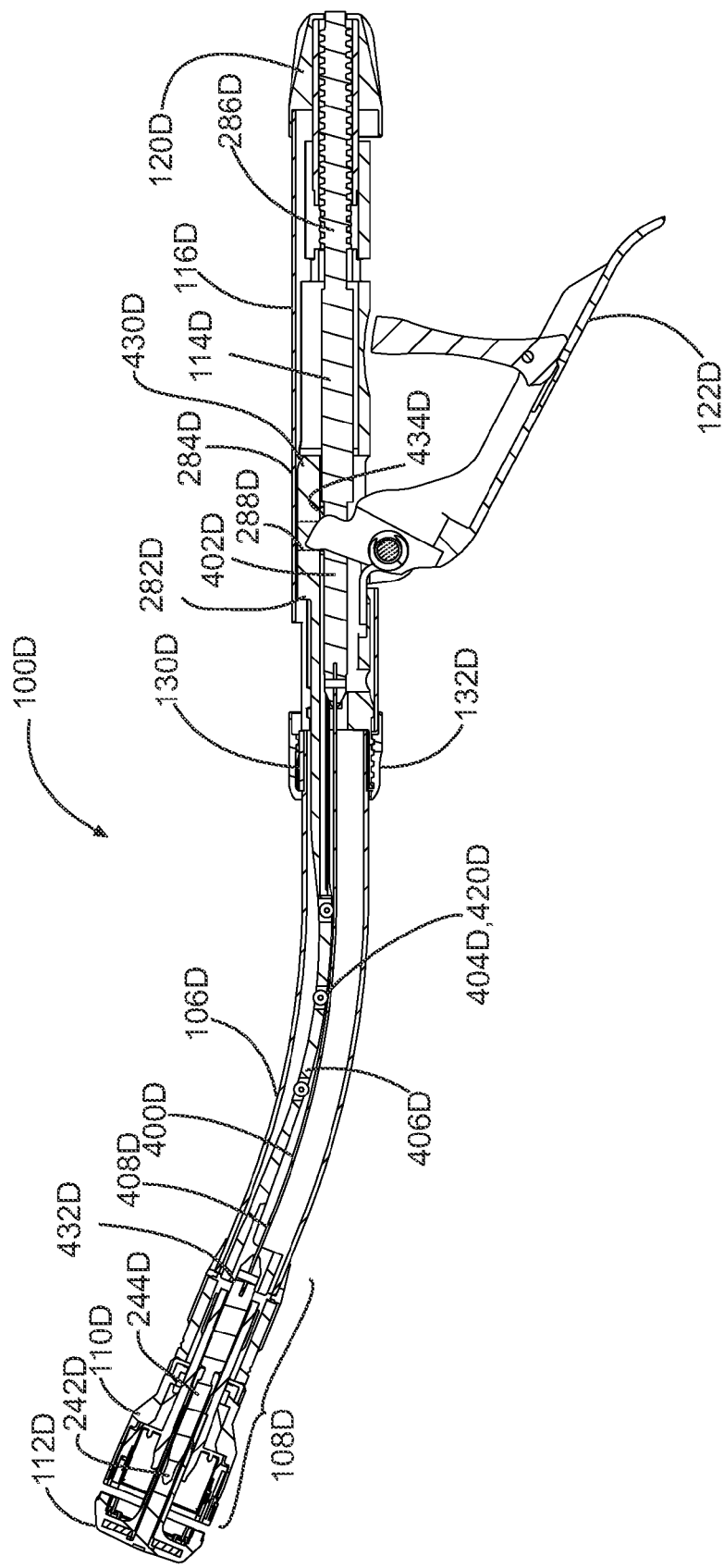
FIG. 23 illustrates a curved cross-section view of a circular stapling instrument having a frictional reducing member, with the instrument in a closed position before firing staples.
Figure 24:
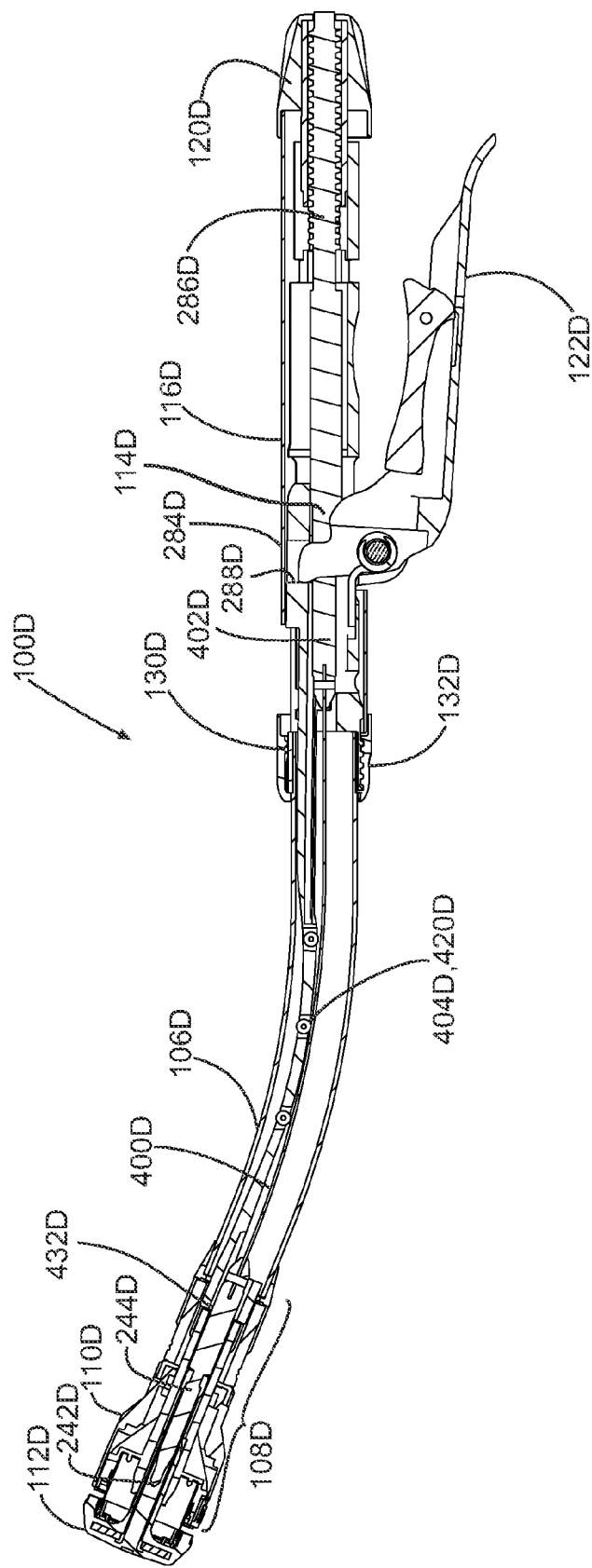
FIG. 24 illustrates a cross-section view of a curved circular stapling instrument having a frictional reducing member, with the instrument in a fully fired condition upon firing staples.
Figure 28:
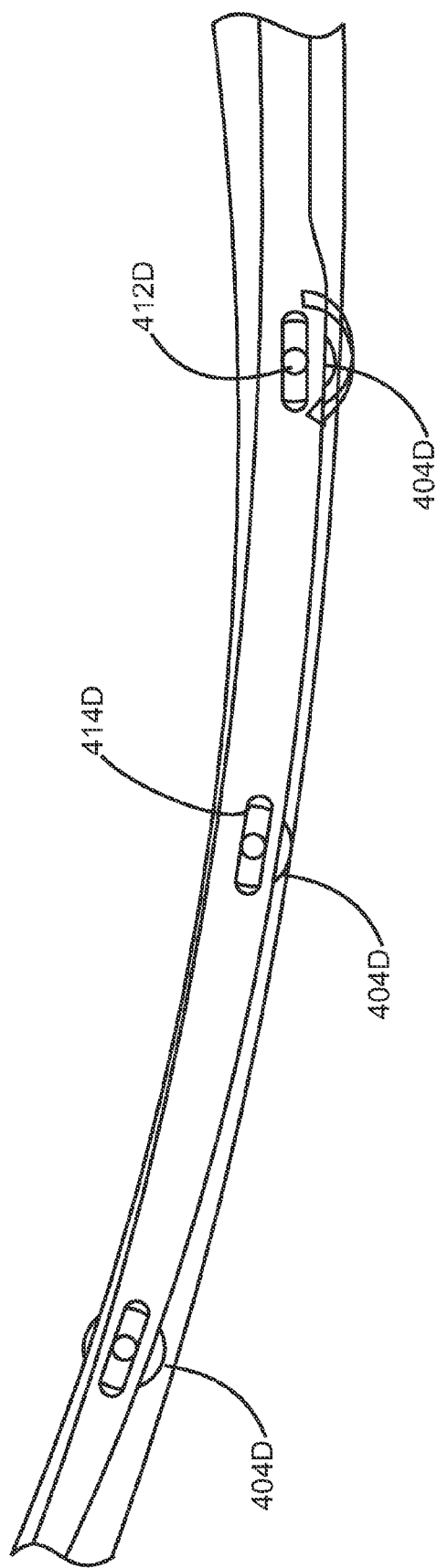
FIG. 28 illustrates an enlarged side view of a firing bar of a circular stapling instrument having an alternate embodiment of a frictional reducing member adjacent a reciprocating anvil adjusting rod.

The reciprocating anvil adjusting rod 114D includes a first engagement member 244D at a tip 242D of the reciprocating anvil adjusting rod 114D and a threaded adjustment member 286D at a base 402D of the reciprocating anvil adjusting rod 114D. Preferably, the reciprocating anvil adjusting rod 114D includes a base 402D at one end, an engagement member 244D at an opposing end, and a flexible tension band 400D, which may be flexible and curved, connecting the base 402D with the engagement member 244D. With reference to FIGS. 22 and 23, the firing bar 282D is movably connected at a first end 430D with a firing trigger 122D and movably connected at a second end 432D with a stapling cartridge assembly 108D through a second engagement member 416D. With reference to FIG. 28, the firing bar 282D forms a first engagement surface 406D which faces a respective second engagement surface 408D formed on the reciprocating anvil adjusting rod 114D. Preferably, the tension band 400D forms the second engagement surface 408D which faces the first engagement surface 406D on the firing bar 282D.

Circular stapling instrument 100D further includes a frictional reducing member 420D located in between the first and second engagement surfaces 406D, 408D in order to reduce friction between the reciprocating anvil adjusting rod 114D and the firing bar 282D. Movement between the reciprocating anvil adjusting rod 114D and the firing bar 282D occurs when the firing trigger 122D is engaged by the handle 116D and fired, causing the firing bar 282D to move towards and engage the stapling cartridge assembly 108D and fire staples from the stapling cartridge assembly 108D. Movement between the reciprocating anvil adjusting rod 114D and the firing bar 282D also occurs when the control member 120D is activated causing the reciprocating anvil adjusting rod 114D, and the anvil assembly 112D connected to the tip 242D of the reciprocating anvil adjusting rod 114D, to move towards or away from the stapling cartridge assembly 108D in order to adjust a distance between the stapling cartridge assembly 108D and the anvil assembly 112D. Either movement between the reciprocating anvil adjusting rod 114D and the firing bar 282D causes the reciprocating anvil adjusting rod 114D to slidably engage the firing bar 282D, and results in friction between the reciprocating anvil adjusting rod 114D and the firing bar 282D. The term slidably engage as used herein refers to movement of one surface over a second surface while maintaining smooth continuous contact between the two surfaces. Friction between the reciprocating anvil adjusting rod 114D and the firing bar 282D in curved circular stapling instrument 100D typically could be 20-40% higher over a relatively straight circular stapling instrument 100. In one embodiment, the configuration of the circular stapling instrument 100D, causes the tension band 400D to exert a contact force on the firing bar 282D, increasing friction between the firing bar 282D and the reciprocating anvil adjusting rod 114D. By placing frictional reducing member 420D in between the first and second engagement surfaces 406D, 408D, friction between the reciprocating anvil adjusting rod 114D and the firing bar 282D may be reduced. There also exist other areas where frictional forces between the firing bar 282D and other portions of the handle 116D occur during firing the instrument. These frictional forces are reduced by providing a predetermined angle on the surfaces in grooves 288D and 290D of the firing bar 282D. As shown in FIG. 38B, the angled surface 288F can be oriented from 5 degrees to 15 degrees from vertical. This results in a 10-20% reduction in force to push the firing bar 282D.

Frictional reducing member 420D may be any mechanical device or chemical compound which may be used to reduce friction between two members, such as between the reciprocating anvil adjusting rod 114D and the firing bar 282D. In particular, the frictional reducing member 420D provides a reduced coefficient of friction $\mu_{reduced}$ between two members which is less than a normal coefficient of friction $\mu_{normal}$ present between the two members, when the two members are without the frictional reducing member. Preferably, the frictional reducing member 420D provides for a reduced coefficient of friction $\mu_{reduced}$ which is at least 20% less than, and more preferably, at least 40% less than the normal coefficient of friction $\mu_{normal}$ present between the two members.

Chemical compounds for frictional reducing member 420D may include: solid coatings including graphite or polymer coatings such as Teflon. Chemical compounds for frictional reducing member 420D may be applied as coatings which bond to either or both the first and second engagement surfaces 406D, 408D. Chemical compounds for frictional reducing member 420D may be also be applied as coatings to free moving intermediate components captured between the two engagement surfaces 406D, 408D. Mechanical devices used for frictional reducing member 420D include any mechanical device which can reduce friction between a pair of surfaces, such as a ball bearing or a roller bearing. Frictional reducing member 420D may be connected with either or both the reciprocating anvil adjusting rod 114D and the firing bar 282D. The frictional reducing member 402D is designed so that it does not wipe-out or degrade during cleaning and servicing the handle for reuse.

Figure 25:
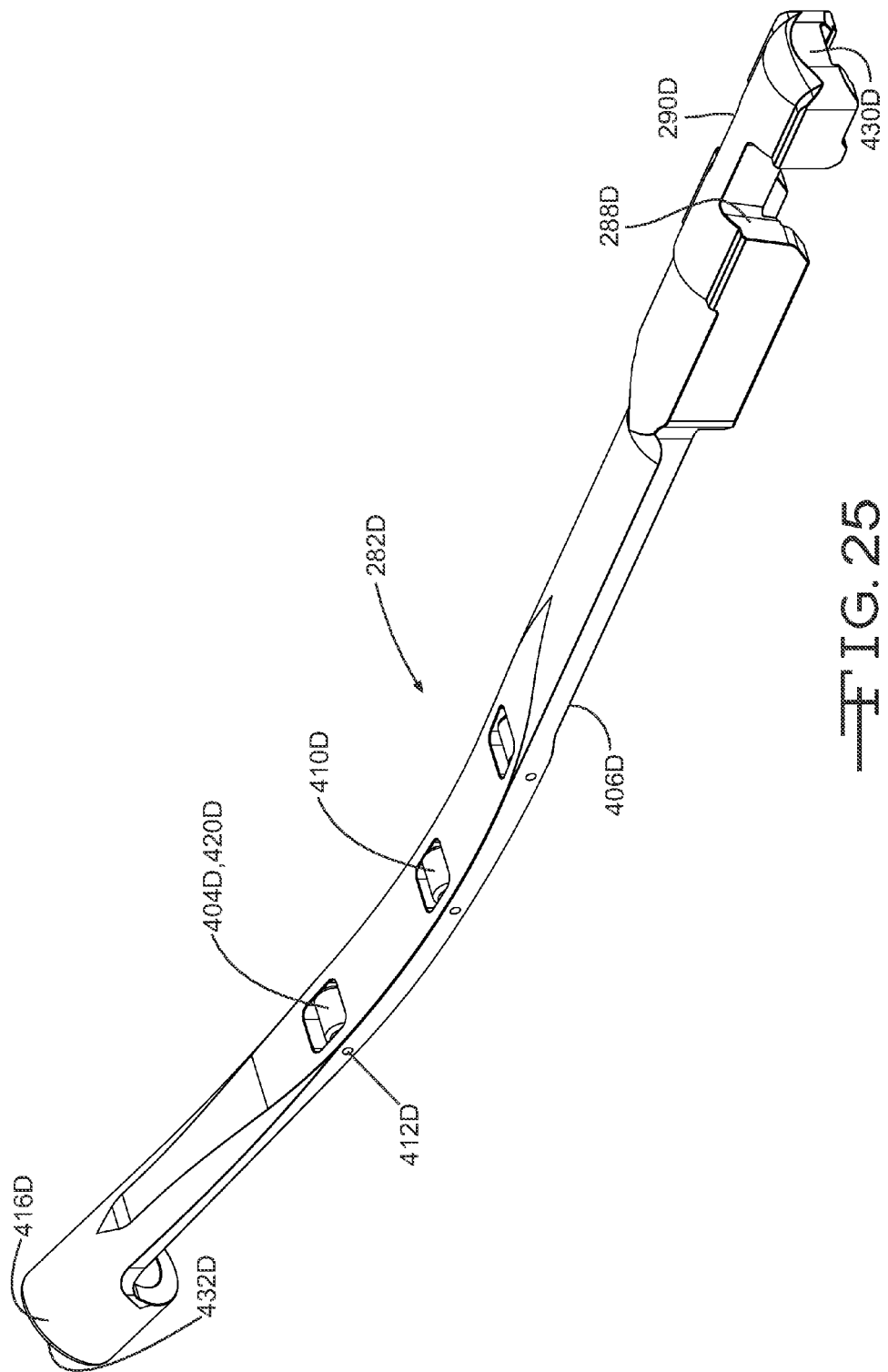
FIG. 25 illustrates a perspective view of a firing bar of a curved circular stapling instrument having a frictional reducing member.
Figure 26:
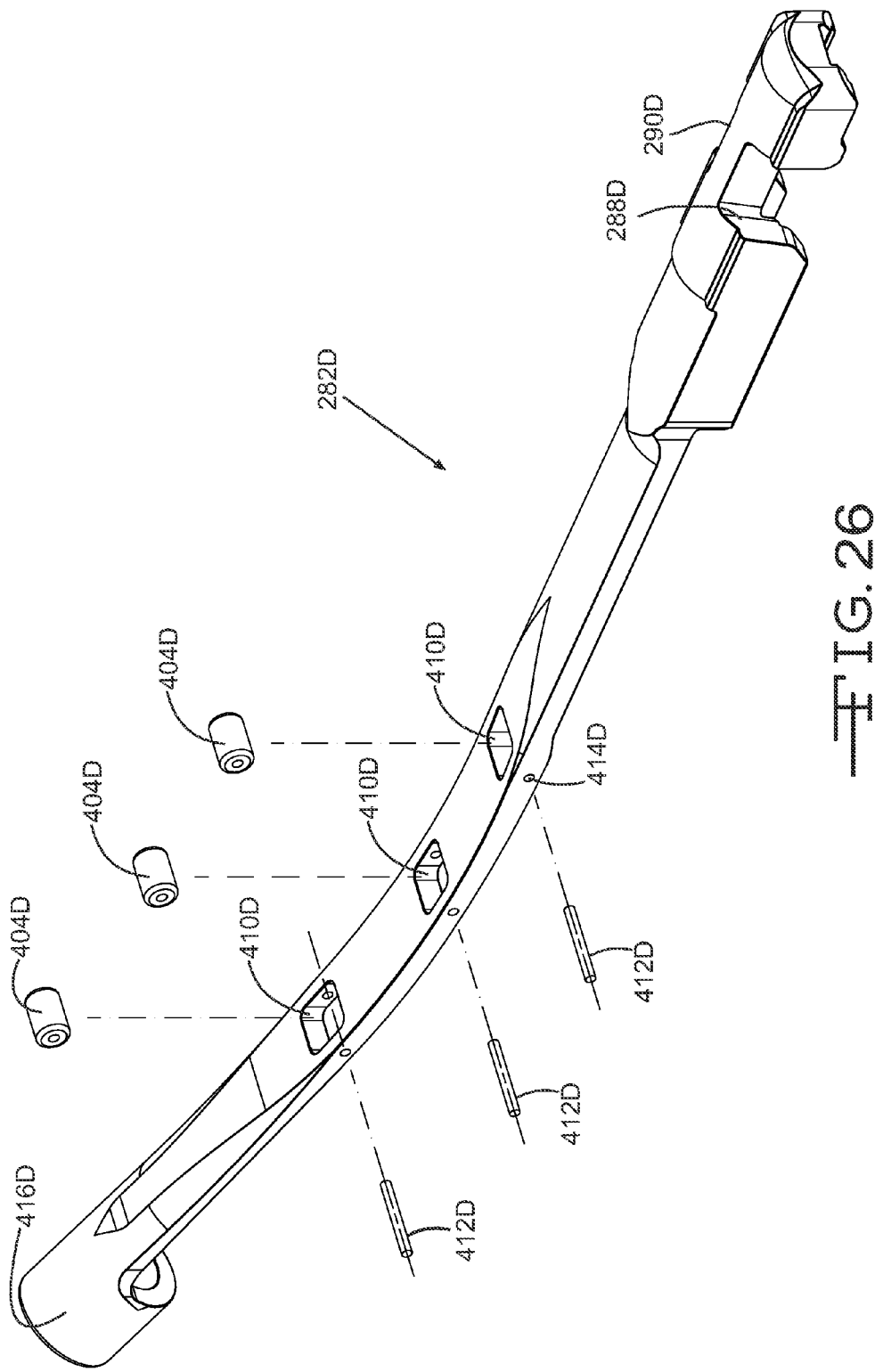
FIG. 26 illustrates an exploded perspective view of a firing bar of a circular stapling instrument having a frictional reducing member.
Figure 27:
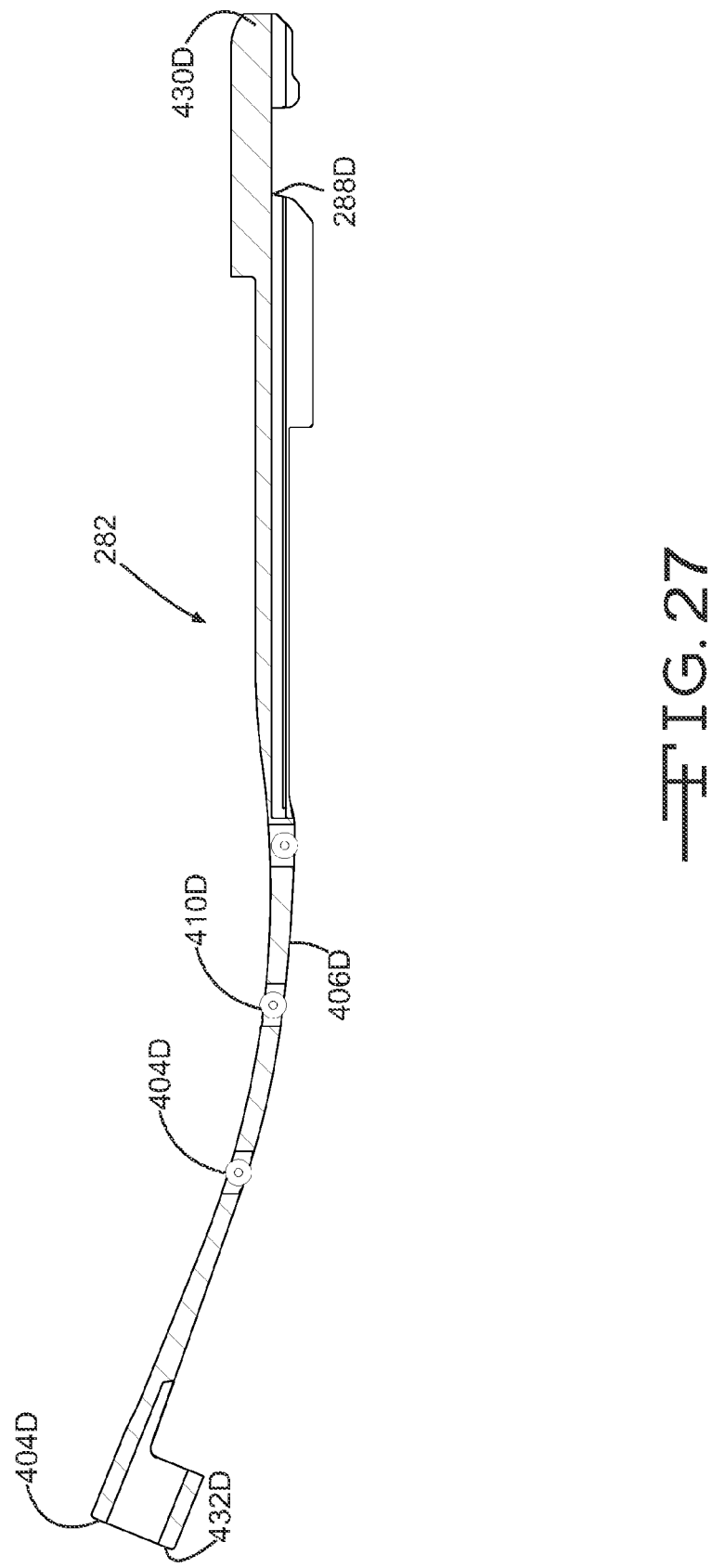
FIG. 27 illustrates a cross-section view of a firing bar of a circular stapling instrument having a frictional reducing member.

With reference to FIGS. 25-27, in one embodiment, the frictional reducing member 420D includes a roller 404D which is connected with the firing bar 282D using a pin 412D and which is disposed within a cavity 410D formed in the firing bar 282D. Preferably, the pin 412D is disposed within a hole 414D formed through the firing bar 282D. Preferably, more than one roller 404D is connected with the firing bar 282D, such as three rollers 404D. In one embodiment, hole 414D forms a circular opening through which the pin 412D is disposed, as shown in FIG. 26, allowing for little movement of the pin 412D. In one embodiment, the hole 414D forms a generally oval shaped opening through which the pin 412D is disposed and may move laterally within, as shown in FIG. 28, allowing for more lateral movement of the pin 412D either towards or away from either end 430D, 432D of firing bar 282D than top/bottom movement of pin 412D which is not towards or away from either end 430D, 432D of firing bar 282D, allowing an additional degree of freedom compared to the previous embodiment.

Figure 29:
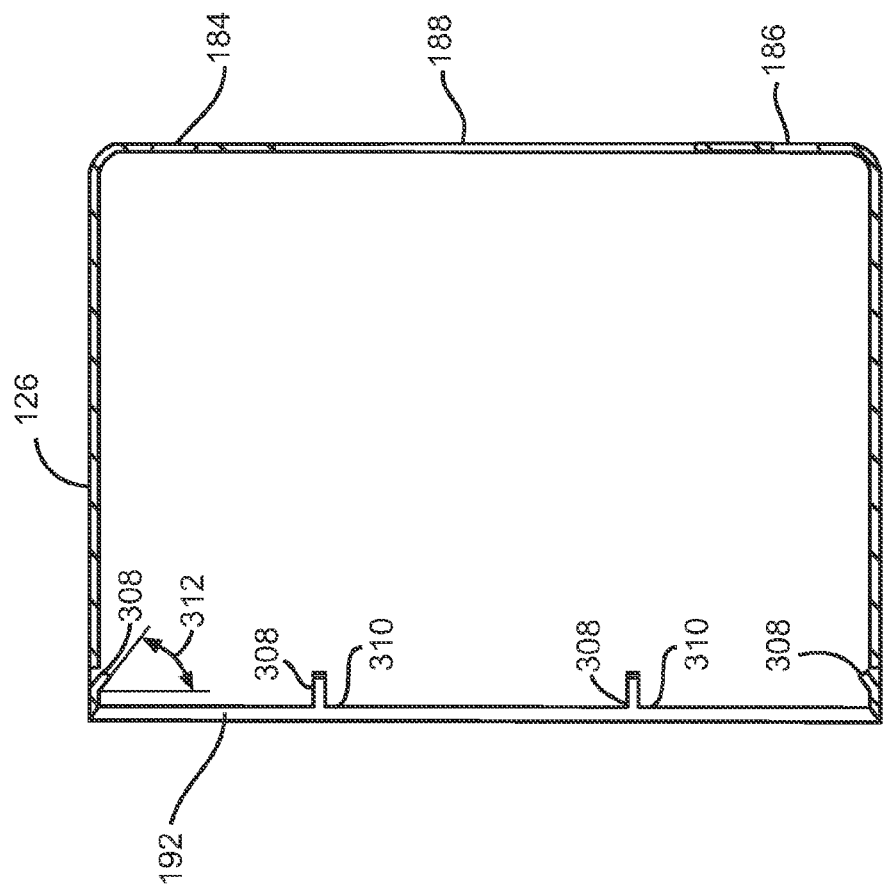
FIG. 29 illustrates a cross-section view of an annular blade of the stapling reload assembly of the circular stapling instrument of FIG. 4.

FIG. 29 illustrates a perspective view of the annular blade 126 of the stapling cartridge assembly 108 of the circular stapling instrument 100 of FIG. 4. As shown in FIG. 29, the annular blade 126 comprises an annular cutting edge 192 and a breakaway washer attachment member 308. The annular blade 126, including the annular cutting edge 192 and the breakaway washer attachment member 308, is made of a metal such as stainless steel. In other embodiments, the annular blade 126 may be made of any material hard enough to cut. The breakaway washer attachment member 308 comprises a plurality of spaced-apart breakaway washer retention barbs extending from locations 310 of the annular blade 126 which are adjacent to the cutting edge 192. The breakaway washer attachment member 308 extends inwardly at a non-parallel angle 312 relative to the cutting edge 192. The non-parallel angle 312 may be in a range of 56 to 60 degrees. In other embodiments, the non-parallel angle 312 may be in a range of 30 to 60 degrees. In still other embodiments, the breakaway washer attachment member 308 may vary in material, quantity, shape, size, location, direction, or configuration relative to the annular blade 126. For instance, in other embodiments the breakaway washer attachment member 308 may comprise a snap, an impression, or other type of attachment member.

FIG. 6 illustrates the anvil base surface 220 of the anvil assembly 112 of the stapling reload assembly 102 of the circular stapling instrument 100 being in an open position relative to and apart from the casing 110, and the staple driver 156 and the attached annular blade 126 being in a pre-fired position retracted within the casing 110. The annular breakaway washer 214 is press-fit within the cavity 222 of the anvil base surface 220 of the anvil 210. A protective member 314 is attached, using a hook 316, to a top portion 318 of the annular breakaway washer 214 disposed within the cavity 222 of the anvil base surface 220.

Figure 30:
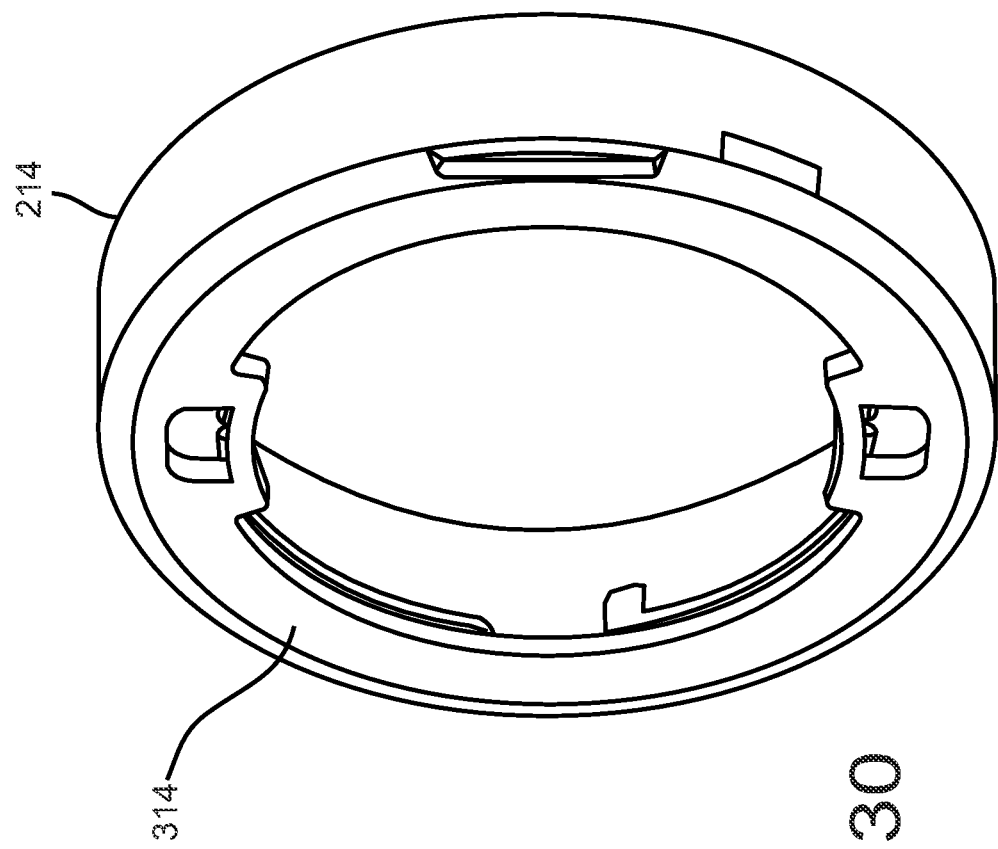
FIG. 30 illustrates a perspective view of an annular breakaway washer attached to a protective member.

FIG. 30 shows a close-up view of the annular breakaway washer 214 attached to the protective member 314. The protective member 314 comprises an annular protective cap made of a red colored polycarbonate. In other embodiments, the protective member 314 may vary in material, shape, size, location, color, or configuration, and may be attached to the annular breakaway washer 214 using varying attachment mechanisms. In still other embodiments, the protective member 314 may not be used and the annular breakaway washer 214 may be press-fit within the cavity 222 of the anvil base surface 220 without the protective member 314.

FIG. 7 shows the anvil base surface 220 of the anvil assembly 112 having been moved to a closed position relative to and adjacent to the casing 110 with the staple driver 156 and the attached annular blade 126 still being in the pre-fired position retracted within the casing 110 spaced apart from the annular breakaway washer 214. In this pre-fired position the flexible detent members 178 of the staple driver 156 are detachably connected to the detent bumps 180 of the casing 110 with the connection preventing the staple driver 156 from moving until a pre-determined amount of force is applied. In other embodiments, the flexible detent members 178 and the detent bumps 180 may comprise varying types of mating members.

FIG. 31 illustrates the staple driver 156 and the attached annular blade 126 having been fired moving the staple driver 156 relative to the casing 110 from the pre-fired position to the fired position in which the cutting edge 192 of the annular blade 126 moves into and cuts the annular breakaway washer 214 while the anvil base surface 220 of the anvil assembly 112 is in the closed position. During the firing, the flexible detent members 178 of the staple driver 156 are released from the detent bumps 180 of the casing 110 allowing the staple driver 156 to move past the certain point 320 relative to the casing 110.

FIG. 32 illustrates a close-up view of the cutting edge 192 of the annular blade 126 of FIG. 31 cutting the annular breakaway washer 214. The cutting edge 192 cuts a web 320, disposed between spaced-apart walls 322 and 324, of the annular breakaway washer 214. As this occurs, the breakaway washer attachment member 308 fixedly attaches to one of the spaced-apart walls 322 of the annular breakaway washer 214 locking the annular blade 126 to the annular breakaway washer 214 with the protective member 314 (see FIG. 31) still attached to the top portion 318 (see FIG. 31) of the annular breakaway washer 214 disposed within the cavity 222 of the anvil base surface 220.

FIG. 33 illustrates the anvil base surface 220 of the anvil assembly 112 having been moved back into the open position away from the casing 110 after the staple driver 156 and the attached annular blade 126 were fired cutting the annular breakaway washer 214. The annular breakaway washer 214 remains locked in place over the annular blade 126, due to the annular breakaway washer attachment member 308, with the protective member 314 still attached to the top portion 318 of the annular breakaway washer 214 acting as a protective barrier over the cutting edge 192 of the annular blade 126. The protective member 314 prevents the cutting edge 192 of the annular blade 126 from making an unintended cut after the annular blade 126 has been fired. At least one of the annular breakaway washer 214 or the protective member 314 comprises a visual indicator 326 indicating, as a precautionary measure, that the staple driver 156 and the attached annular blade 126 have been fired. The visual indicator 326 comprises a first color which is different than a second color of the casing 110 of the circular stapling apparatus 100. In other embodiments, the visual indicator 326 may comprise any type of visual indicator visually indicating when the staple driver 156 and the attached annular blade 126 have been fired. In another embodiment, only the inner portion of the cut annular breakaway washer 214 and the visual indicator 326 remain attached to the annular blade 126. The outer portion of the cut annular breakaway washer 214 remains attached to the anvil base surface 220 after opening the instrument.

FIG. 34 shows the anvil 210 of the anvil assembly 112 of FIG. 33 having been removed from the circular stapling instrument 100, after the staple driver 156 and the attached annular blade 126 were fired cutting the annular breakaway washer 214, with the annular breakaway washer 214 and protective member 314 remaining behind attached to the annular blade 126 due to the washer attachment member 308. The protective member 314 continues to prevent the cutting edge 192 of the annular blade 126 from making an unintended cut after the staple driver 156 and the attached annular blade 126 have been fired. Moreover, the visual indicator 326 continues to indicate that the staple driver 156 and the attached annular blade 126 have been fired.

Figure 35:
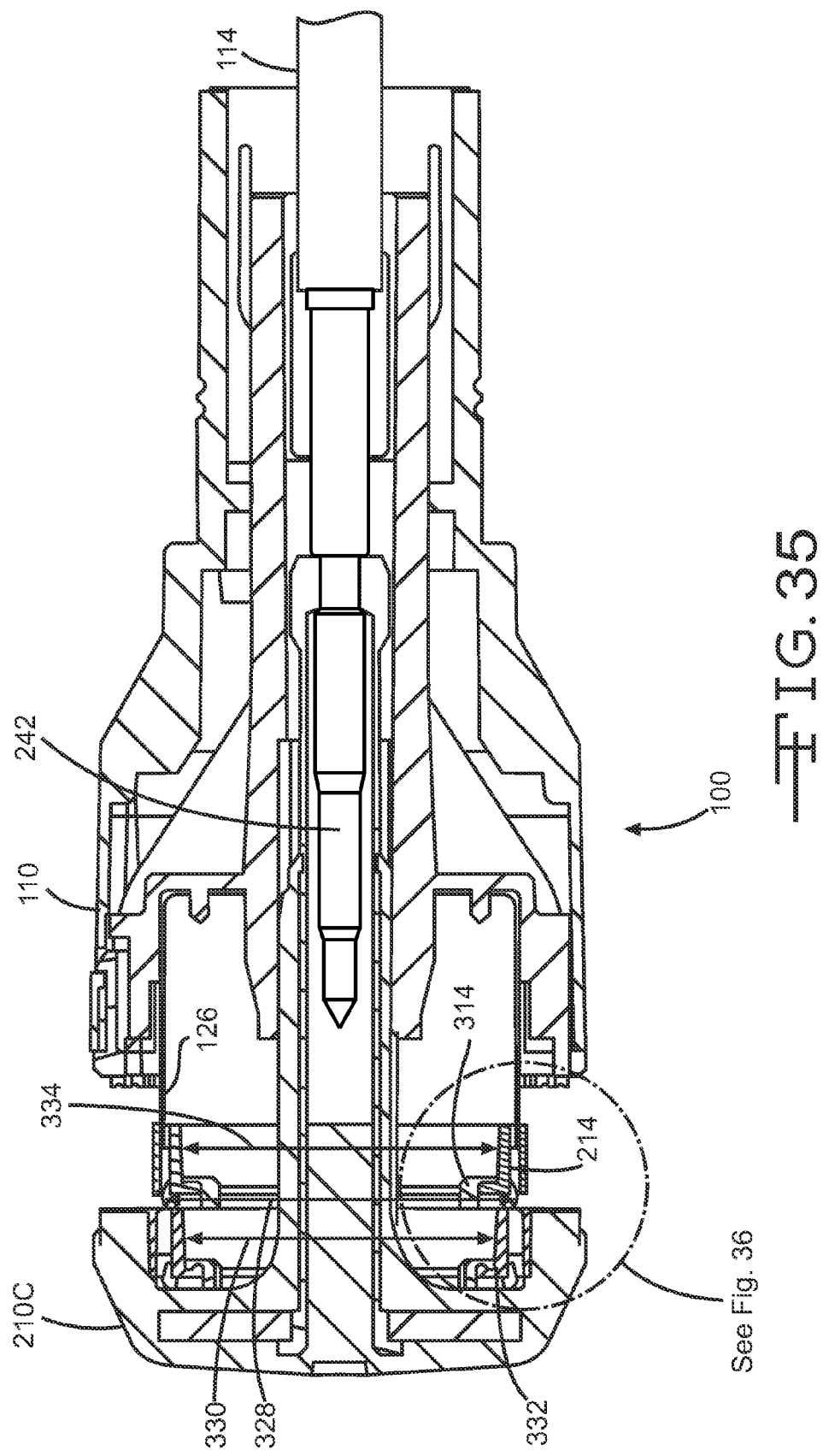
FIG. 35 illustrates the view of FIG. 34 with a new anvil having been attempted to be attached to the stapling reload assembly and the protective member and the annular breakaway washer interfering with the attachment.
Figure 36:
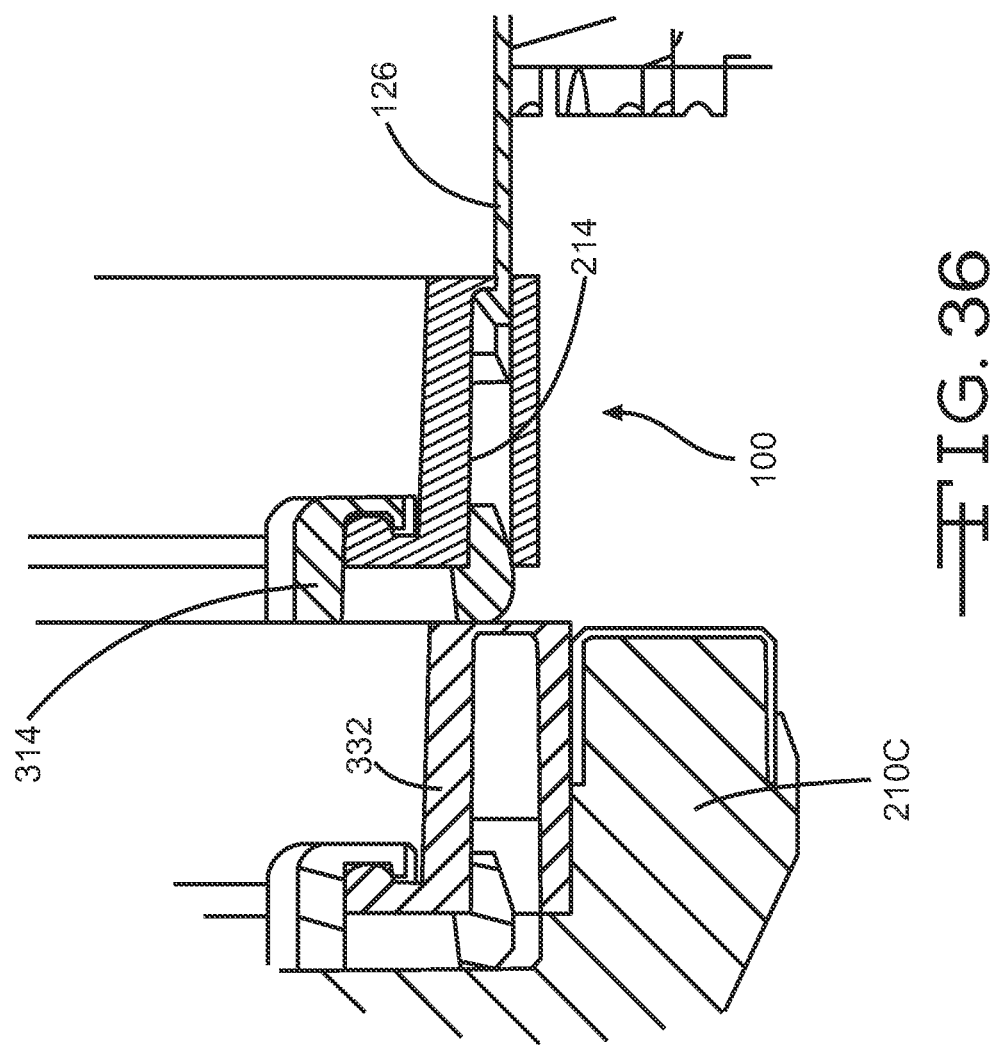
FIG. 36 illustrates a close-up view within the dotted circle of FIG. 35 showing the protective member and the annular breakaway washer interfering with the attachment of the new anvil to the stapling reload assembly.

FIG. 35 illustrates a new anvil 210C having attempted to be attached to the circular stapling instrument 100 of FIG. 34. As shown in FIG. 36, the protective member 314, attached to the annular breakaway washer 214 which is attached to the fired annular blade 126, interferes with the new anvil 210C from being attached to the circular stapling instrument 100. As shown in FIG. 35, this is due to the diameter 328 of the protective member 314 being greater than an inner diameter 330 of the new annular breakaway washer 332. Even if the protective member 314 was not attached to the annular breakaway washer 214, the annular breakaway washer 214 would still interfere with the new anvil 210C from being attached to the circular stapling instrument 100 as a result of the annular breakaway washer 214 having the same or larger diameter 334 as the inner diameter 330 of the new annular breakaway washer 332.

Figure 37:
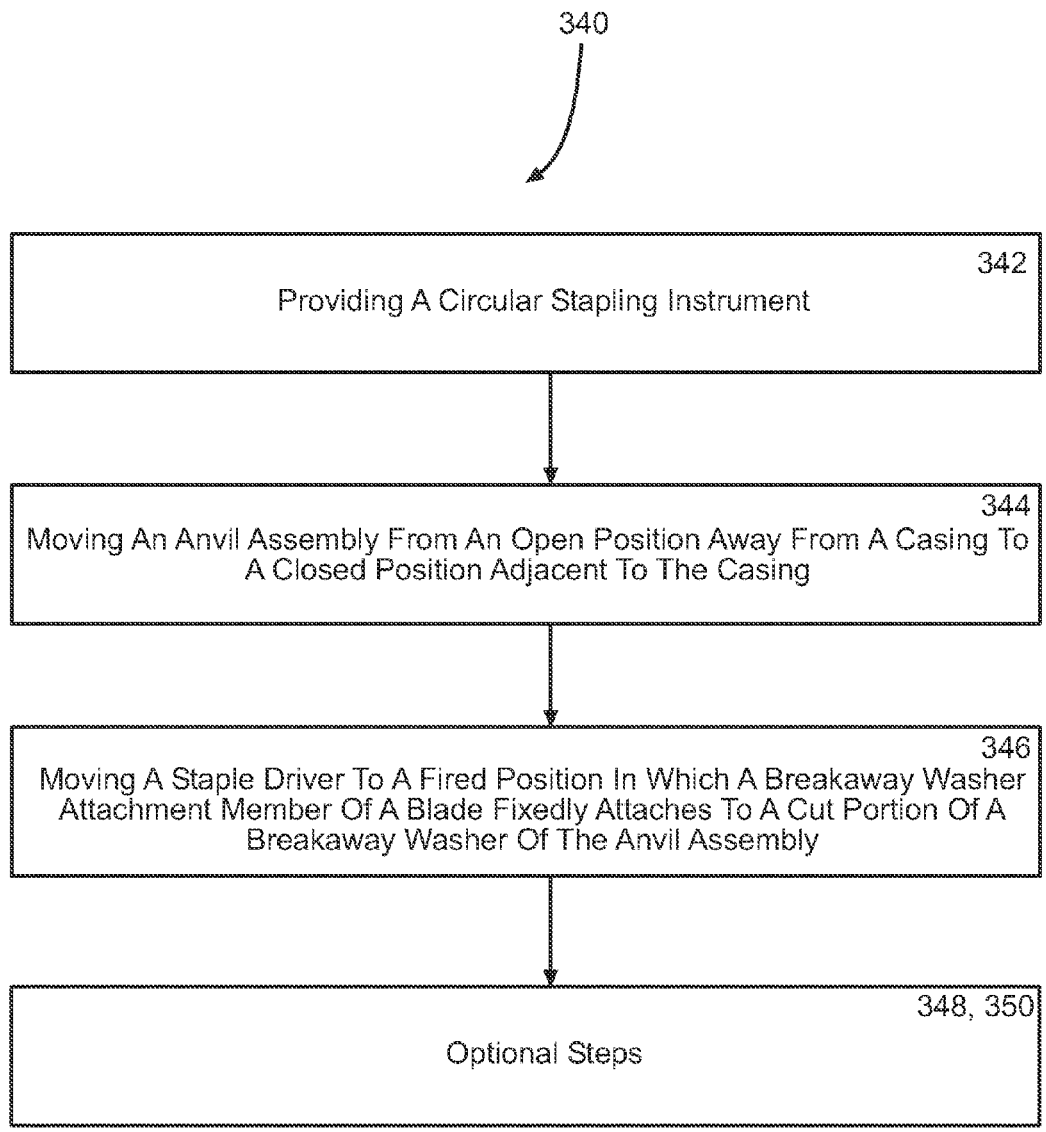
FIG. 37 illustrates a flowchart of one embodiment of a method of locking a blade to a breakaway washer of a circular stapling instrument.

In order to use the circular stapling instrument 100 of FIG. 34 again, the stapling reload assembly 102 shown in FIGS. 1-2 may be removed from the circular stapling instrument 100 thereby removing the fired annular blade 126 and the attached breakaway washer 214. After sterilizing the un-removed portion (such as handle 116 and other un-removed components of FIG. 1) of the circular stapling instrument 100, another unused stapling reload assembly, comprising another unused annular blade and another unused breakaway washer, may be attached to the sterilized un-removed portion of the circular stapling instrument 100 prior to using the circular stapling instrument 100 again. FIG. 37 illustrates a flowchart of one embodiment of a method 340 of locking a blade to a breakaway washer of a circular stapling instrument. In step 342, a circular stapling instrument is provided. The provided circular stapling instrument comprises a casing, a staple driver, an anvil assembly, and a blade. The staple driver is moveably disposed within the casing. The anvil assembly comprises a breakaway washer attached to an anvil base surface. The blade is attached to the staple driver.

In step 344, the anvil assembly is moved from an open position away from the casing to a closed position adjacent to the casing. In step 346, the staple driver is moved from a pre-fired position, in which the blade has not cut the breakaway washer and in which a breakaway washer attachment member of the blade has not attached to the breakaway washer, to a fired position in which the blade cuts the breakaway washer and the breakaway washer attachment member of the blade fixedly attaches to the breakaway washer. The breakaway washer attachment member may comprise at least one breakaway washer retention barb extending from the blade at a non-parallel angle to a cutting edge of the blade. The non-parallel angle may be in a range of 56 to 60 degrees. In other embodiments, the non-parallel angle may be in a range of 30 to 60 degrees. In still other embodiments, the breakaway washer attachment member may vary. In one embodiment, step 346 may comprise the blade cutting a web of the breakaway washer, and the at least one breakaway washer retention barb fixedly attaching to one of spaced-apart walls of the breakaway washer.

In optional step 348, one or more of the following may occur: the breakaway washer may interfere with one or more components of the circular stapling instrument to prevent the blade from being retracted into the casing to be used again; the breakaway washer, or a protective member attached to the breakaway washer, may act as a protective barrier over the blade; or a visual indicator of the breakaway washer, or of another member attached to the breakaway washer, may visually indicate that the staple driver has been fired.

In optional step 350, the following steps may be followed: a stapling reload assembly may be removed from the circular stapling instrument thereby removing the used blade and the breakaway washer; an un-removed portion of the circular stapling instrument may be sterilized; and an unused stapling reload assembly may be attached to the circular stapling instrument, comprising an unused blade and an unused breakaway washer, prior to using the circular stapling instrument again. In other embodiments, one or more steps of the method 340 may be varied.

One or more embodiments of the disclosure may result in any of the following: the prevention of a used blade of a fired circular stapling instrument from being inadvertently used again in another procedure thereby improving cleanliness and safety; the prevention of a used blade of a fired circular stapling instrument from making an unintended cut; the prevention of the misfiring of a circular stapling instrument; or another type of benefit.

Figure 38:
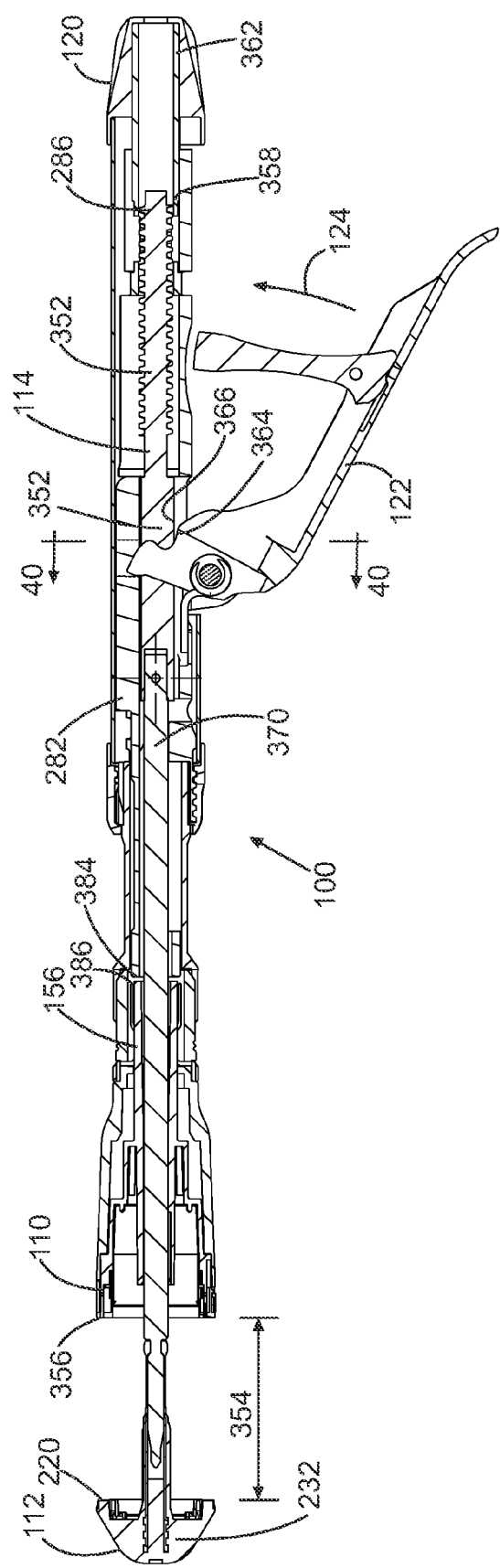
FIG. 38 illustrates a cross-sectional view through the reusable circular stapling instrument of FIG. 1 with the anvil assembly disposed in an open position, out of a firing zone, away from a casing with a firing trigger in a locked, pre-fired state.
Figure 39:
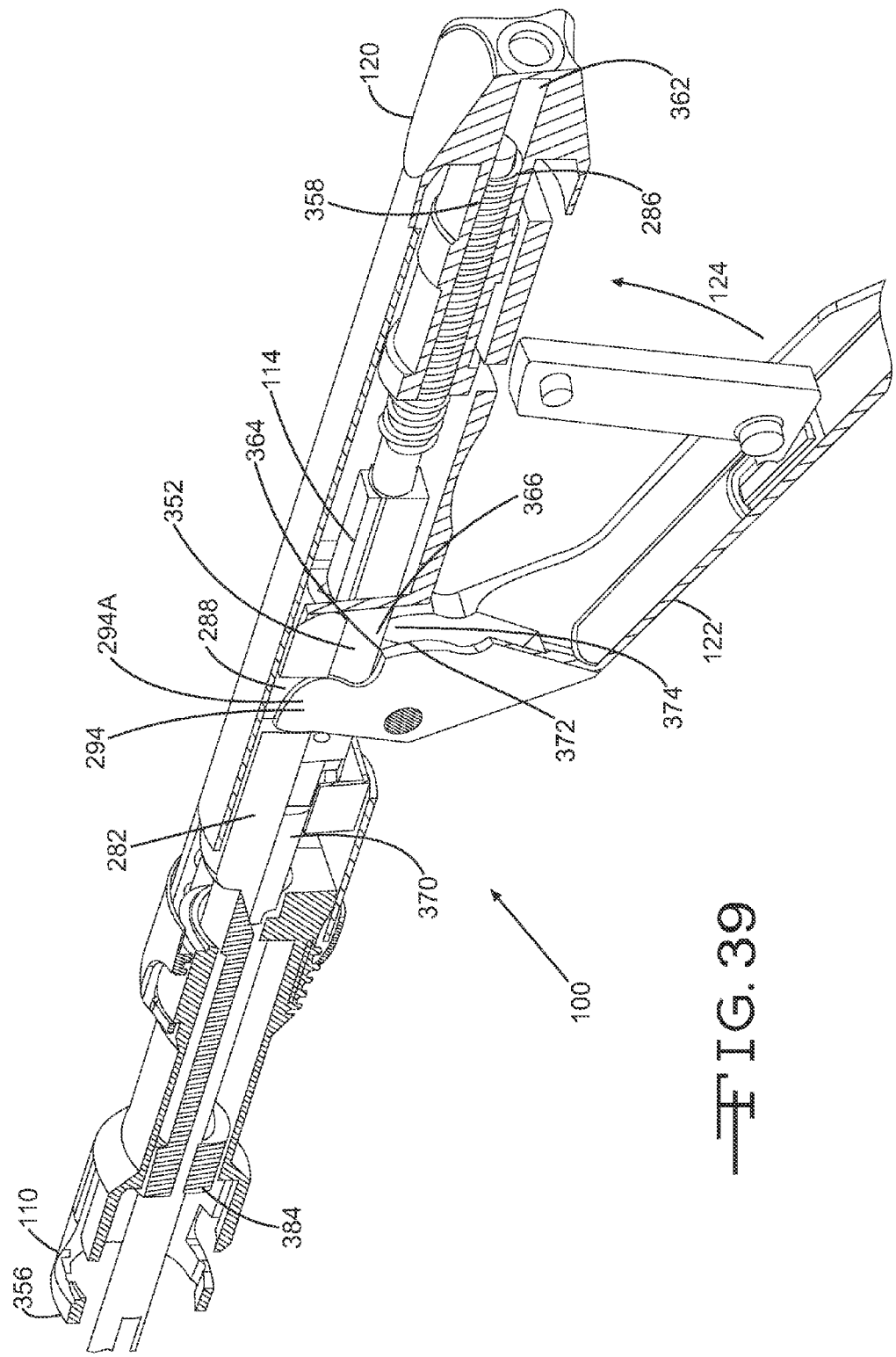
FIG. 39 illustrates a partial perspective view of the cross-sectional view of FIG. 38.
Figure 40:
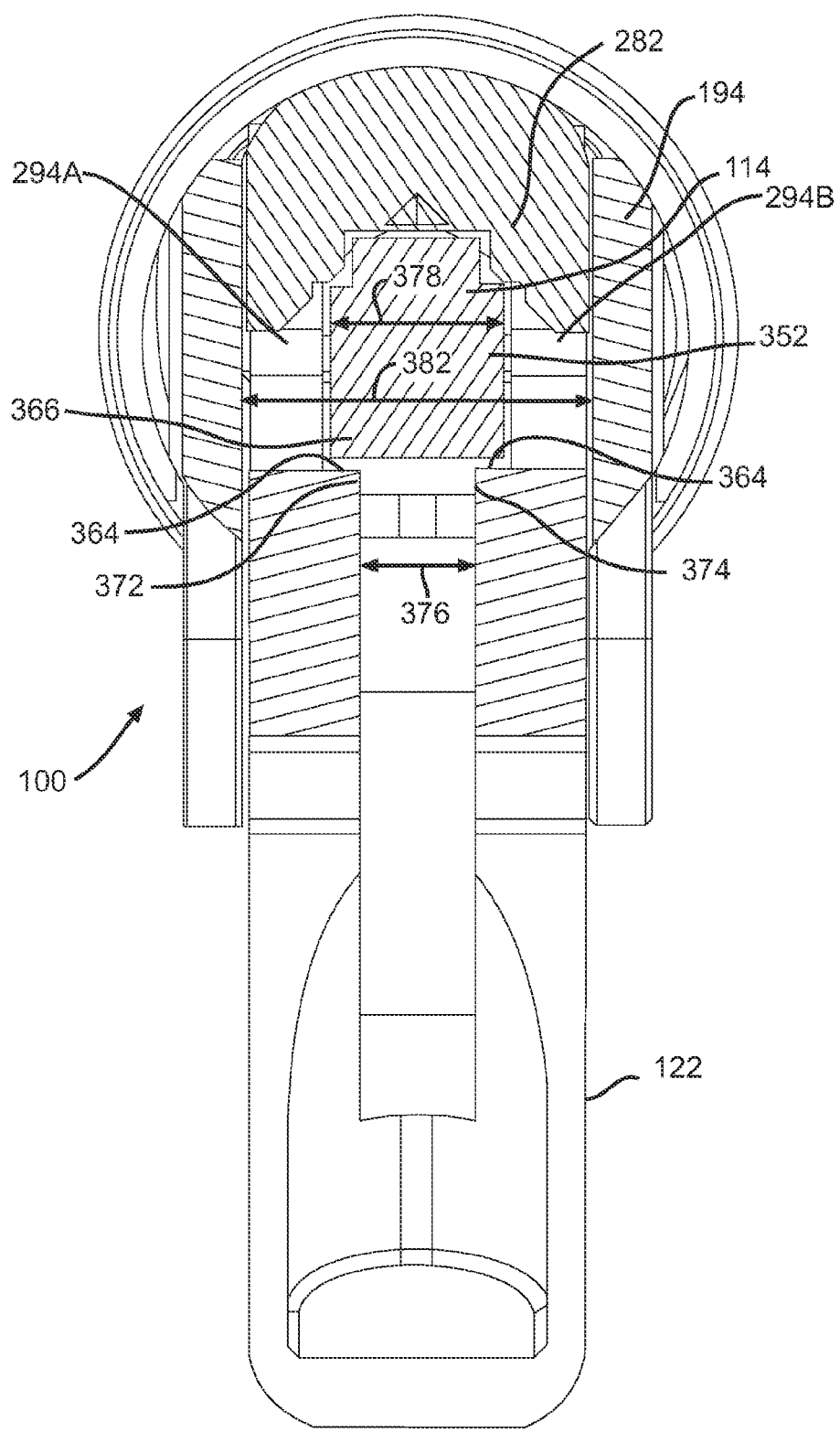
FIG. 40 illustrates a cross-sectional view through line 40-40 of FIG. 38.

FIGS. 38-46 illustrate various views of the circular stapling instrument 100 of the embodiment of FIGS. 1 and 2 showing a locking mechanism 352, in various states, that may be used with any embodiments of the disclosure to prevent misfiring of the firing trigger 122 and corresponding staple driver 156. FIGS. 38-40 illustrate various views of the anvil assembly 112 disposed in an open position, out of a firing zone, away from the casing 110 with the firing trigger 122 and the indirectly affected staple driver 156 in a locked state in pre-fired positions. When the anvil assembly 112 is disposed in the open position, out of the firing zone, away from the casing 110, using the attached reciprocating anvil adjusting rod 114 and anvil control member 120, the anvil base surface 220 is disposed at a distance 354 in a range of 0.100 to 3.0 inches away from the end of the staple guide 148. In this pre-fired position, a threaded end 286 of the reciprocating anvil adjusting rod 114 is disposed at and within an inner portion 358 of the mating threaded shaft 360 of the anvil control member 120, and is disposed apart from end 362 of the mating threaded shaft 360 of the anvil control member 120.

A ledge 364 of the firing trigger 122 is abutted against a first portion 366 of the reciprocating anvil adjusting rod 114 which acts as the locking mechanism 352 and blocks and prevents the firing trigger 122 from rotating in direction 124. A second portion 370 of the reciprocating anvil adjusting rod 114 is disposed apart from the ledge 364. The ledge 364 comprises opposed walls 372 and 374 which are disposed a distance 376 of 0.190 inches apart. The width 378 of the first portion 366 of the reciprocating anvil adjusting rod 114 is 0.290 inches. The width 380 (see FIG. 43) of the second portion 370 of the reciprocating anvil adjusting rod 114 is 0.170 inches. The firing trigger 122 is prevented from rotating in direction 124 due to the width 378 of the first portion 366 being greater than the distance 376 between the opposed walls 372 and 374 of the ledge 364.

The upper end 294 of the firing trigger 122 is mated in engagement grooves 288 and 290 (see FIG. 3) of the firing bar 282. The upper end 294 of the firing trigger 122 comprises opposed surfaces 294A and 294B which are disposed a distance 382 of 0.574 inches apart. The distance 382 between the opposed surfaces 294A and 294B is greater than the width 378 of the first portion 366 allowing the opposed surfaces 294A and 294B to pass over the first portion 366 into the engagement grooves 288 and 290. End 384 of the firing bar 282 is disposed apart from an end 386 of the staple driver 156. As a result of the first portion 366 of the reciprocating anvil adjusting rod 114 blocking the firing trigger 122 from rotating in direction 124, the end 384 of the firing bar 282, which is mated to the firing trigger 122, remains in a position disposed apart from the end 386 of the staple driver 156 keeping the staple driver 156 in the pre-fired, locked state.

Figure 41:
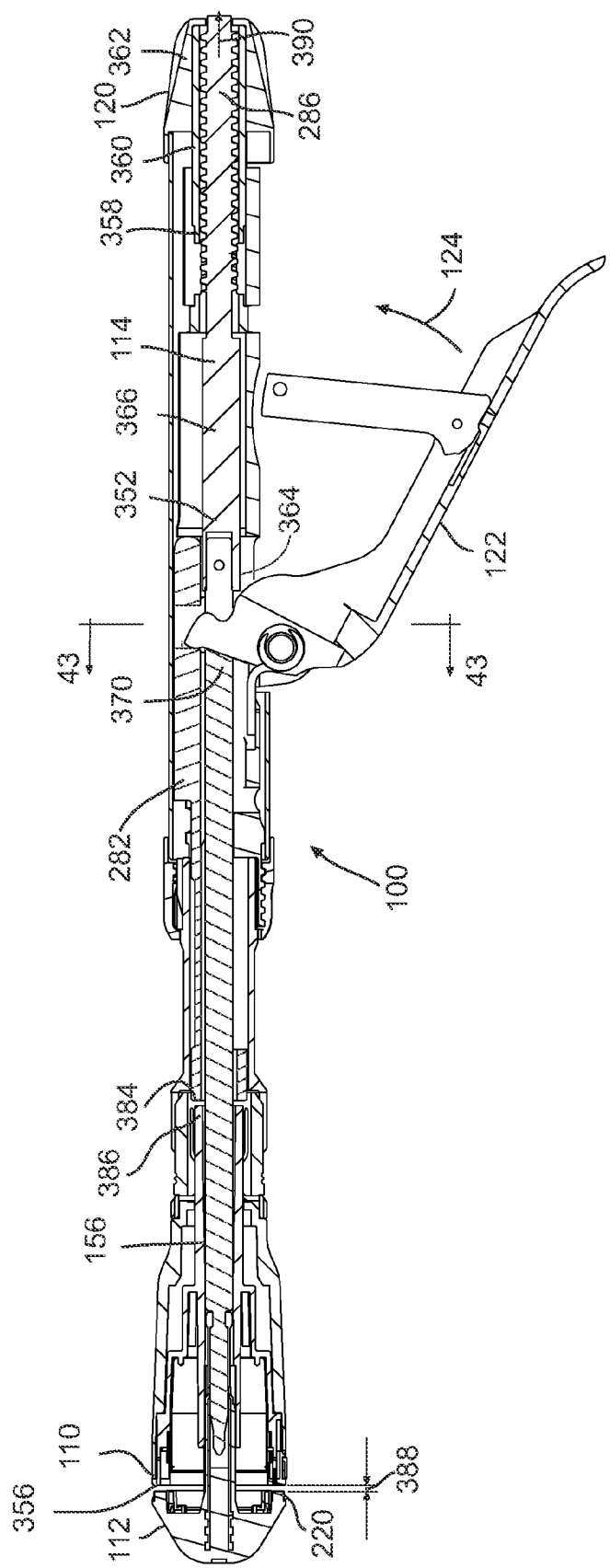
FIG. 41 illustrates a cross-sectional view through the reusable circular stapling instrument of FIG. 1 with the anvil assembly disposed in a closed position, in the firing zone, adjacent the casing with the firing trigger in an unlocked, pre-fired state ready to fire.
Figure 42:
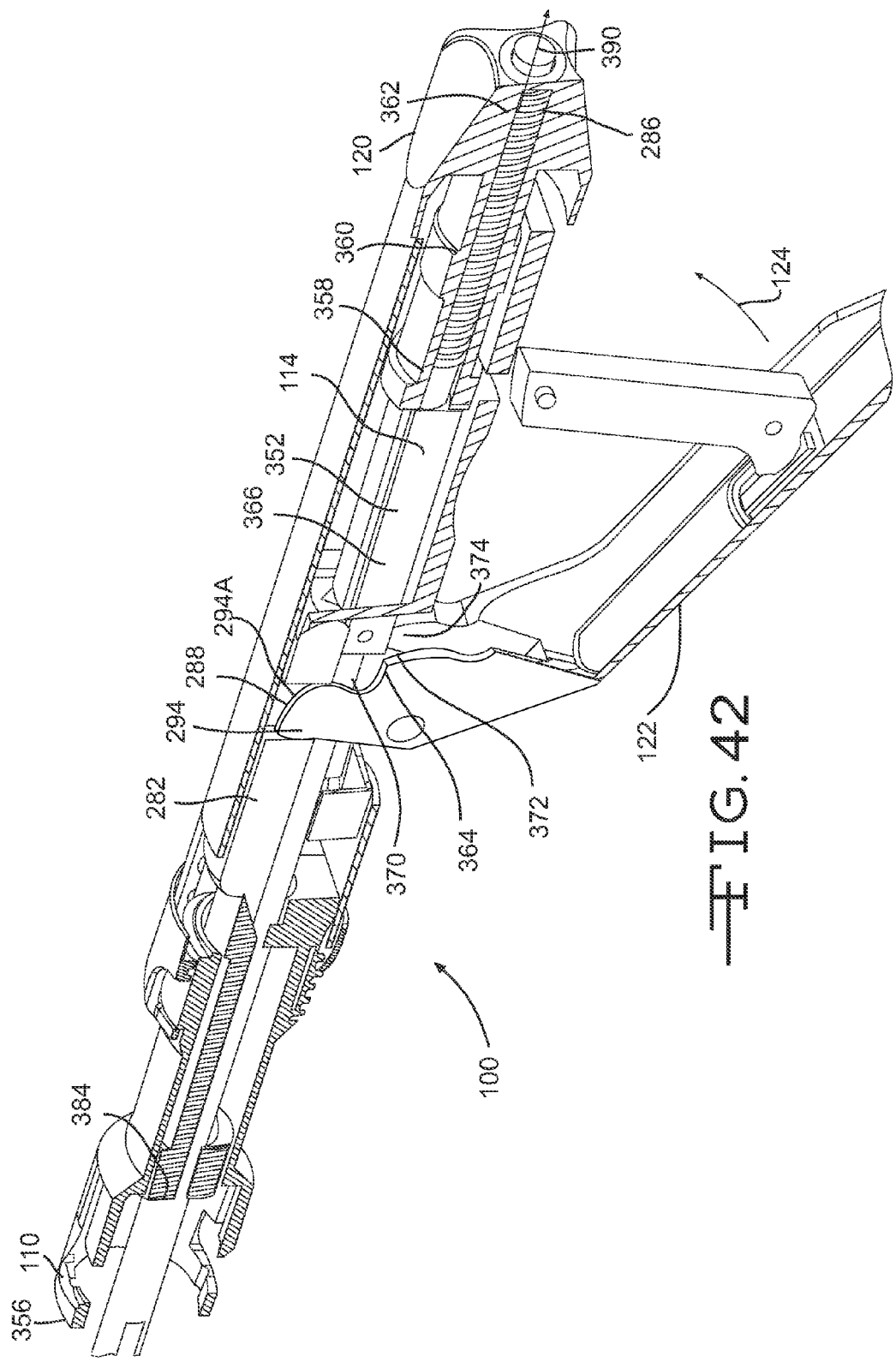
FIG. 42 illustrates a partial perspective cross-sectional view of FIG. 41.
Figure 43:
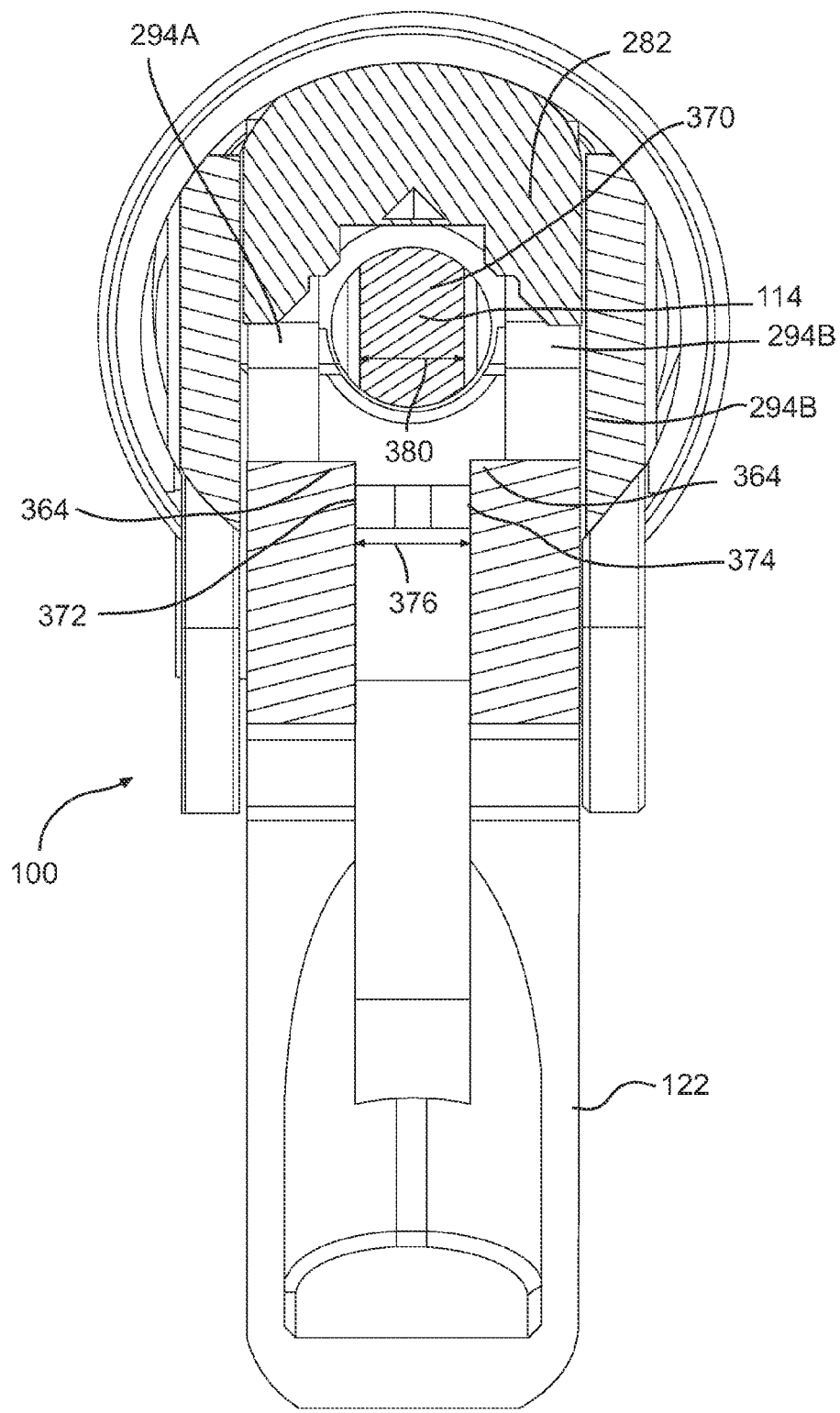
FIG. 43 illustrates a cross-sectional view through line 43-43 of FIG. 41.

FIGS. 41-43 illustrate various views of the anvil assembly 112 disposed in a closed position, in the firing zone, adjacent the casing 110 with the firing trigger 122 and the indirectly affected staple driver 156 in an unlocked state ready to fire but still in their same pre-fired positions as shown in FIGS. 38-40. When the anvil assembly 112 is disposed in the closed position in the firing zone adjacent the casing 110, using the attached reciprocating anvil adjusting rod 114 and anvil control member 120, the anvil base surface 220 is disposed at a distance 388 in a range of 0.06 to 0.100 inches away from the end of the staple guide 148. The anvil control member 120 has been rotated causing the threaded end 286 of the reciprocating anvil adjusting rod 114 to move in direction 390 away from the inner portion 358 of the mating threaded shaft 360 of the anvil control member 120 towards and to the end 362 of the mating threaded shaft 360 of the anvil control member 120. As a result of this movement, the first portion 366 of the reciprocating anvil adjusting rod 114 has been moved in direction 390 to be disposed apart from the opposed walls 372 and 374 of the ledge 364 so that the first portion 366 no longer interferes with the ledge 364. The second portion 370 of the reciprocating anvil adjusting rod 114 has also been moved in direction 390 from a position apart from the ledge 364 to a position disposed over the ledge 364.

Due to the width 380 of the second portion 370 being less than the distance 376 between the opposed walls 372 and 374 of the ledge 364, the firing trigger 122 may now be freely fired without abutting against the adjacent second portion 370. The opposed surfaces 294A and 294B of the upper end 294 of the firing trigger 122 are still mated in the engagement grooves 288 and 290 (see FIG. 3) of the firing bar 282. Because the firing trigger 122 has not been rotated in direction 124 and, although unlocked, is still in the pre-fired position, the firing trigger 122 has not moved the mating firing bar 282 and the end 384 of the firing bar 282 is still disposed apart from the end 386 of the staple driver 156 leaving the staple driver 156 in its unfired position, but ready to be fired.

Figure 44:
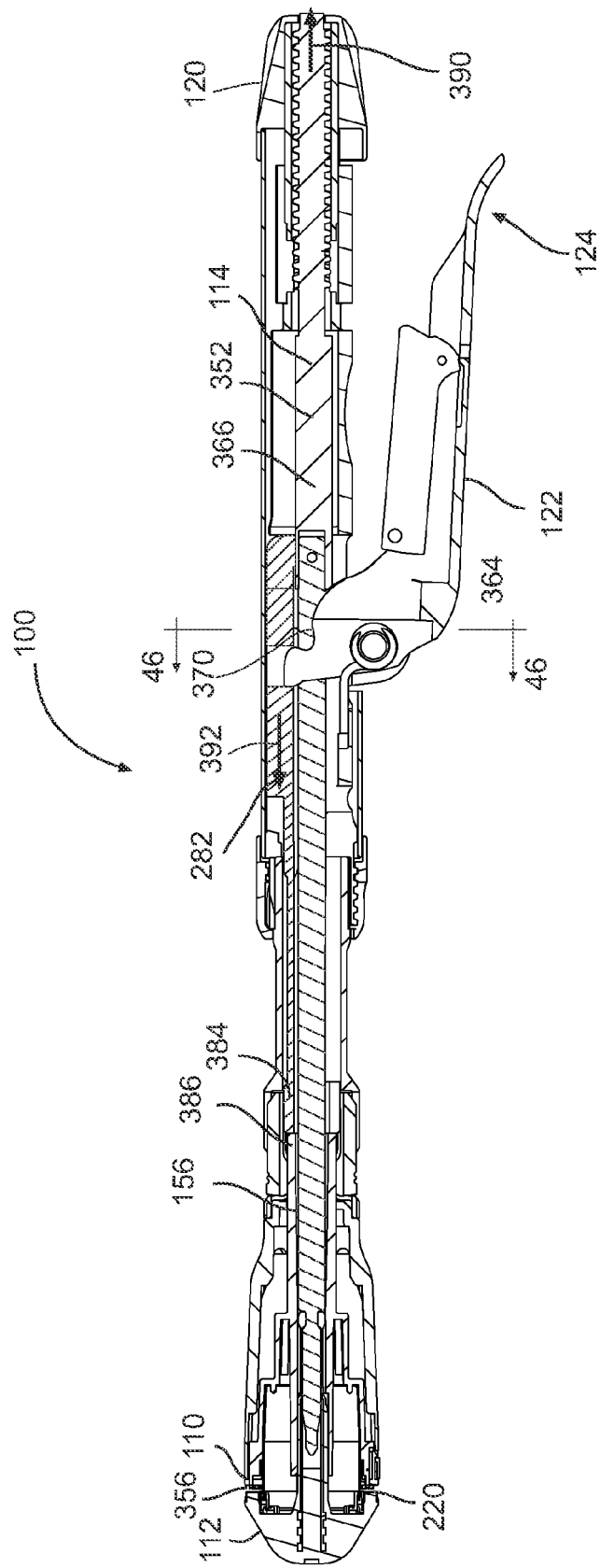
FIG. 44 illustrates a cross-sectional view through the reusable circular stapling instrument of FIG. 1 with the anvil assembly disposed in the closed position, in the firing range, adjacent the casing with the firing trigger having been fired.
Figure 45:
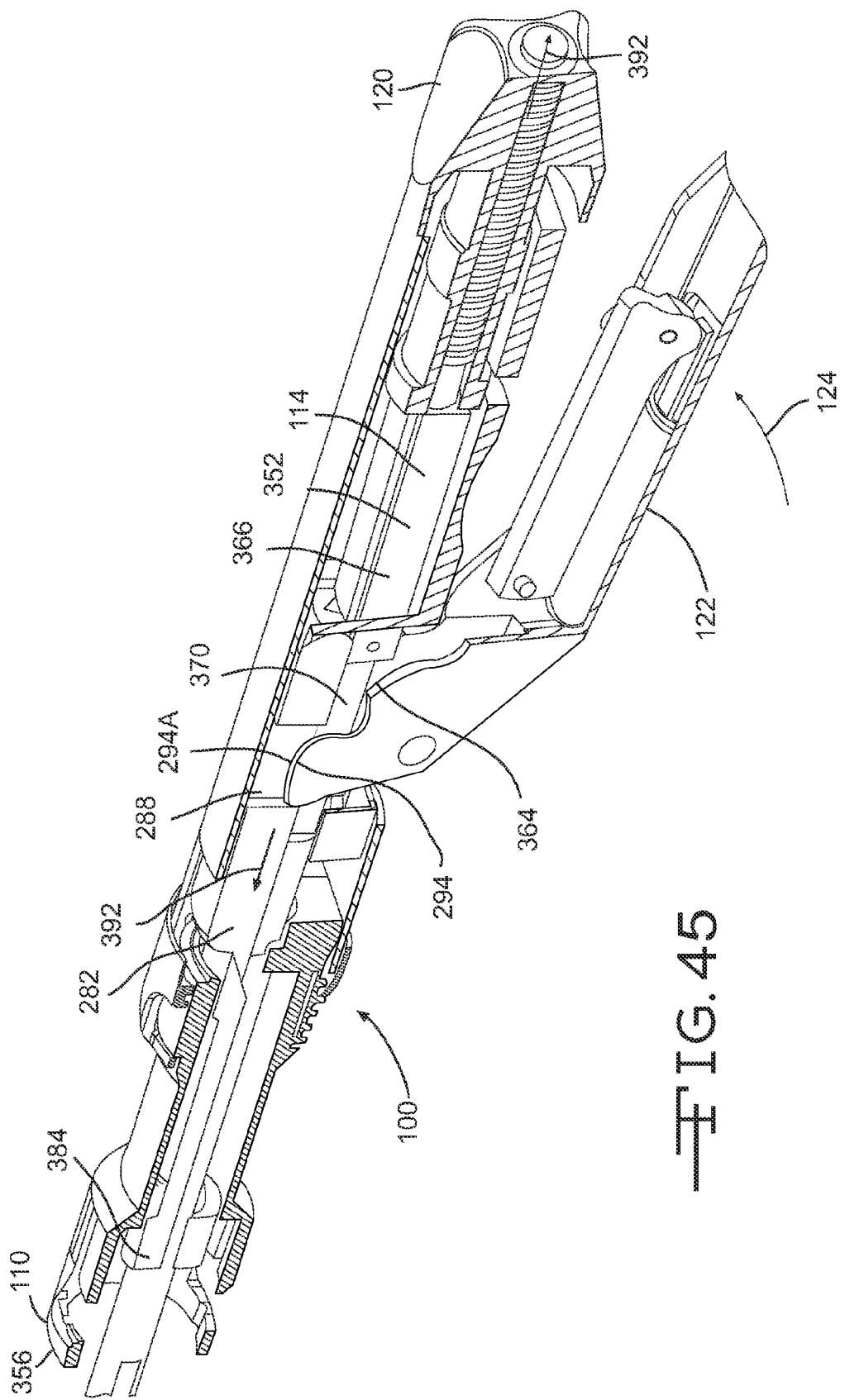
FIG. 45 illustrates a partial perspective view of the cross-sectional view of FIG. 44.
Figure 46:
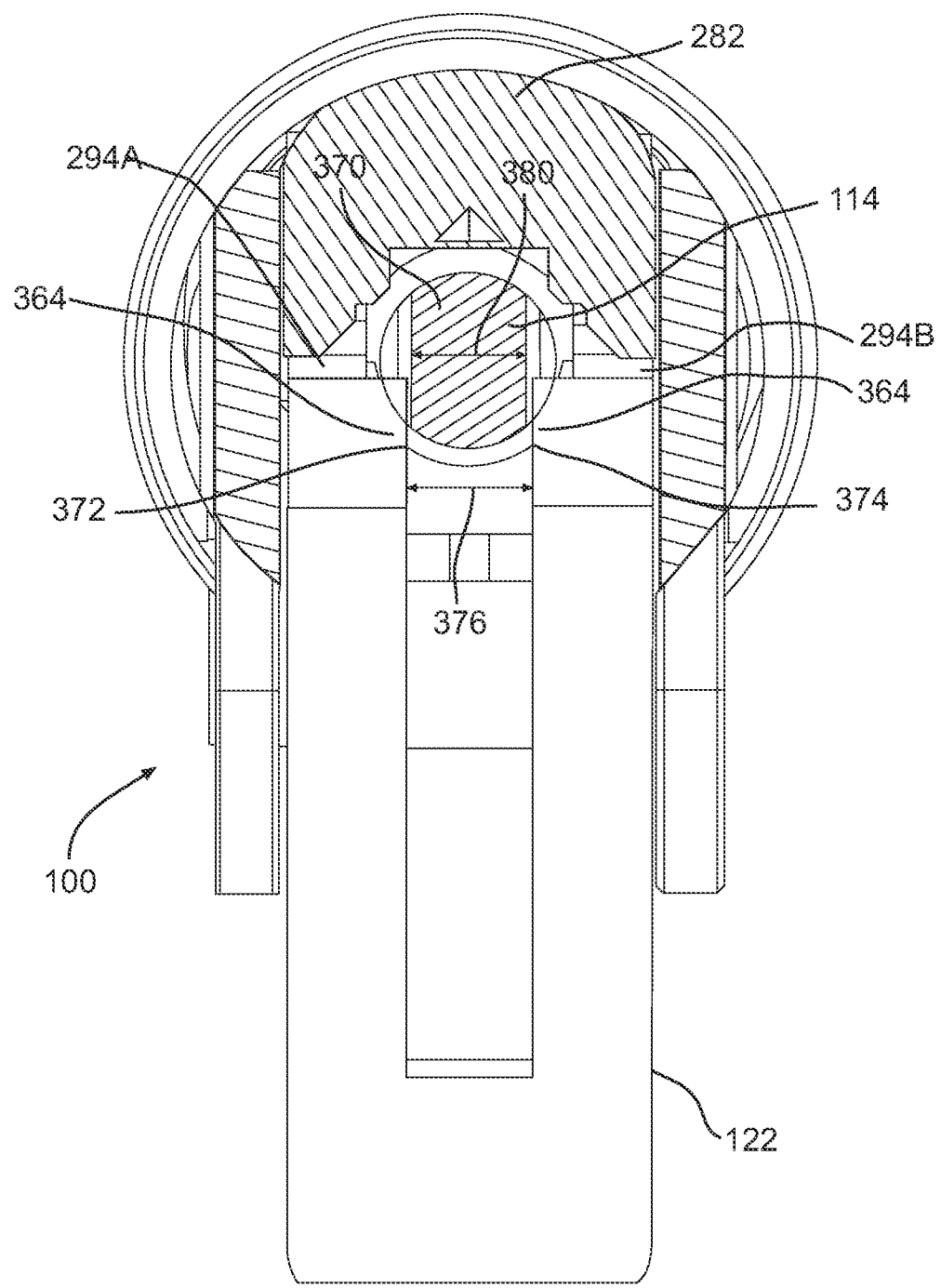
FIG. 46 illustrates a cross-sectional view through line 46-46 of FIG. 44.

FIGS. 44-46 illustrate various views of the anvil assembly 112 disposed in the closed position, in the firing range, adjacent the casing 110 with the firing trigger 122 having been rotated in direction 124 firing the firing trigger 122 and the indirectly affected staple driver 156. The firing trigger 122 was allowed to fire because the first portion 366 of the reciprocating anvil adjusting rod 114 was previously moved in direction 390 to be disposed apart from the ledge 364 so that the first portion 366 no longer interfered with the ledge 364, and the width 380 of the second portion 370 of the reciprocating anvil adjusting rod 114 is less than the distance 376 between the opposed walls 372 and 374 of the ledge 364 which allowed the firing trigger 122 to be fired without interference from the second portion 370.

During the firing of the firing trigger 122, as the firing trigger 122 was rotated in direction 124, the opposed surfaces 294A and 294B of the upper end 294 of the firing trigger 122 moved in direction 392 abutting against the respective mated engagement grooves 288 and 290 (see FIG. 3) of the firing bar 282 forcing the firing bar 282 to also move in direction 392. This movement forced the end 384 of the firing bar 282 against the end 386 of the staple driver 156 forcing the staple driver 156 to also fire and move in direction 392. During this firing of the staple driver 156, the movement of the staple driver 156 ejects staples 104 (see FIGS. 7 and 31) out of the annular staple holder 148 (see FIGS. 4-5, 7, and 31) and cuts tissue with the annular blade 126 (see FIG. 31) attached to the staple driver 156 as previously discussed.

In such manner, the locking mechanism 352 automatically prevents misfiring of the firing trigger 122 and corresponding staple driver 156 and staples staples 104 (see FIGS. 7 and 31) without a user of the circular stapling instrument 100 having to manually implement a locking mechanism. Moreover, the locking mechanism 352 automatically locks the firing trigger 122 and corresponding staple driver 156 and staples 104 (see FIGS. 7 and 31) in the pre-fired position whenever the anvil assembly 112 is in the open position, and automatically unlocks the firing trigger 122 and corresponding staple driver 156 and staples 104 (see FIGS. 7 and 31) whenever the anvil assembly 112 is in the closed position. The locking mechanism 352 works in this manner regardless of the number of times the anvil assembly 112 has been opened and closed, and regardless of whether the firing trigger 122 and corresponding staple driver 156 and staples 104 (see FIGS. 7 and 31) have been fired.

Figure 47A:
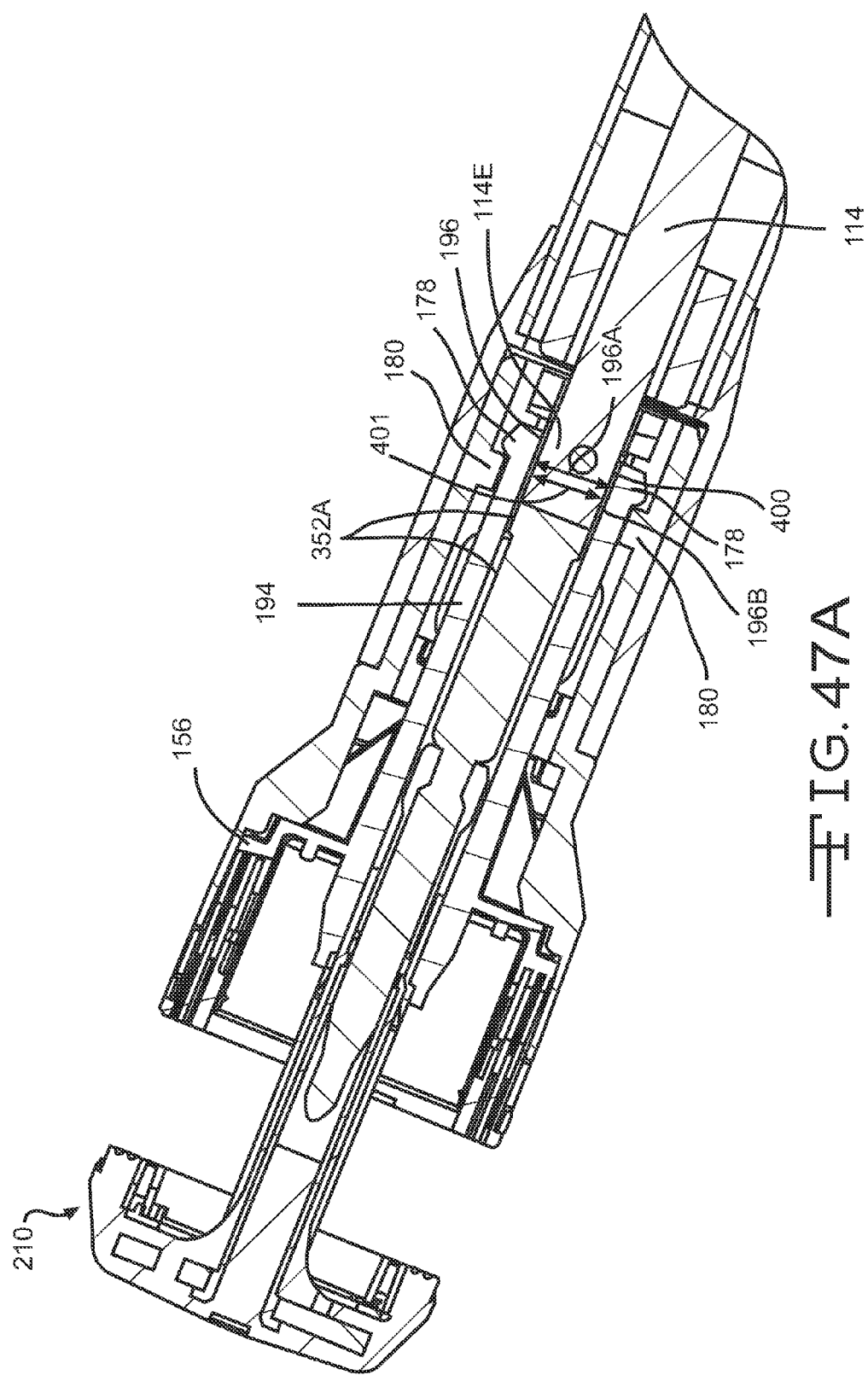

FIG. 47A shows another embodiment of the circular stapling instrument of FIG. 1 having another locking mechanism 352A that prevents movement of the staple driver 156 when the stapling reload assembly 108 (see FIG. 2) is assembled to the handle 116 (see FIG. 2) and the anvil 210 is in the open position. In this condition with the anvil 210 in the open position, the portion 114E of the reciprocating anvil adjusting rod 114 adjacent to the flexible detent members 178 has a size, width, or diameter 401 (see FIG. 3B) which is smaller than but close enough in size to the width or diameter 196A of the hole 196 of the annular interior shaft 194 of the staple driver 156 preventing the flexible detent members 178 from having enough distance 400, between the portion 114E of the anvil adjusting rod 114 and the inner hole surface 196B, to deflect and disengage from the detent bumps 180, thereby in turn preventing movement and firing of the staple driver 156. As shown in FIG. 47B, when the anvil 210 is near the closed position the narrower portion 114F of the reciprocating anvil adjusting rod 114 adjacent to the flexible detent members 178 has a size, width, or diameter 402 (see FIG. 3A) which is smaller enough in size than the width or diameter 196A of the hole 196 of the annular interior shaft 194 of the staple driver 156 to allow the flexible detent members 178 to have enough distance 400, between the portion 114F of the anvil adjusting rod 114 and the inner hole surface 196B, to deflect and disengage from the detent bumps 180, thereby in turn allowing movement and firing of the staple driver 156.

The abstract of the disclosure is provided to allow the reader to quickly ascertain the nature of the technical disclosure. It is submitted with the understanding that it will not be used to interpret or limit the scope or meaning of the claims. In addition, in the foregoing detailed description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the detailed description, with each claim standing on its own as a separately claimed subject matter. While various embodiments of the disclosure have been described, it will be apparent to those of ordinary skill in the art that other embodiments and implementations are possible within the scope of the disclosure. Accordingly, the disclosure is not to be restricted except in light of the attached claims and their equivalents.

The invention claimed is:

1. A stapling cartridge assembly for a circular stapling instrument comprising:
   a casing;
   a staple driver receivable within said casing and configured to move within said casing from a pre-fired position to a fired position; and
   a blade attachable to said staple driver, wherein said blade comprises a cutting edge and a breakaway washer attachment member for fixedly attaching to a breakaway washer, when the staple driver is moved from the pre-fired position to the fired position, so that the breakaway washer moves with the breakaway washer attachment member due to the fixed attachment of the breakaway washer attachment member to the breakaway washer.

2. The stapling cartridge assembly of claim 1 wherein the breakaway washer attachment member comprises at least one breakaway washer retention barb extending from the blade at a non-parallel angle to the cutting edge.

3. The stapling cartridge assembly of claim 2 wherein said non-parallel angle is in a range of 30 degrees to 60 degrees.

4. The stapling cartridge assembly of claim 2 wherein said at least one breakaway washer retention barb extends from the blade at a location adjacent to the cutting edge.

5. The stapling cartridge assembly of claim 1 wherein the breakaway washer attachment member extends away from the cutting edge at a top portion of the blade towards a bottom portion of the blade.

6. The stapling cartridge assembly of claim 1 wherein the blade comprises a cavity within the blade and the breakaway washer attachment member is completely disposed within the cavity within the blade.

* * * * *